United States Patent [19]
Beck et al.

[11] Patent Number: 5,980,953
[45] Date of Patent: Nov. 9, 1999

[54] ANTI-INFLAMMATORY FACTOR, METHOD OF ISOLATION, AND USE

[75] Inventors: Lee R. Beck, Lebanon; J. Peter Fuhrer, Dayton, both of Ohio

[73] Assignee: Stolle Milk Biologics, Inc., Cincinnati, Ohio

[21] Appl. No.: 08/898,028

[22] Filed: Jul. 22, 1997

Related U.S. Application Data

[63] Continuation-in-part of application No. 08/316,474, Oct. 3, 1994, Pat. No. 5,650,175.

[51] Int. Cl.$^6$ ..................................................... A61K 35/20
[52] U.S. Cl. ......................... 424/535; 424/278.1; 514/54; 536/24
[58] Field of Search ............................... 424/278.1, 535; 514/54; 536/24

[56] References Cited

U.S. PATENT DOCUMENTS

| | | | |
|---|---|---|---|
| 3,128,230 | 4/1964 | Heinbach | 167/78 |
| 3,376,198 | 4/1968 | Petersen et al. | 167/78 |
| 4,284,623 | 8/1981 | Beck | 424/85 |
| 4,324,782 | 4/1982 | Beck | 424/87 |
| 4,636,384 | 1/1987 | Stolle et al. | 424/87 |
| 4,732,757 | 3/1988 | Stolle et al. | 424/87 |
| 4,897,265 | 1/1990 | Stolle et al. | 424/87 |
| 4,956,349 | 9/1990 | Beck | 514/54 |
| 5,352,462 | 10/1994 | Beck | 424/278.1 |

FOREIGN PATENT DOCUMENTS

| | | |
|---|---|---|
| 0 064 103 | 11/1982 | European Pat. Off. . |
| 0 300 102 | 1/1989 | European Pat. Off. . |
| 0 336 694 | 10/1989 | European Pat. Off. . |
| 53-026312 | 3/1978 | Japan . |
| 1 211 876 | 11/1970 | United Kingdom . |
| 1 442 283 | 7/1976 | United Kingdom . |
| 1 484 131 | 8/1977 | United Kingdom . |
| WO 89/09602 | 10/1989 | WIPO . |
| WO 92/04035 | 3/1992 | WIPO . |
| WO 94/09799 | 5/1994 | WIPO . |

OTHER PUBLICATIONS

Goldman, A.S. et al., "Anti-inflammatory Properties of Human Milk," *Acta. Poediatr. Scand.* 75:689–695 (1986).

Owens, W.E. and Nickerson, S.C., "Evaluation of an Anti-Inflammatory Factor Derived from Hyperimmunized Cows," *Proc. Soc. Exp. Biol. Med.* 190(1):79–86 (1989).

Derwent WPI Acc. No. 78–29814A/197816, English Language Abstract for Japanese Patent Publication No. 53–26312, published Mar. 11, 1978 (Doc. A01).

Ormrod, D.J. et al., "A low molecular weight component derived from the milk of hyperimmunised cows suppresses inflammation by inhibiting neutrophil emigration," *Agents Actions* 37:70–79 (1992).

Ormrod, D. J. et al., "Milk from hyperimmunized dairy cows as a source of a novel biological response modifier," *Agents Actions* 38, Spec. Conf. Issue:C146–C149 (1993).

*Primary Examiner*—Jean C. Witz
*Attorney, Agent, or Firm*—Sterne, Kessler, Goldstein & Fox P.L.L.C.

[57] ABSTRACT

The invention relates to an anti-inflammatory factor isolated from milk, methods of purifying the anti-inflammatory factor resulting in substantially or highly purified preparations and to methods for using this factor to remove adhered neutrophils from endothelial cells, to prevent the emigration of cells from the vasculature and to suppress the response of lymphocytes to foreign antigens.

22 Claims, 45 Drawing Sheets

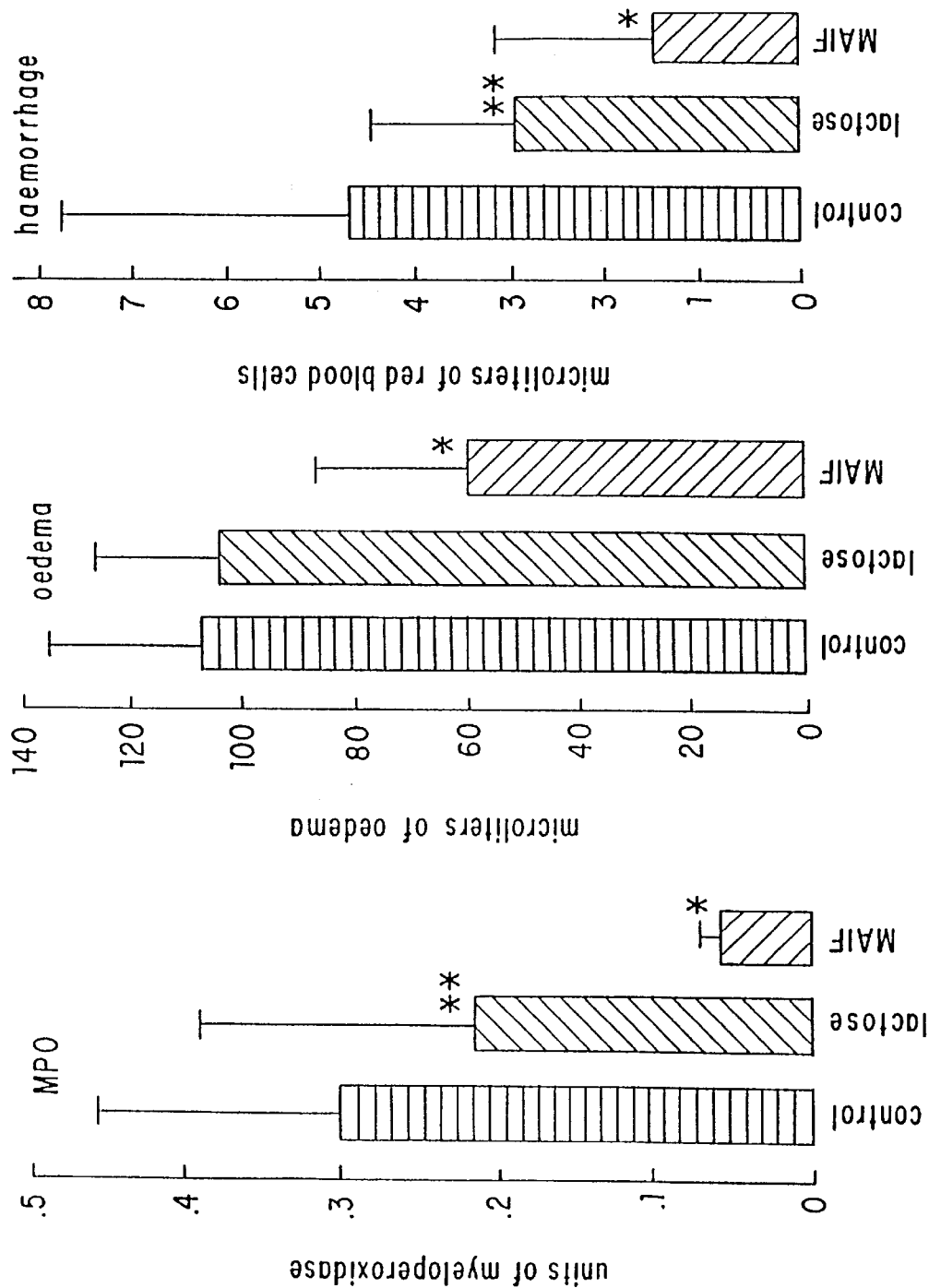

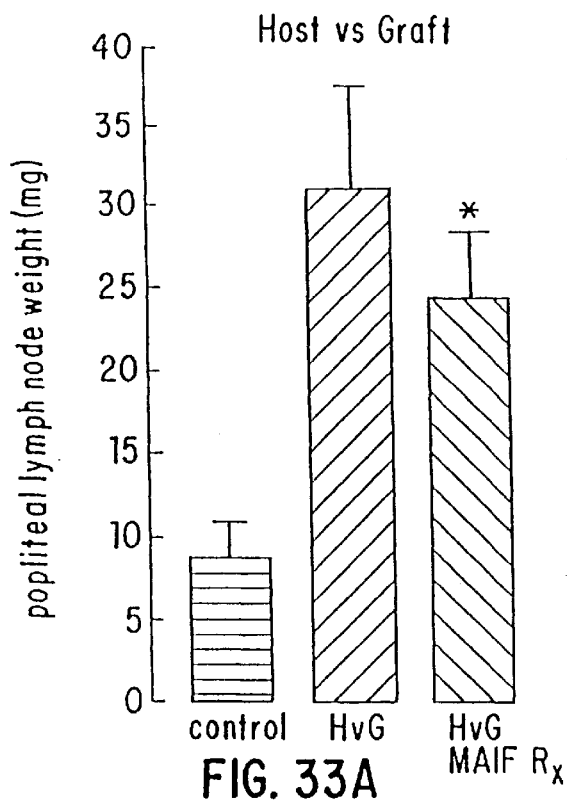
FIG. 33A
FIG. 33C
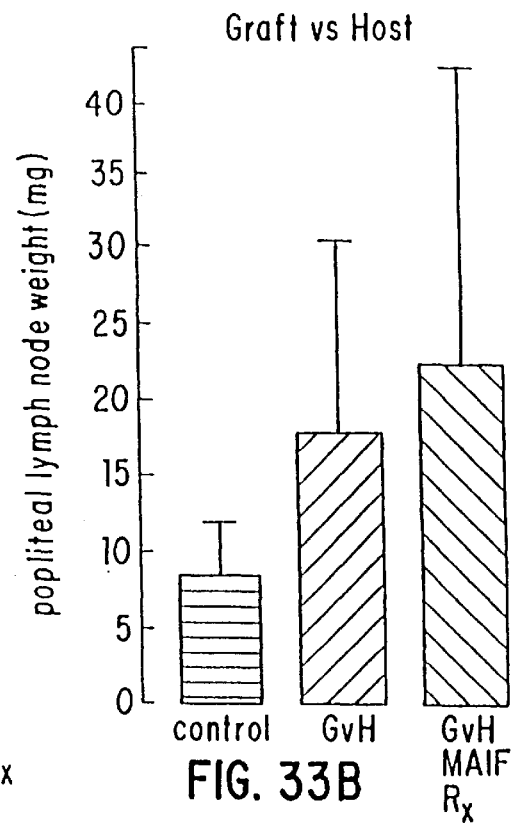
FIG. 33B
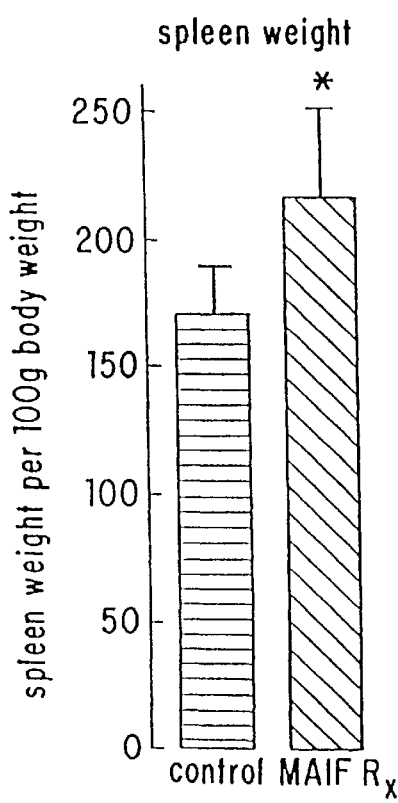
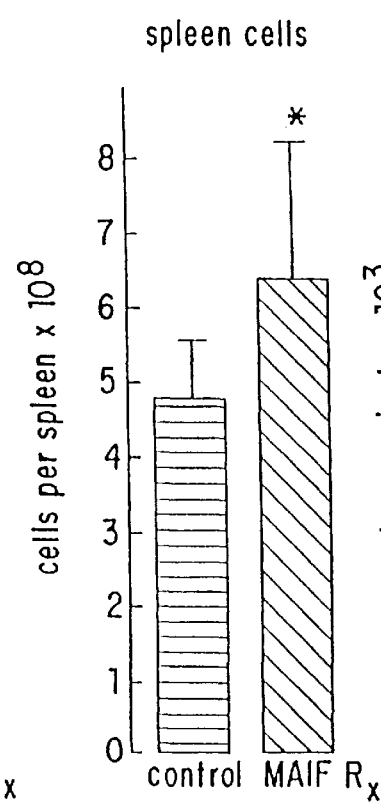
FIG. 33D
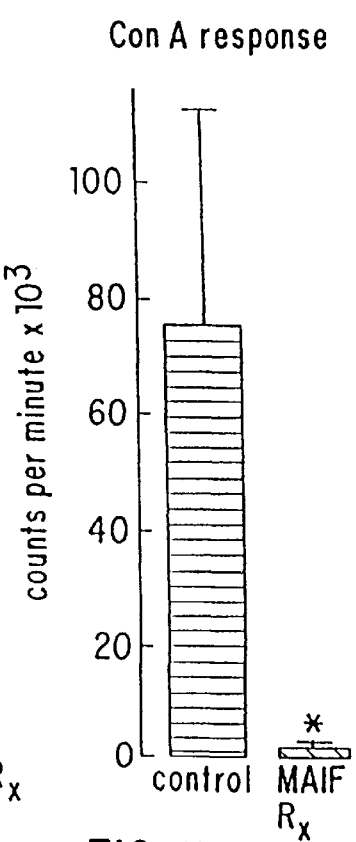
FIG. 33E

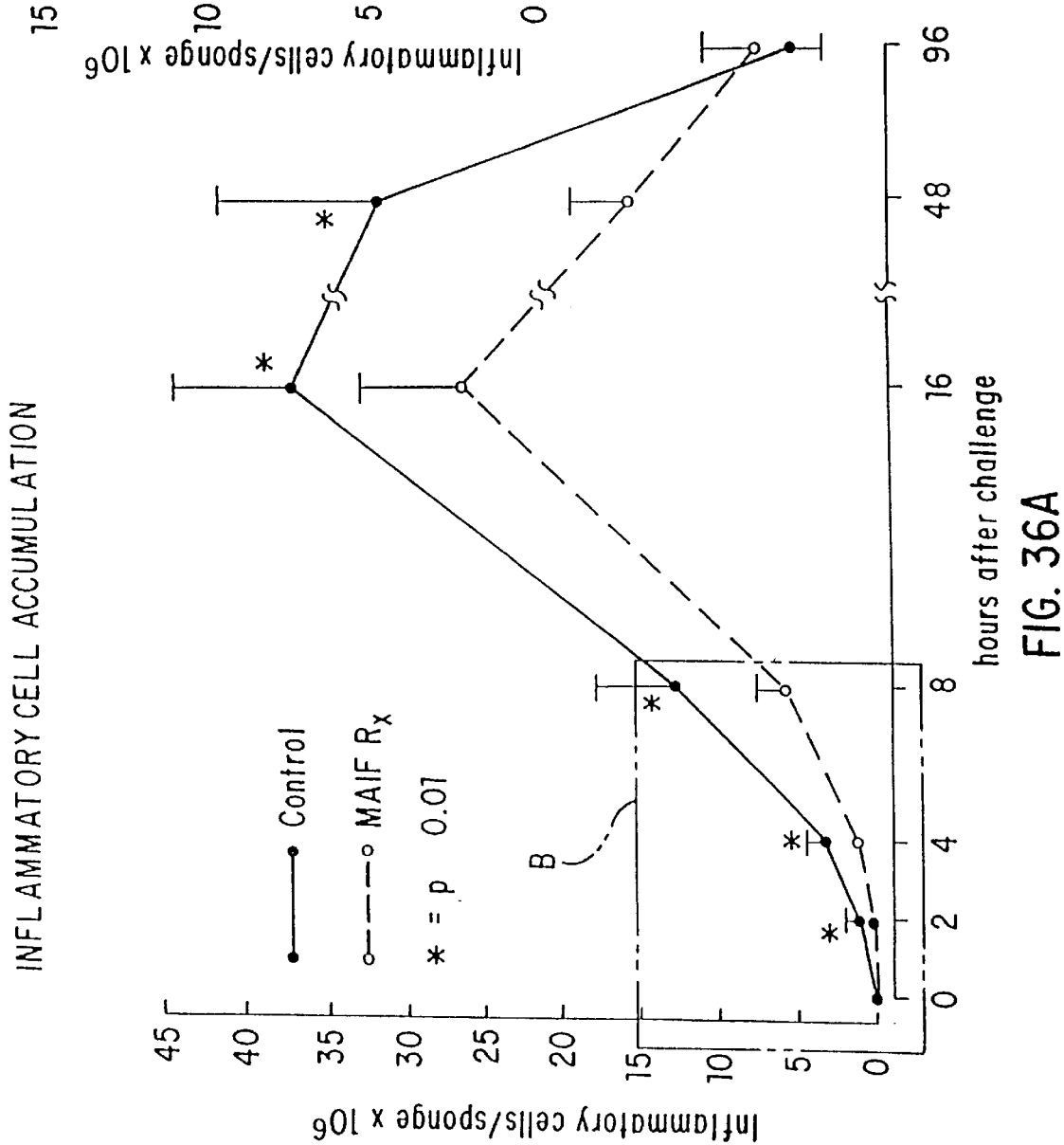
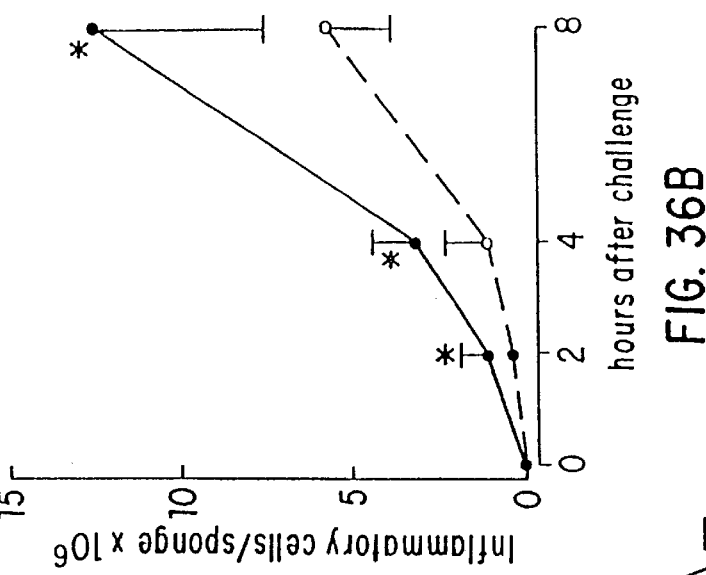
FIG. 36A
FIG. 36B

PEAK 12

PEAK 12

ANTI-INFLAMMATORY FACTOR, METHOD OF ISOLATION, AND USE

This application is a continuation-in-part of U.S. patent application Ser. No. 08/316,474, filed Oct. 3, 1994 (U.S. Pat. No. 5,650,175, issued Jul. 22, 1997) which is fully incorporated herein by reference.

BACKGROUND OF THE INVENTION

1. Field of the Invention

The present invention relates to an anti-inflammatory factor, processes for its production in substantially pure or highly pure form, and a method for its use in the treatment of inflammation.

2. Description of the Background Art

Inflammation, as defined in Dorland's Medical Dictionary, is "a localized protective response elicited by injury or destruction of tissues which serves to destroy, dilute or wall off both the injurious agent and the injured tissue." It is characterized by fenestration of the microvasculature, leakages of the elements of blood into the interstitial spaces, and migration of leukocytes into the inflamed tissue. On a macroscopic level, this is usually accompanied by the familiar clinical signs of erythema, edema, tenderness (hyperalgesia), and pain. During this complex response, chemical mediators such as histamine, 5-hydroxytryptamine, various chemotactic factors, bradykinin, leukotrienes, and prostaglandins are liberated locally. Phagocytic cells migrate into the area, and cellular lysosomal membranes may be ruptured, releasing lytic enzymes. All of these events may contribute to the inflammatory response.

Inflammation in patients with rheumatoid arthritis probably involves the combination of an antigen (gamma globulin) with an antibody (rheumatoid factor) and complement causing the local release of chemotactic factors that attract leukocytes. The leukocytes phagocytose the complexes of antigen-antibody and complement and also release the many enzymes contained in their lysosomes. These lysosomal enzymes then cause injury to cartilage and other tissues, and this furthers the degree of inflammation. Cell-mediated immune reactions may also be involved. Prostaglandins are also released during this process.

Prostaglandins, which are likely to be generated in inflammation, cause erythema and increase local blood flow. Two important vascular effects of prostaglandins are not generally shared by other mediators of inflammation—a long-lasting vasodilator action and a capacity to counteract the vasoconstrictor effects of substances such as norepinephrine and angiotensin.

A number of mediators of inflammation increase vascular permeability (leakage) in the post-capillary and collecting venules. In addition, migration of leukocytes into an inflamed area is an important aspect of the inflammatory process.

The Arthus reaction is an inflammatory response brought about by the formation of immune complexes at subcutaneous sites where an antigen complexes with antibody to that antigen. Neutrophils characteristically attach to the Fc portion of the immunoglobulin complex that forms at the subcutaneous injection site where they release digestive enzymes, causing visible acute inflammation. Thus the reaction is primarily neutrophil-mediated and agents that effect the development of the reaction do so via an effect on these cells.

There are several pathways whereby an agent might interfere with neutrophil migration from the blood vessels to an inflammatory site. One likely pathway is the inhibition of margination, the reversible "sticking" of inflammatory cells to the endothelial cell lining of the blood vessel wall. In the normal state about 50% of neutrophils are reversibly adhered, but during an acute inflammatory response, adhesion becomes much stronger and is a key step in the process of neutrophil migration. While prostaglandins are unlikely to be directly involved in the chemotactic response, another product of the metabolism of arachidonic acid, leukotriene, is a very potent chemotactic substance.

The anti-inflammatory response is any response characterized by inflammation as defined above. It is well known to those skilled in the medical arts that the inflammatory response causes much of the physical discomfort, i.e., pain and loss of function, that has come to be associated with different diseases and injuries. Accordingly, it is a common medical practice to administer pharmacological agents which have the effect of neutralizing the inflammatory response. Agents having these properties are classified as anti-inflammatory drugs. Anti-inflammatory drugs are used for the treatment of a wide spectrum of disorders, and the same drugs are often used to treat different diseases. Treatment with anti-inflammatory drugs is not for the disease, but most often for the symptom, i.e., inflammation.

The anti-inflammatory, analgesic, and anti-pyretic drugs are a heterogeneous group of compounds, often chemically unrelated, which nevertheless share certain therapeutic actions and side-effects. Corticosteroids represent the most widely used class of compounds for the treatment of the anti-inflammatory response. Proteolytic enzymes represent another class of compounds which are thought to have anti-inflammatory effects. Hormones which directly or indirectly cause the adrenal cortex to produce and secrete steroids represent another class of anti-inflammatory compounds. A number of non-hormonal anti-inflammatory agents have been described. Among these, the most widely used are the salicylates. Acetylsalicylic acid, or aspirin, is the most widely prescribed analgesic-antipyretic and anti-inflammatory agent. Examples of steroidal and non-steroidal anti-inflammatory agents are listed in the *Physician's Desk Reference*, 1987 (see pp. 207 and 208 for an index of such preparations).

The natural and synthetic corticosteroid preparations cause a number of severe side effects, including elevation of blood pressure, salt and water retention, and increased potassium and calcium excretion. Moreover, corticosteroids may mask the signs of infection and enhance dissemination of infectious microorganisms. These hormones are not considered safe for use in pregnant women, and long-term corticosteroid treatment has been associated with gastric hyperactivity and/or peptic ulcers. Treatment with these compounds may also aggravate diabetes mellitus, requiring higher doses of insulin, and may produce psychotic disorders. Hormonal anti-inflammatory agents which indirectly increase the production of endogenous corticosteroids have the same potential for adverse side-effects.

The non-hormonal anti-inflammatory agents are synthetic biochemical compounds which can be toxic at high doses with a wide spectrum of undesirable side-effects. For example, salicylates contribute to the serious acid-base balance disturbances that characterize poisoning by this class of compounds. Salicylates stimulate respiration directly and indirectly. Toxic doses of salicylates cause central respiratory paralysis as well as circulatory collapse secondary to vasomotor depression. The ingestion of salicylate may result in epigastric distress, nausea, and vomiting. Salicylate-induced gastric bleeding is well known. Salicylates can produce hepatic injury, and lead to a prolongation of clotting time. Therefore, aspirin should be avoided in patients with severe hepatic damage, hypoprothrombinemia, vitamin K deficiency, or hemophilia, because the inhibition of platelet hemostasis by salicylates can result in hemorrhage. Salicylate intoxication is common, and over 10,000 cases of serious salicylate intoxication are seen in the United States every year, some of them being fatal, and many occurring in children. See Goodman and Gilman's *The Pharmacological Basis of Therapeutics,* 7th Ed., 1985. Accordingly, in spite of the large number of anti-inflammatory agents that are currently available, there still exists a need for a safe, effective anti-inflammatory product which is free of side-effects and adverse reactions.

If a natural food product, such as one derived from milk, for example, could be obtained having anti-inflammatory effects, it would be an easily administrable, readily available, safe therapeutic composition.

It has been known in the prior art to produce milks having a variety of therapeutic effects. Beck, for example, has disclosed a milk containing antibody to *Streptococcus mutans* that has dental caries inhibiting effect (U.S. Pat. No. 4,324,782). The milk is obtained by immunizing a cow with *S. mutans* antigen in two stages and obtaining the therapeutic milk therefrom.

Stolle et al. have disclosed a method for treating vascular disorders or pulmonary disorders associated with smoking in an animal which comprises administering to the animal milk collected from a cow being maintained in a hyperimmune state (U.S. Pat. No. 4,636,384). Beck has disclosed a method for treating inflammation in an animal which comprises administering to the animal an anti-inflammatory effective amount of milk collected from a cow maintained in an anti-inflammatory factor producing state (U.S. Pat. No. 4,284,623). Heinbach, U.S. Pat. No. 3,128,230, has described milk containing globulins of alpha, beta, and gamma components by inoculating a cow with antigenic mixtures. Peterson et al. U.S. Pat. No. 3,376,198), Holm (U.S. application (published) Ser. No. 628,987), Tunnah et al. (British Patent No. 1,211,876) and Biokema S. A. (British Patent 1,442,283) have also described antibody-containing milks.

None of the aforementioned references, however, disclose the identity of the component or components of therapeutic milks which produce the desired therapeutic effects. For example, in Beck, U.S. Pat. No. 4,284,623, the milk products used as a therapeutic means consist of either fluid whole milk, fluid fat-free whey, or whole milk powders. Although each of these milk products has anti-inflammatory properties, the factor or factors that actually provide the therapeutic benefits have not yet been isolated or identified or purified to homogeneity.

A particular difficulty in obtaining highly purified preparations of milk anti-inflammatory factor(s) (MAIF) is the inability to remove tightly bound salts from the MAIF by currently used purification procedures. One of the problems that this invention addresses, inter alia, is the large scale preparation of MAIF including the elimination of tightly bound salts from the MAIF preparation, thereby resulting in highly purified MAIF. Further, problems have previously arisen in obtaining highly pure, preparative scale preparations of MAIF when beginning with large volumes of starting materials (e.g. 90 liters of skim milk). The invention provides solutions to these problems.

SUMMARY OF THE INVENTION

The present invention is directed to an anti-inflammatory factor present in milk and various methods involving the use of the anti-inflammatory factor present in milk. Specifically, the invention is directed to an anti-inflammatory factor produced from milk by removing the fat from the milk; filtering the milk so as to remove molecules with molecular weights greater than about 10,000 daltons; fractionating the filtrate containing small molecular weight molecules by ion-exchange; further enriching ion-exchange fractions in the factor by gel filtration and further enriching gel filtration fractions by affinity chromatography using a chromatography medium with an affinity for coplanar adjacent cis hydroxyl groups.

The invention is further directed to methods for additional purification of the milk anti-inflammatory factor using, inter alia, HPLC size exclusion chromatography and organic partition extraction protocols.

In an alternative embodiment, the present invention is directed to a method for obtaining an anti-inflammatory factor from skimmed milk comprising the steps of: (i) ultrafiltering the skimmed milk through a filter with a molecular weight cut-off of 1,000 daltons; (ii) collecting the <1,000 dalton permeate from step (i); (iii) extracting the permeate from step (ii) by organic partition extraction and obtaining the aqueous extract from the extraction; (iv) separating the aqueous extract from step (iii) by reversed-phase HPLC chromatography; and (v) collecting the eluate. This embodiment is particularly appropriate for large-scale preparation of milk anti-inflammatory factor in quantities suitable for handling, transportation, storage, and processing.

In a preferred embodiment, the skimmed milk is hyperimmune skimmed milk.

In a particularly preferred embodiment, the hyperimmune skimmed milk is whey.

In another preferred embodiment, the organic partition extraction further comprises: (i) extracting with hexane and $NH_4OH$; (ii) reextracting the aqueous phase from step (i) with ethyl acetate; and (iii) collecting said ethyl acetate extract.

In another preferred embodiment, the reversed-phase HPLC chromatography column is a Zorbax SB-$C_{18}$ column.

In an alternative embodiment, the present invention is directed to an anti-inflammatory factor in highly purified form produced by a process comprising: (i) ultrafiltering skimmed milk through a filter with a molecular weight cut-off of 1,000 daltons; (ii) collecting the <1,000 dalton permeate from step (i); (iii) extracting the permeate from step (ii) by organic partition extraction and obtaining the aqueous extract from the extraction; (iv) separating the aqueous extract from step (iii) by reversed phase HPLC chromatography; and (v) collecting the eluate.

In a preferred embodiment, the skimmed milk is hyperimmune skimmed milk.

In a particularly preferred embodiment, the hyperimmune skimmed milk is whey.

In another preferred embodiment, the organic partition extraction further comprises: (i) extracting with hexane and $NH_4OH$; (ii) reextracting the aqueous phase from step (i) with ethyl acetate; and (iii) collecting said ethyl acetate extract.

In another preferred embodiment, the reversed-phase HPLC chromatography column is a Zorbax SB-$C_{18}$ column.

It is understood that throughout this disclosure, wherever the term "skimmed milk" is used, the terms "milk" or "whole milk" may be substituted.

The invention is further directed to methods for using a milk anti-inflammatory factor, including a milk anti-inflammatory factor produced by any of the above alternative embodiments, to prevent neutrophils from adhering to the endothelium of venules or to detach neutrophils which have already adhered to the endothelial cells lining the walls of venules. In this way, the factor is used to reduce the tissue damage associated with the inflammatory response.

The invention is also directed to a method for using a milk anti-inflammatory factor, including the milk anti-inflammatory factor of any of the above alternative embodiments to prevent interactions between CD18 cell-surface antigens and other molecules. It is known that such interactions are necessary for the exit of cells from the vasculature and that such emigration leads to increased tissue damage in animals during the inflammatory response. CD18 antigens are also known to be important in the immunological response of a host organism to foreign antigens.

Also encompassed by the invention is the use of a anti-inflammatory factor, including the anti-inflammatory factor of any of the above alternative embodiments, in mammals to prevent the emigration of cells from the vasculature and to suppress the mitogenic response of lymphocytes to foreign antigens.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 20. Effect of 20 mg of MAIF injected i.v. on the reverse passive Arthus reaction. *=p<0.01;**=p<0.05.

FIG. 33 (A–E). Effect of anti-inflammatory factor on various aspects of lymphocyte function. 33a shows the effect of prior administration of factor on the response of host T lymphocytes to foreign histocompatibility antigens. 33b shows the results obtained when lymphocytes from MAIF treated rats are injected into untreated rats. 33C and 33D show the effect of MAIF treatment on spleen weight and spleen cell number in rats. 33E shows the effect of MAIF treatment on the concanavalin A stimulated mitogenic response of lymphocytes.

FIG. 36(A–B). Inhibition of inflammatory cell infiltration into infected sponges by MAIF (40 mg per rat, i.v.).

DETAILED DESCRIPTION OF THE PREFERRED EMBODIMENTS

Figure 1:
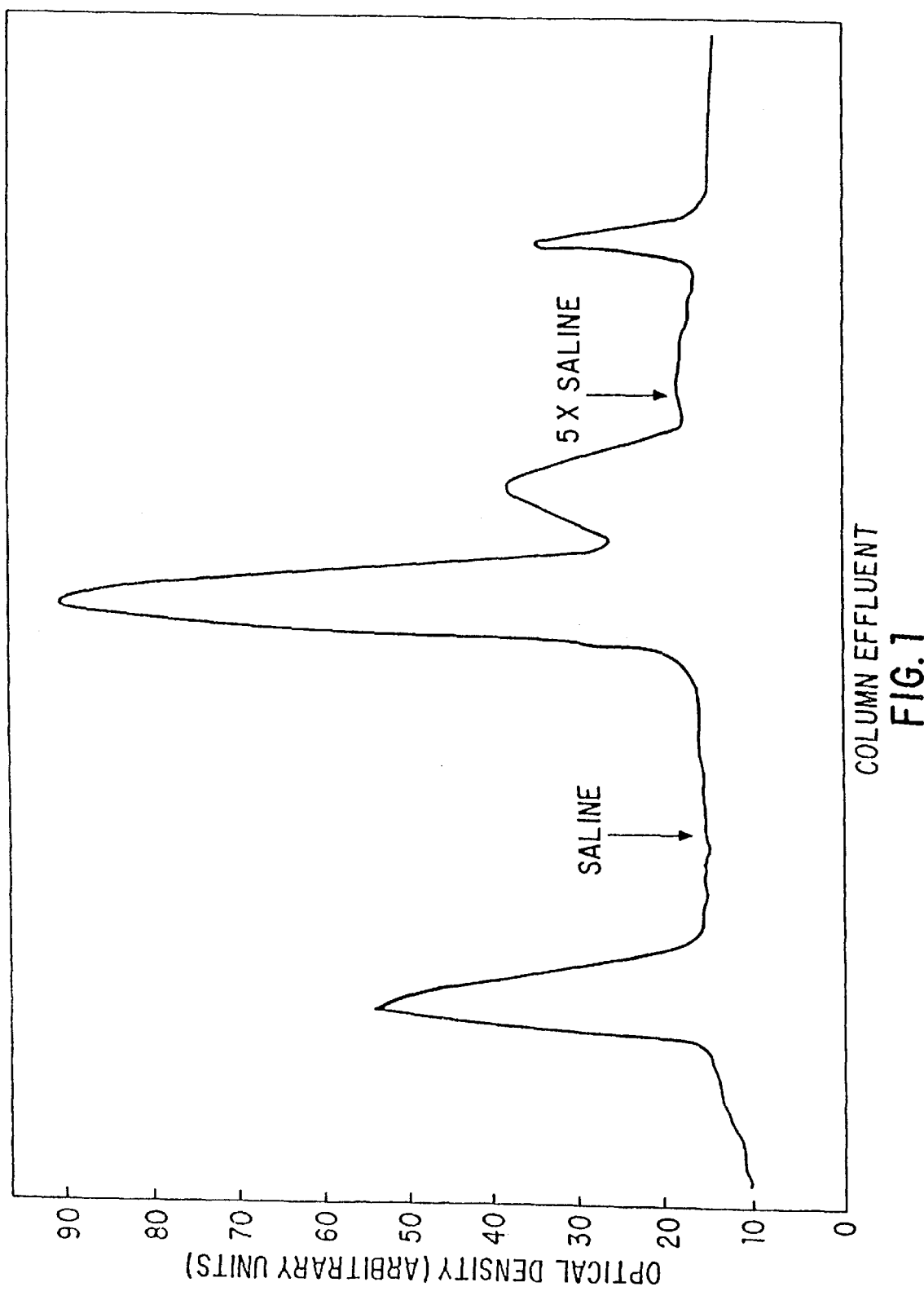
FIG. 1. Isolation of the anti-inflammatory factor by ion-exchange chromatography on a column of DEAE-cellulose.

The invention comprises the isolation and purification of an anti-inflammatory factor from milk and the administration of said factor to an animal for the purpose of treating anti-inflammatory disorders. Except as otherwise indicted, the following definitions apply:

By the term "milk anti-inflammatory factor" is intended a factor obtained from either hyperimmune milk or normal cow's milk. By the term "substantially pure milk anti-inflammatory factor" is intended, for the purpose of this invention, an anti-inflammatory factor that elutes as a single major symmetrical peak on HPLC chromatography, after removal of high molecular weight substances (>10,000 daltons) and isolation of the low molecular weight, negatively-charged species by ion-exchange chromatography. By the term "substantially pure milk anti-inflammatory factor" is also intended anti-inflammatory factor in highly purified form produced by a process comprising: (i) ultra-filtering skimmed milk through a filter with a molecular weight cut-off of 1,000 daltons; (ii) collecting the <1,000 dalton permeate from step (i); (iii) extracting the permeate from step (ii) by organic partition extraction and obtaining the aqueous extract from the extraction; (iv) separating the aqueous extract from step (iii) by reversed phase HPLC chromatography; and (v) collecting the eluate. By the term "highly purified" or "highly pure" is intended an anti-inflammatory factor which has an elution pattern similar, though not necessarily identical to that of FIG. 44, on a reversed-phase HPLC chromatography column. Both normal milk and hyperimmune milk can be processed by the methods described herein to obtain the anti-inflammatory factor.

By the term "hyperimmune milk" is intended, for the purpose of this invention, milk obtained from milk-producing animals maintained in a hyperimmune state, the details for hyperimmunization being described in greater detail below.

By the term "whey" is intended, for the purpose of this invention, milk from which cream has been removed.

By the term "normal milk" is intended for the purpose of the invention milk that is obtained from milk-producing animals by conventional means and dairy practices.

By the term "milk-producing animal" is intended, for the purpose of this invention, mammals that produce milk in commercially feasible quantities, preferably cows, sheep and goats, more preferably dairy cows of the genus $Bos$ (bovid), particularly those breeds giving the highest yields of milk, such as Holstein.

By the term "bacterial antigen" is intended, for the purpose of this invention, a lyophilized preparation of heat-killed bacterial cells.

By the term "microencapsulated form" is intended, for the purpose of this invention, polymeric microparticles encapsulating one or more bacterial antigens for administration to milk-producing animals.

By the term "inflammation" is intended, for the purpose of this invention, a localized protective response elicited by injury or destruction of tissues which serves to destroy, dilute or wall off both the injurious agent and the injured tissue, characterized in the acute form by the classical sequence of pain, heat, redness, swelling, and loss of function, and histologically involving a complex series of events, including dilatation of the arterioles, capillaries, and venules with increased permeability and blood flow, exudation of fluids including plasma proteins, and leukocyte migration into the inflammatory focus.

By the term "treating" is intended, for the purposes of this invention, that the symptoms of the disorder and/or pathogenic origin of the disorder be ameliorated or completely eliminated.

By the term "administer" is intended, for the purpose of this invention, any method of treating a subject with a substance, such as orally, intranasally, parenterally (intravenously, intramuscularly, or subcutaneously), or rectally.

By the term "animal" is intended, for the purpose of this invention, any living creature that is subject to inflammation, including humans, farm animals, domestic animals, or zoological garden animals.

Examples of inflammatory conditions that may be treated by the isolated and purified milk product of the present invention are conditions selected from the group consisting of acute and subacute bursitis, acute non-specific tendinitis, systemic lupus erythematosus, systemic dermatomyositis, acute rheumatic carditis, pemphigus, bullous dermatitis, herpeteformis, severe erythema, multiform exfoliative dermatitis, cirrhosis, seasonal perennial rhinitis, bronchial asthma, ectopic dermatitis, serum sickness, keratitis, opthalmicus iritis, diffuse ureitis, chorditis, optic neuritis, sympathetic ophthalmia, symptomatic sarcoidosis, Loeffler's syndrome, berylliosis, hemolytic anemia, mastitis, mastoiditis, contact dermatitis, allergic conjunctivitis, psoriatic arthritis, ankylosing spondylitis, acute gouty arthritis, and herpes zoster. Further, the isolated and purified milk product may be used to treat individuals who are exposed to potentially inflammatory agents.

The invention is based in part on the discovery that when a milk-producing animal such as a bovid is brought to a specific state of hyperimmunization, the animal will produce milk which has supranormal levels of the highly beneficial anti-inflammatory factor, said factor not only suppressing the symptoms of inflammation in man and other animals, but also being a prophylactic agent in anticipation of the presence of inflammatory agents in the recipient. By the term "supranormal levels" is intended levels in excess of that found in milk from non-hyperimmunized animals. The induction of immune sensitivity alone is insufficient to cause the appearance of supranormal levels of MAIF in milk, as is shown by the fact that normal cow's milk does not contain these supranormal levels, even though the cows have become sensitized against various antigens during normal immunization against cow diseases and during normal exposure to the environment. It is only in specific hyperimmune states that the milk has the desired supranormal levels.

This special state may be achieved by administering an initial immunization, followed by periodic boosters with sufficiently high doses of specific antigens. The preferred dosage of booster should be equal to or greater than 50% of the dosage necessary to produce primary immunization of the bovid. Thus, there is a threshold booster dosage below which the properties are not produced in the milk, even though the cow is in what normally would be called an immune state. In order to achieve the requisite hyperimmune state, it is essential to test the hyperimmune milk after a first series of booster administrations. If the beneficial factors are not present in the milk, additional boosters of high dosage are administered until the properties appear in the milk.

The process of producing the hyperimmune milk containing supranormal levels of anti-inflammatory factor is disclosed in co-pending U.S. patent application Ser. No. 580,382, filed Sep. 11, 1990 and also in U.S. Ser. No. 355,786, filed May 22, 1989 (now U.S. Pat. No. 5,106,618, a file wrapper continuation of U.S. Ser. No. 069,139, filed Jul. 2, 1987) and in U.S. Ser. No. 910,297, filed Sep. 17, 1986 (now U.S. Pat. No. 4,919,929, a file wrapper continuation of U.S. Ser. No. 576,001, filed Feb. 1, 1983), all of which are incorporated herein by reference in their entirety. In summary, one process of producing the hyperimmune milk containing supranormal levels of anti-inflammatory factor comprises the following steps: (1) antigen selection; (2) primary immunization of the bovid; (3) testing the serum to confirm sensitivity induction; (4) hyperimmunization with boosters of appropriate dosage; and, optionally, (5) testing the milk for anti-inflammatory properties; (6) collecting the milk from the hyperimmune bovid; and (7) processing the milk to isolate the MAIF.

Step 1: Any antigens or combination of antigens may be employed. The antigens can be bacterial, viral, protozoan, fungal, cellular, or any other substances to which the immune system of a milk-producing animal will respond. The critical point in this step is that the antigen(s) must be capable, not only of inducing immune and hyperimmune states in the milk-producing animal, but also of producing supranormal levels of anti-inflammatory factor in the milk. Any antigen can be used to produce supranormal levels of factor. One preferred vaccine is a mixture of polyvalent bacterial antigens, referred to as Series 100 vaccine, described in detail in Example 1A below.

Step 2: The antigen(s) can be administered in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppository, or oral administration may be used.

Step 3: It is necessary to determine whether or not the milk-producing animal has become sensitive to the antigen. There are a number of methods known to those skilled in the art of immunology to test for sensitivity (*Methods in Immunology and Immunochemistry*, William, C. A., and Chase, W. M., Academic Press, New York, vols. 1–5 (1975)). The preferred method is to use a polyvalent vaccine comprising multiple bacterial species as the antigen and to test for the presence of agglutinating antibodies in the serum of the animal before and after challenge with the vaccine. The appearance of milk antibodies after immunization with the vaccine indicates sensitivity; at this point it is possible to proceed to step 4.

Step 4: This involves the induction and maintenance of the hyperimmune state in the sensitized animal. This is accomplished by repeated booster administration at fixed time intervals of the same polyvalent vaccine that was used to achieve the primary sensitization. A two-week booster interval is optimal for polyvalent bacterial antigens. However, it is necessary to ensure that the animal does not pass from a hyperimmune state to a state of immune tolerance to the antigen.

In a preferred embodiment, hyperimmunization of bovids may be achieved by a single administration of microencapsulated vaccine, prepared as described in detail in Example 1B below. The advantage of the controlled release form of hyperimmunization is that the constant exposure to the antigen ensures that the animal remains in the hyperimmune state.

In an alternative embodiment, it is also possible to combine different immunization procedures, e.g., simultaneously administering microencapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the milk for anti-inflammatory activity levels. This can be accomplished by any research technique that tests the effects of either the hyperimmune milk or products derived therefrom upon inflammation. Chemical-induced inflammation of the rat paw is a standard assay for anti-inflammatory drugs.

Step 6: This involves the collection and processing of the milk. The milk can be collected by conventional methods. Processing the milk to isolate the anti-inflammatory factor is described below.

The simplest process for isolating, purifying and testing the anti-inflammatory factor comprises the following steps:

1. defatting the hyperimmune milk to produce skim milk;
2. removing casein from skim milk to produce whey;
3. removal from the whey macromolecules of molecular weight greater than about 10,000 daltons by ultrafiltration;
4. fractionating the product from step 3 using an ion-exchange resin column to isolate a negatively-charged anti-inflammatory species of molecular weight less than about 10,000 daltons;
5. separating the negatively-charged species from step 4 by molecular sieve chromatography; and
6. biological assay of the anti-inflammatory factor preparation from step 5.

In an alternative preferred embodiment, the fractions from molecular sieve chromatography that have biological activity are further purified by filtration through a membrane that retains macromolecules of molecular weight greater than about 5000 daltons.

Another preferred embodiment further comprises additional purification of the MAIF by HPLC size exclusion chromatography and organic partition extraction.

Yet another preferred embodiment of the present invention comprises the purification of anti-inflammatory factor in highly purified form produced by a process comprising: (i) ultrafiltering skimmed milk through a filter with a molecular weight cut-off of 1,000 daltons; (ii) collecting the <1,000 dalton permeate from step (i); (iii) extracting the permeate from step (ii) by organic partition extraction and obtaining the aqueous extract from the extraction; (iv) separating the aqueous extract from step (iii) by reversed phase HPLC chromatography; and (v) collecting the eluate 7. The anti-inflammatory action of the milk factor is tested on edema that is caused by the injection of a solution of carrageenan into the paw of rats. The rat paw test is the standard animal test for anti-inflammatory drugs. Winter, C. A., Risley, G. A., Nuss, A. W., "Carrageenan-Induced Edema in the Hind Paw of the Rat as an Assay for Anti-inflammatory Drugs," *Proc. Soc. Exper. Biol. Med.* 3:544 (1967). Alternatively, one can use a pleural neutrophil migration inhibition assay or tumor necrosis factor induction assay as described in Example 24. Vinegar et al., "Some Quantitative Characteristics of Carrageenan-induced Pleurisy in the Rat," *Proc. Soc. Exp. Biol. Med.* 143: 711–714 (1973); Ammendola, G. et al. "Leukocyte Migration and Lysozomal Enzymes Release in Rat Carrageenan Pleurisy," *Agents and Actions* 5: 250–255 (1975); Vinegar, R. et al. "Quantitative Studies of the Pathway to Acute Carrageenan Inflammation.". *Fed. Proc.* 35:2447–2456 (1976). A variety of other tests may be used. Wetnick, A. S., and Sabin, C., "The Effects of Clonixin and Bethaurethasone on Adjuvant-Induced Arthritis and Experimental Allergic Encephalomyelitis in Rats," *Jap. J Pharm.* 22:741 (1972). However, the rat paw test is the most simple and direct test available, and has been shown to be satisfactory for all anti-inflammatory drugs. This test has been described in detail in Beck, U.S. Pat. No. 4,284,623, which is incorporated herein by reference to the extent that it describes the rat paw test. Briefly, the test involves the injection of a small quantity of carrageenan into the footpad of adult white rats. This is known to induce an inflammatory response. The resulting degree of swelling can be quantified. Samples containing an anti-inflammatory factor are administered to the rat by a suitable route, preferably by intraperitoneal injection, and the blockade or amelioration of the inflammatory process quantified by either volumetric or gravimetric methods.

In summary, one can isolate the anti-inflammatory factor from hyperimmunized milk by following a process of defatting the milk, removing casein, removing macromolecules of greater than 10,000 daltons, and continuing with ion exchange and molecular sieve chromatography. The biological activity of appropriate preparations of anti-inflammatory factor can be tested by doing a dose-response experiment on rats as described herein.

In an additional preferred embodiment of the present invention, the anti-inflammatory factor present in hyperimmunized milk is purified using a combination of steps involving: filtration on a membrane capable of separating molecules based upon their molecular weights; ion-exchange chromatography; molecular sieve chromatography; and affinity chromatography (Example 15).

The preferred first step comprises filtering hyperimmune skim milk, produced as described above, through a membrane which retains molecules with molecular weights of about 10,000 daltons or more. The material passed by the membrane (i.e. the filtrate or permeate) is collected and used in further purification steps. Devices and membranes for performing such filtrations are well-known in the art.

The preferred step following filtration is ion-exchange chromatography on a anion exchanger. Exchangers having diethylaminoethyl groups have been found to effectuate good separations but it is expected that other anion exchangers could be used as well. It is preferred that the solid support of the ion-exchanger be capable of maintaining high flow rates. Sepharose has been found to be suitable for this purpose.

The preferred step after ion-exchange chromatography is gel filtration chromatography. A column packing for this step should be chosen which is capable of fractionating molecules with molecular weights of less than 10,000 daltons. The preferred packing is Toyopearl HW-40 (Rohm and Haas) but other packings well known in the art could be used as well. Examples of other packings that could be used and which are commercially available are polymeric carbohydrate based packings, e.g. Sephadex G-10 or G-25 (Pharmacia), or polyacrylamide based packings, e.g. Biogel P-2, P-4, P-6, P-10 or P-30, (Bio-Rad).

The preferred step after gel filtration chromatography is affinity chromatography on a boronate affinity support. These supports have been found to be effective at fractionating low molecular weight compounds with cis-diol groups. The preferred support is AffiGel 601 (Bio-Rad). This is a boronate derivative of the polyacrylamide gel filtration support Bio-Gel P-6 (also sold by Bio-Rad).

The preferred mode of storage for preparations after the ion exchange, gel filtration or affinity chromatography steps is as a lyophilized powder. The filtrate collected in the first purification step may be stored refrigerated until use. The activity of the anti-inflammatory factor resulting from the purification may be determined using the rat paw test described above.

In another preferred embodiment of the present invention, the anti-inflammatory factor present in hyperimmunized milk is analytically or preparative purified using a combination of steps involving: ultrafiltrationion with a membrane having a molecular weight cutoff of 10,000 daltons, ion exchange chromatography, size exclusion chromatography on a preparative HPLC column and organic partition extraction.

In a preferred first step, a large volume (e.g. 90 liter of skimmed milk is passed through an ultrafiltration membrane with a 10,000 dalton cutoff. The resulting permeate (<10K permeate) is collected for further purification steps.

The preferred step following the above ultrafiltration is applying a large volume (e.g. 60 liters) of permeate from the previous step to an ion exchange column. The eluate can then be lyophilized.Diethyl-aminoethyl (DEAE)-Sepharose Fast Flow exchange resin has been found to effectuate good separation.

The preferred step after the above ion-exchange chromatography is placing on a preparative HPLC column a large quantity (e.g. 100 mg.) of the purified preparation from the ion-exchange column. Even larger quantities can be obtained by separating multiple samples of 100 mg each on the HPLC column and collecting them into the same set of tubes. The tubes can then be pooled and their contents lyophilized.

The next preferred step is organic partition extraction which entails taking 50–100 mg. of the lyophilized HPLC column samples and extracting with n-hexane to remove neutral lipids, acidification and then reextraction with ethyl acetate.

In another preferred embodiment of the present invention, anti-inflammatory factor is purified by a process comprising: (i) ultrafiltering skimmed milk through a filter with a molecular weight cut-off of 1,000 daltons; (ii) collecting the <1,000 dalton permeate from step (i); (iii) extracting the permeate from step (ii) by organic partition extraction and obtaining the aqueous extract from the extraction; (iv) separating the aqueous extract from step (iii) by reversed phase HPLC chromatography; and (v) collecting the eluate.

In a preferred step (i), the skimmed milk is in the form of hyperimmune skimmed milk whey.

In a preferred step (ii), the organic partition extraction further comprises: (i) extracting with hexane and $NH_4OH$; (ii) reextracting the aqueous phase from step (i) with ethyl acetate; and (iii) collecting said ethyl acetate extract.

In a preferred step (iii), the reversed-phase HPLC chromatography column is a Zorbax SB-$C_{18}$ column.

Results of experiments described in Example 16 indicate that pretreatment of animals with preparations of anti-inflammatory factor reduces the platelet activating factor (PAF) stimulated adhesion of neutrophils to the endothelial cells which line venules and reduces the rate at which neutrophils emigrate from venules. In addition, the administration of preparations of the factor after treatment of animals with PAF was found to reduce the number of neutrophils adhering to endothelial cells. To the extent that patients or animals may benefit from these effects, the present invention encompasses the use of preparations of the anti-inflammatory factor. This is true regardless of the particular disease involved. Similarly, the data in Example 16 indicates that the anti-inflammatory factor causes its effects on adhesion and emigration by interacting directly with cell-surface CD18 antigens and preventing other molecules from interacting with this glycoprotein complex. The present invention encompasses the use of preparations of the anti-inflammatory factor for this purpose as well.

A shown in Example 18, the administration of a preparation of anti-inflammatory factor to animals suppresses the Host vs. Graft but not the Graft vs. Host reaction and causes an increase in spleen weight and in the number of splenic lymphocytes. The lymphocyte response to Concanavalin A was also found to be abrogated by the preparation. These data indicate that the anti-inflammatory factor is useful in the inhibition of tissue destructive infectious processes, and in situations where suppression of lymphocyte function is desirable.

Figure 42:
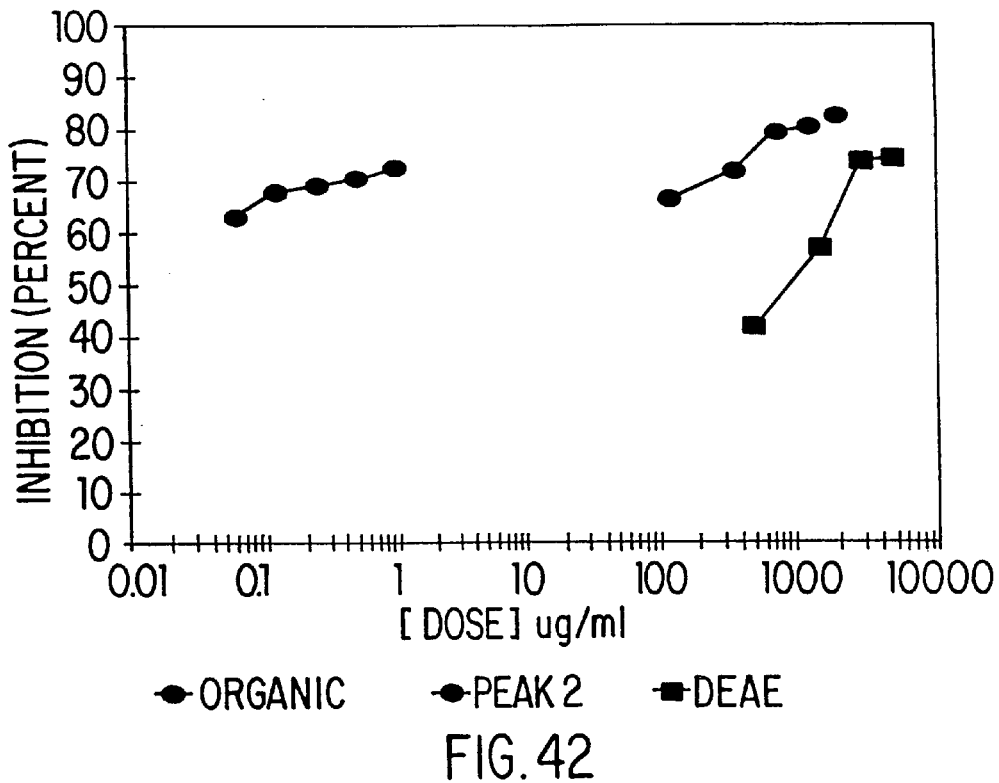
FIG. 42. Analysis of the dried ethyl acetate fraction in the neutrophil migration inhibition assay compared to MAIF obtained prior to the organic partition extraction. The dried ethyl acetate fraction demonstrated strong MAIF activity.

As shown in FIG. 42, desalting of the MAIF (obtained by organic partition extraction) results in dramatic increases in purification as indicated by as much as a 10,000 fold lower dose of MAIF being required to obtain similiar levels of migration inhibition of rat pleural leukocytes.

Accordingly, the present invention is also directed to methods for using a milk anti-inflammatory factor, including a milk anti-inflammatory factor produced by any of the above alternative embodiments, to prevent neutrophils from adhering to the endothelium of venules or to detach neutrophils which have already adhered to the endothelial cells lining the walls of venules. In this way, the factor is used to reduce the tissue damage associated with the inflammatory response.

The invention is also directed to a method for using a milk anti-inflammatory factor, including the milk anti-inflammatory factor of any of the above alternative embodiments to prevent interactions between CD18 cell-surface antigens and other molecules. It is known that such interactions are necessary for the exit of cells from the vasculature and that such emigration leads to increased tissue damage in animals during the inflammatory response. CD18 antigens are also known to be important in the immunological response of a host organism to foreign antigens.

Also encompassed by the invention is the use of a anti-inflammatory factor, including the anti-inflammatory factor of any of the above alternative embodiments, in mammals to prevent the emigration of cells from the vasculature and to suppress the mitogenic response of lymphocytes to foreign antigens.

The compositions of the present invention may be administered by any means that provide anti-inflammatory activity. For example, administration may be parenteral, subcutaneous, intravenous, intramuscular, intraperitoneal or oral.

Solid dosage forms for oral administration include capsules, tablets, pills, powders and granules. In such solid dosage forms the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixirs containing inert diluents commonly used in the pharmaceutical art. Besides inert diluents, such compositions can also include adjuvants, such as wetting agents, emulsifying and suspending agents, and sweetening.

Preparations according to this invention for parenteral administration include sterile aqueous or nonaqueous solutions, suspensions or emulsions. Examples of nonaqueous solvents or vehicles are propylene glycol, polyethylene glycol, vegetable oils such as olive oil and injectable organic esters such as ethyl oleate.

The dosage of active ingredients in the composition of this invention may be varied; however it is necessary that the amount of the active ingredient shall be such that a suitable dosage form is obtained. The selected dosage form depends upon the desired therapeutic effect, on the route of the administration and on the duration of the treatment.

Administration dosage and frequency will depend on the age and general health condition of the patient, taking into consideration the possibility of side effects. Administration will also be dependent on concurrent treatment with other drugs and patients tolerance of the administered drug.

Having now described the invention in general terms, the same will be further described by reference to certain specific examples that are provided herein for purposes of explanation only, and are not intended to be limiting unless otherwise specified.

EXAMPLE 1A

Preparation of S-100 Vaccine

A bacterial culture containing the spectrum of bacteria shown in Table 1 below as obtained from the American Type Culture Collection was reconstituted with 15 ml of media and incubated overnight at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet obtained upon centrifugation was resuspended in a small amount of double distilled water.

The media-free bacterial suspension was heat-killed by placing the suspension in a glass flask in an 80° C. water bath overnight. The viability of the broth culture was tested with a small amount of heat-killed bacteria. Broth was inoculated with heat-killed bacteria, incubated at 37° C. for five days and checked daily for growth, as the bacteria have to be killed for use in the vaccine.

The heat-killed bacteria were lyophilized until dry. The dry bacteria were then mixed with sterile saline solution to a concentration of $2.2 \times 10^8$ bacterial cells/ml saline (1.0 optical density reading at 660 nm).

TABLE 1

S-100 Bacteria List

| Name | Media | Gram + or − | ATTC # |
|---|---|---|---|
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |

TABLE 1-continued

S-100 Bacteria List

| Name | Media | Gram + or − | ATTC # |
|---|---|---|---|
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus influenzae | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

Cows were given daily injections of 5 ml samples of the polyvalent liquid vaccine. Antibody (IgG) titer levels for the injected cattle were determined periodically by using an enzyme-linked immunoassay for bovine antibody against the polyvalent antigen.

EXAMPLE 1B

Immunization Procedures

Heat-killed bacteria were prepared in the manner described above. The polyvalent antigen sample (S-100) obtained was microencapsulated by a conventional phase-separation process to prepare a polyvalent antigen-containing microparticle product. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. No. 3,773,919; U.S. Pat. No. 3,887,699; U.S. Pat. No. 4,118,470; U.S. Pat. No. 4,076,798; all incorporated by reference herein. The polymeric matrix material employed was a biodegradable lactide-glycolide copolymer.

Heat-killed bacterial antigens are encapsulated in such matrix materials, preferably as microspheres of between 1–500 microns diameter, preferably 10×250 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 microns in diameter. Approximately 750 mg of microparticles containing 22% (16.5 mg) of polyvalent antigen was then suspended in about 3 cc of a vehicle (1 wt % Tween 20 and 2 wt % carboxymethyl cellulose in water).

A small group of cattle was selected from a larger herd of cattle. Five of these randomly selected cattle were selected as controls. Four cattle were injected intramuscularly with microparticles containing polyvalent antigen. Microparticle samples were sterilized with 2.0 mRad of gamma radiation.

Antibody (IgG) titer levels were determined periodically from samples of cows' milk obtained from the inoculated cows, as well as from the control cows.

EXAMPLE 2

Isolation of MAIF Factor from Hyperimmunized Milk

Step 1: Milk Filtrate Preparation

Twenty liters of fresh milk from hyperimmunized cows were run through a cream separator (DeLaval Model 102) to remove the fat.

The resulting sixteen liters of skimmed milk was ultra-filtered to remove the high molecular weight species (over 10,000 daltons) using a hollow fiber diafiltration/concentrator (Amicon DL-10L). The concentrator is equipped with two 10,000 daltons molecular weight cut-off cartridges (Amicon $H_5P_{10-43}$). The skimmed milk was run at the pump speed of 80 on the meter and inlet and outlet pressure of 30 psi and 25 respectively.

Twelve liters of the filtrate (<10,000 daltons) coming out of the cartridges at the flow rate of four liters per hour was frozen or lyophilized for storage and for further purification.

Step 2: Ion-Exchange Chromatography

The milk anti-inflammatory factor, in the filtrate was first isolated by an anion exchange chromatography column.

In this procedure, DEAE-Sepharose CL-6B gel (Pharmacia) was used to pack a 5×10 cm glass column which was equilibrated with sterile double distilled water, pH 7.0.

One liter of filtrate (<10,000) was applied to the column and eluted with sterile double distilled water, pH 7.0 at the flow rate of 160 ml per hour. Ten milliliter fractions were collected and monitored at 280 nm in an LKB Uvicord 4700 absorptiometer with an optical density printed out on a connected recorder (Pharmacia REC-482).

Substances other than the anti-inflammatory factor having positive and neutral charges are not bound to the DEAE-Sepharose gel. They are eluted at the fallthrough peak (first peak). The anti-inflammatory factor carrying a negative charge is retained by the gel.

To elute the factor, the column was eluted with a stepwise gradient using sterile physiological saline, pH 7.0. A typical profile is shown in FIG. 1. Bioassay of the individual fractions revealed that the second peak contains the factor. Fractions comprising the second peak and its shoulder are used for further purification. Recovery studies show that 8.8 grams of dried powder were obtained by this process.

Step 3: Gel Filtration Chromatography

The second peak obtained from Step 2 contains the anti-inflammatory factor and other negatively charged molecules; therefore, an additional refining step was needed. To achieve further purification, it is convenient to use a gel filtration column to separate various components on the basis of molecular weight.

In this process, Sephadex G-10 resin (Pharmacia) was packed into a 2.5×80 cm glass column and equilibrated with sterile double distilled water, pH 7.0. Two grams of the second fraction from Step 2 was redissolved in sterile double distilled water and applied to the top of the column. The column was eluted at the flow rate of 30 ml per hour. Fractions (3.3 ml) were collected and monitored at 254 nm and 280 nm (Pharmacia Duo Optical Unit) with optical density printed out on a connected recorder (Pharmacia REC-482).

Figure 2:
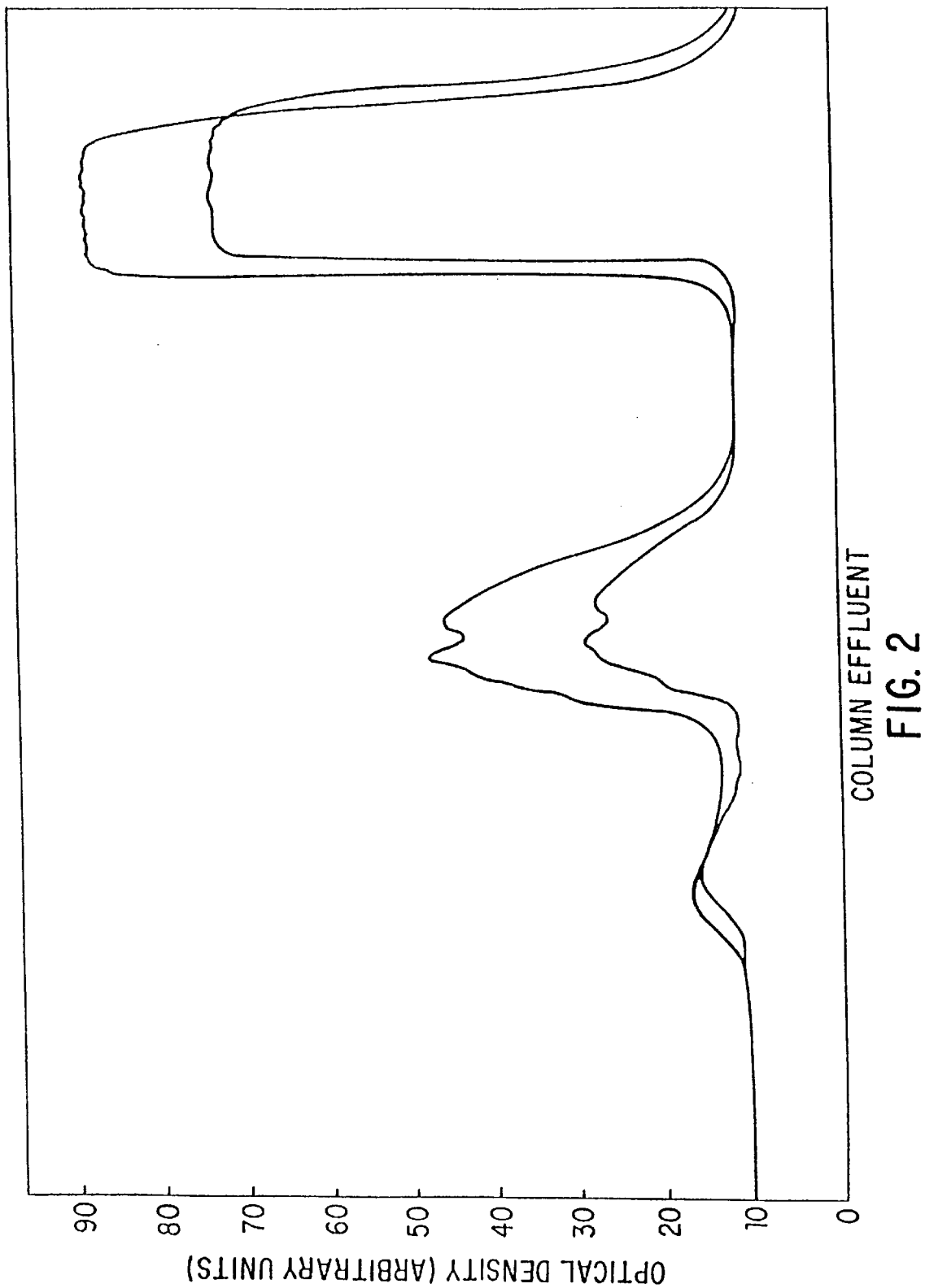
FIG. 2. Fractionation of the anti-inflammatory factor containing peak (second) from DEAE-cellulose chromatography (FIG. 1) on a Sephadex G-10 molecular sieve column.

Typically, there were 3 peaks shown in the elution profile as illustrated in FIG. 2. The first and second peaks contained anti-inflammatory activity.

The first peak is an aggregate that forms on the G-10 column which contains the active factor.

The second peak contains the nonaggregated form of the factor. Both the aggregate form (peak 1) and the nonaggregated form (peak 2) are biologically active in rat bioassay.

EXAMPLE 3

Characterization of Milk Anti-inflammatory Factor

The molecular weight of the non-aggregated form of factor prepared by the method described above was found to be less than 10,000 daltons. This was deduced from the fact that the first step in the isolation of the factor from whey was by ultrafiltration using a membrane that does not allow the passage of molecular weight species >10,000 daltons.

The factor has a negative charge. This was determined by applying milk ultrafiltrate to a DEAE cellulose ion exchange column. The anti-inflammatory activity did not elute from the column with water. Changing the elution media to sodium chloride (0.9% pH) caused the elution of several peaks (FIG. 1). Neutral and positive charged species do not adhere to the ion exchange resin, and negative charged species are eluted by increasing the salt concentration. When the less than 10,000 dalton molecular weight permeate was applied to the DEAE column, neutral salts and sugars eluted with water (Peak 1, FIG. 1). Three distinct peaks eluted when the buffer was changed to saline (Peaks 2–4). The second peak and its shoulder contained anti-inflammatory biological activity in the rat assay. It is concluded, therefore, that the factor has a negative charge.

Another chemical characteristic of the factor is that it forms an aggregate during the process of removing salt. This property became apparent when <10,000 dalton molecular weight permeate was passed over a Sephadex G-10 column, equilibrated with double distilled water and eluted with water at a pH of 7 (FIG. 2). Three peaks eluted from the G-10 column; the first peak eluted with the void volume suggesting a molecular weight equal to or greater than 10,000 dalton. This was unexpected because molecules greater than 10,000 daltons had previously been removed from this sample by ultrafiltration. The second peak eluted in the position expected for the anti-inflammatory factor. Both the first and second peaks exhibited anti-inflammatory biological activity in the rat paw assay, whereas the third peak lacked activity. It was surprising to find that both the first and second peaks had anti-inflammatory biological activity. The material recovered from the first peak of the G-10 column (Step 3) was lyophilized and applied to a G-100 column; a single peak was eluted with the void volume, suggesting a molecular weight of 100,000 daltons or greater. The Step 3 G-10 column removes salt at the same time it separates the different molecular weight species. It is concluded, therefore, that during passage over the G-10 column and resulting removal of salt the anti-inflammatory factor formed a large molecular weight aggregate. The degree of aggregation varied with the salt concentration.

The aggregation property suggests the possibility that a wide spectrum of different molecular weight species can be formed which have anti-inflammatory biological activity due to the presence of the anti-inflammatory factor. The discovery of this property suggests the possibility of producing milk anti-inflammatory factors having a wide spectrum of different biochemical properties depending on the degree of aggregation of the final product. For example, formulations having longer or shorter biological half lives might be produced by using larger or smaller molecular weight aggregates, with molecular weight distribution being controlled by the salt concentration during processing. The column chromatography method described herein results in the smallest molecular weight species that has been obtained which has biological activity (i.e., peak 2 from the Step 3 G-10 column). This observation also suggests using other methods for forming the aggregates. For example, dilution in water causes the aggregation to occur. Chemical agents that bind salts, especially calcium can cause the formation of the aggregate. Having made this discovery, other methods for forming the aggregate and separating the factor will be obvious to those skilled in the art.

EXAMPLE 4

Biological Activity Assay

The anti-inflammatory action of purified anti-inflammatory factor was tested on edema that was caused by the injection of a solution of carrageenan into the footpads of rats. A lyophilized sample of the milk anti-inflammatory factor preparation was dissolved in the appropriate vehicle and given intraperitoneally to experimental rats. The carrageenan was then administered to the rats in an amount of 0.1 ml of a 1% saline solution in each hind footpad. The footpads were measured before injections were given and 2.5 hours after the injections, using a thickness gauge. The results are illustrated in Tables 2 and 3. In these Tables, the abbreviation MAIF refers to the preparation of milk anti-inflammatory factor obtained using the procedures described in Examples 1 and 2 above.

The non-aggregated form of the factor (peak 2 from the G-10 column) from control and hyperimmune milk caused reduction in inflammation of the rat paw at doses between 1 mg and 0.25 mg (Table 2). Both the hyperimmune milk and the regular milk exhibited activity; however, the hyperimmune material was more potent. We concluded from this that the anti-inflammatory factor is present in greater concentration in the milk from hyperimmune cows.

The second peak from the DEAE column exhibited activity when isolated from either hyperimmune milk or regular milk. The activity is substantially greater in the hyperimmune milk (Table 3).

The first peak from the G-10 column, which is the aggregated form of the factor, exhibited activity in rat paw tests (Table 2). However, the aggregated form is not as potent as the nonaggregated form on equal weight basis.

It is concluded from these studies that the anti-inflammatory factor occurs naturally in cows milk. Hyperimmunization of the cows causes higher concentration of factor in the milk. The factor is a small, negatively charged molecule that can be separated from the milk by a variety of methods. The factor can form large molecular weight aggregates that do not naturally occur in milk, but form during processing.

TABLE 2

Effect of Milk Anti-Inflammatory Factor (MAIF) On Reduction of Inflammation in Rats

| MAIF Dosage | Foot Pad Measurements (mm) | | | % Inflammation |
|---|---|---|---|---|
| | Before Injection | After Injection | Difference | |
| Prepared from Hyperimmune Milk | | | | |
| 2.0 mg/rat | 3.43 | 5.01 | 1.58 | 46 |
| 1.0 mg/rat | 3.49 | 5.39 | 1.90 | 54 |

TABLE 2-continued

Effect of Milk Anti-Inflammatory Factor (MAIF) On Reduction of Inflammation in Rats

| MAIF Dosage | Foot Pad Measurements (mm) | | | % Inflammation |
|---|---|---|---|---|
| | Before Injection | After Injection | Difference | |
| 0.5 mg/rat | 3.42 | 5.51 | 2.09 | 61 |
| 0.1 mg/rat | 3.43 | 5.86 | 2.43 | 71 |
| Control/saline | 3.43 | 5.82 | 2.39 | 70 |
| Prepared from Normal Cows Milk | | | | |
| 2.0 mg/rat | 3.30 | 5.24 | 1.94 | 59 |
| 1.0 mg/rat | 3.31 | 5.22 | 1.91 | 58 |
| 0.5 mg/rat | 3.32 | 5.33 | 2.01 | 61 |
| 0.25 mg/rat | 3.31 | 5.42 | 2.11 | 64 |

TABLE 3

Comparison of Semipurified Fractions of MAIF on Reduction of Inflammation in Rats (Prepared from Hyperimmune and Regular Milk)

| | Foot Pad Measurements (mm) | | | % Inflammation |
|---|---|---|---|---|
| | Before Injection | 2.5 hr. After Injection | Difference | |
| DEAE Column Second Peak Hyperimmune Milk 2 mg/rat | 3.25 | 5.04 | 1.79 | 55 |
| DEAE Column Second Peak Regular Milk 2 mg/rat | 3.30 | 5.24 | 1.94 | 59 |
| G-10 Column First Peak 2 mg/rat | 3.31 | 4.98 | 1.67 | 50 |
| Control/Saline | 3.34 | 5.63 | 2.29 | 69 |

EXAMPLE 5

Chemical Analysis of Anti-inflammatory Factor

Anti-inflammatory factor samples were analyzed chemically. The factor is not crystalline in structure, as determined by X-ray diffraction studies. MAIF preparations gave an elemental analysis consistent with carbohydrate composition. The C, H, O ratios were consistent with a polymeric or oligomeric material with some carbinol groups being oxidized to carboxyl. The slight excess of calcium equivalents over chloride ions may be accounted for in part as carboxylate salts. The remainder may be sodium or potassium salts. However, the melting behavior, or rather the non-melting behavior, was suggestive of salt-like and/or higher molecular weight compositions. The material in the present state of purity apparently contains a variable amount of salts of calcium and chloride, probably $CaCl_2$.

Neither preparation contained a significant amount of nitrogen which precludes any peptide component in its composition. Likewise, the absence of significant nitrogen can rule out the presence of amino sugars and other nitrogen-containing materials such as various complex lipids as the major component(s).

Pyrolytic mass spectra revealed significant traces of 18-carbon fatty acids. This fact, taken together with traces of N and P, suggest the presence of a complex lipid in the preparation.

Infrared spectroscopy revealed absorptions consistent with carbinol and carboxylate functionalities. Ultraviolet, visible and fluorescent spectroscopy revealed no significant amount of chromophores beyond those indicated by infrared.

The chemical tests are consistent with an oligomeric carbohydrate, wherein the carbonyl function (aldehyde or ketone) is tied up in the subunit linkages. The oligomeric carbohydrate also contains some side-chain oxidation to carboxylate.

The MAIF preparation is substantially, but not completely pure.

EXAMPLE 6

Rat Paw Edema Tests: Oral Administration

Figure 3:
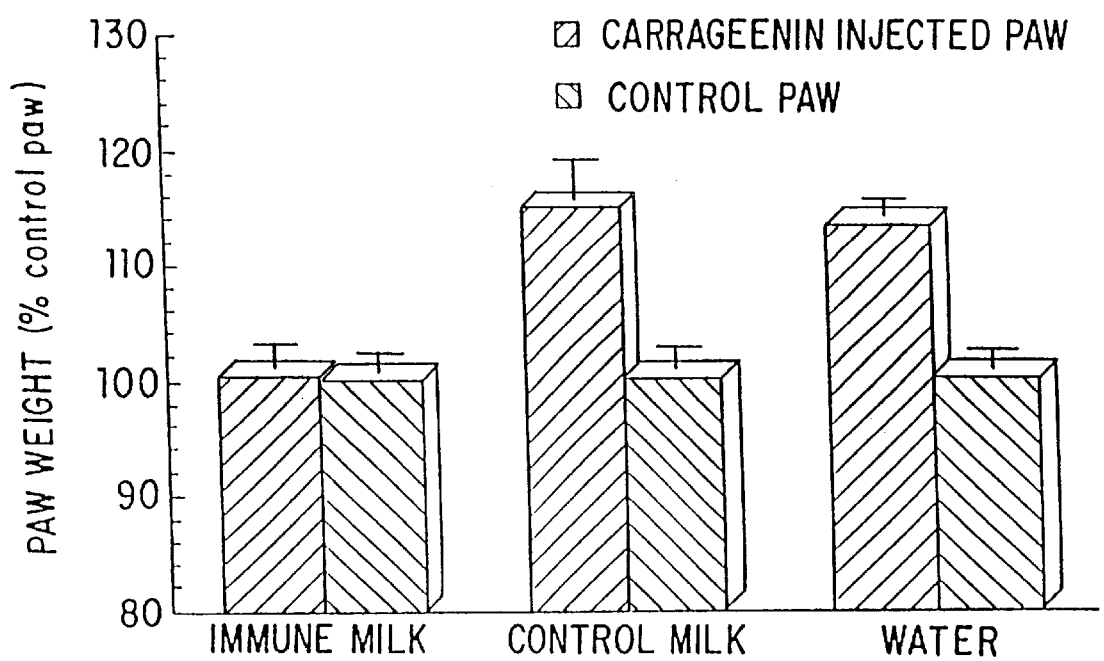
FIG. 3. Effect of immune milk on carrageenan-induced edema in rats (paw weight, % control paw, mean±sem, n=10).

The rat carrageenan footpad assay was used to test the effectiveness of the anti-inflammatory factor as an in vivo anti-inflammatory agent. Thirty adult white rats were randomly divided into three groups of ten rats per group. The groups received, in five consecutive daily treatments, either 10 mg of skim milk powder from hyperimmunized animals, 10 mg of skim milk powder from non-immunized animals or no treatment (20 ml water per day only). The powders were orally administered in 20 ml of water. On the fifth day the right paw of each rat was injected with 0.1 ml of 1% carrageenan in saline. This procedure is known to cause acute inflammation (edema). Twenty-four hours after injection, the rats were sacrificed, the paws amputated, and the weights of the left (control) and right (edematous) paws were compared. The results of the assay are shown in Table 4 (expressed as weight in grams) and in FIG. 3 (expressed as a percentage of the average weight of control paws).

TABLE 4

Rat Paw Edema Test Results
(Paw wt, g, mean ± sem, n = 10)

| Treatment | Carrageenan Paw (wt, g) | Control Paw (wt, g) | Difference (g) |
|---|---|---|---|
| Immune Milk | 1.78 ± 0.03 | 1.71 ± 0.02 | 0.06 ± 0.02 |
| Control Milk | 1.88 ± 0.06 | 1.64 ± 0.03 | 0.24 ± 0.05 |
| Water | 1.86 ± 0.03 | 1.65 ± 0.03 | 0.22 ± 0.02 |

The inflammatory response to carrageenan injection was markedly reduced in the immune milk treated rats as compared with the nonimmune milk and water control groups. No evidence of side effects or adverse effects on the general health of the rats was detected. From these data it can be concluded that daily consumption of skim milk powder from hyperimmunized animals almost completely blocked the inflammatory response induced by carrageenan injection in the footpad of rats.

EXAMPLE 7

Quantitative Rat Paw Edema Tests

A series of experiments was conducted on the hyperimmune milk fraction. The experiments were designed to confirm the anti-inflammatory activity of the milk anti-inflammatory factor when given intraperitoneally and to establish a dose response curve, explore alternative routes of administration, and investigate dosage regimens which might form the basis of further investigations.

Peak I from the G-10 column, supplied by Stolle Milk Biologics International, was prepared according to the methods described in U.S. Pat. No. 4,956,349. Lactose, obtained from commercial sources, was used as placebo. Aspirin was used as a positive control. Aspirin was dissolved in water and given orally by gastric gavage at the ratio of 200 mg per kilogram, a dose known to be active in the assay. A 2% solution of kappa carrageenan (Sigma C-1263) has been found to produce the most reproducible results and was thus used in these experiments. The footpad assay was modified by using isotopically labeled human serum albumin ($^{125}$I-HSA) that localizes in the carrageenan-induced lesion in direct proportion to the volume of the exudate. By determining the total radioactive count in the footpad and comparing this to the counts in a known volume of plasma from the injected animal, a direct measurement of edema in microliters of plasma equivalents is obtained. $^{125}$I-HSA was injected intravenously at a dose of 1.0 microcurie per rat. Female Dark Agouti rats were used. The rats were approximately 12 weeks old, weighed between 160 grams and 200 grams, and were obtained from the in-house inbred colony.

To conduct the carrageenan footpad assay, 0.1 ml of 2% carrageenan was injected subcutaneously into each hind foot pad of an anesthetized rat. This injection was followed immediately by injection of 1.0 microcurie of $^{251}$I-HSA in 0.5 ml of saline into the tail vein. After four hours, each rat was weighed, blood samples obtained, and the rat euthanized. Both hind feet were then removed and the levels of radioactivity in each foot and in the 200 μl plasma standard were measured in an automated gamma counter. From these measurements the volume of edema in each foot was calculated and expressed in microliters.

Experiment 1: Intraperitoneal Dose Response.

Figure 4:
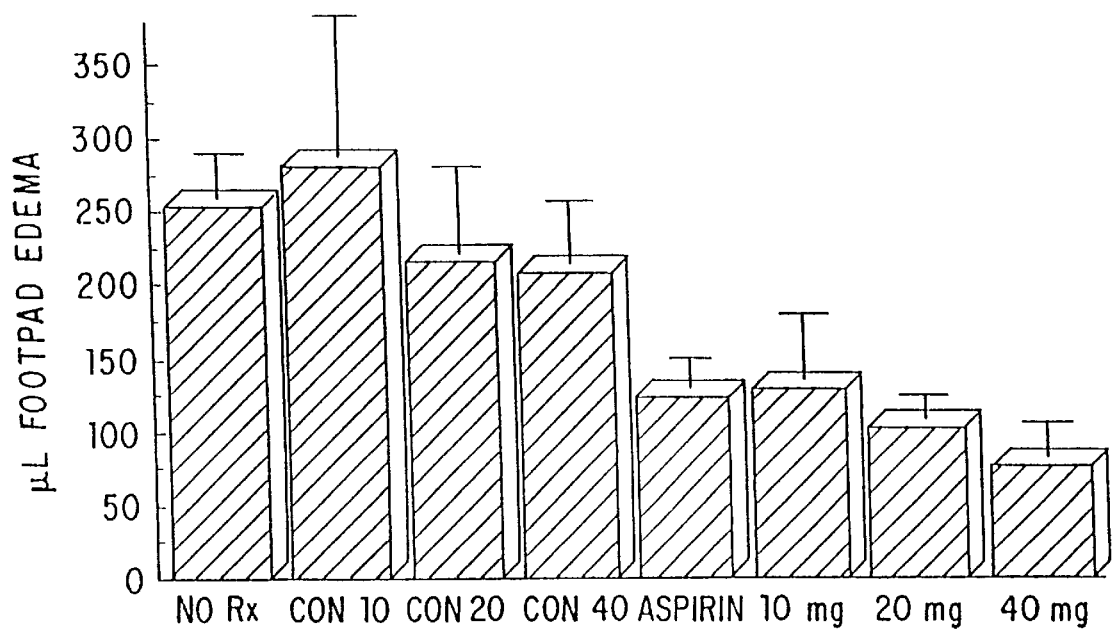
FIG. 4. Effect of intraperitoneal administration of the anti-inflammatory factor on footpad edema in rats ($\mu$L, mean±SD, n=6).

FIG. 4 illustrates the effect of intraperitoneal administration of a purified preparation of MAIF compared to lactose (CON), aspirin, and no treatment (No $R_x$). All treatments (lactose, aspirin, MAIF) were given 30 minutes prior to the injection of carrageenan.

Figure 5:
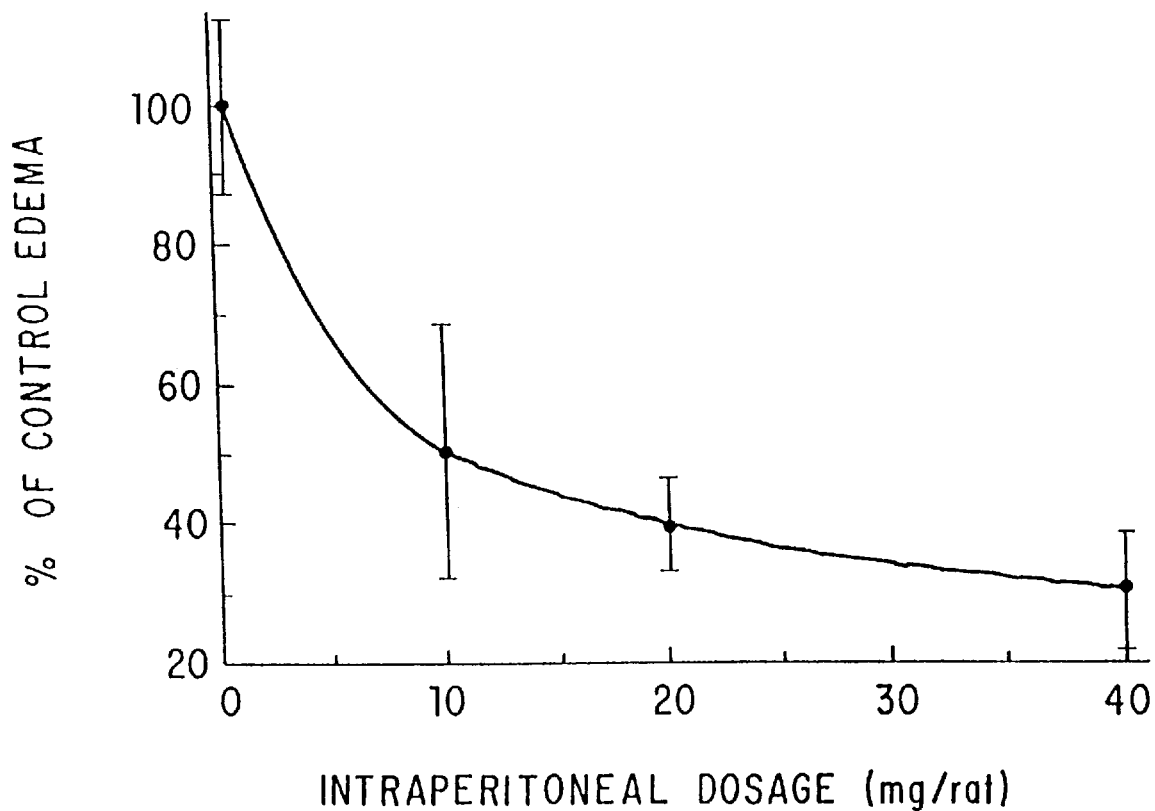
FIG. 5. Intraperitoneal dose-response curve for the anti-inflammatory factor in rat paw edema test (% control, mean±SD, n=6).

Carrageenan injection resulted in edema averaging 250 μl (No $R_x$). The edema was inhibited by aspirin and all dosages of the MAIF preparation but was not inhibited by lactose. The intraperitoneal dose-response curve obtained with the MAIF preparation, derived by expressing the data as percentage of average control (no treatment) edema is shown in FIG. 5.

Experiment 2: Effects of Various Routes of MAIF Administration.

Figure 6:
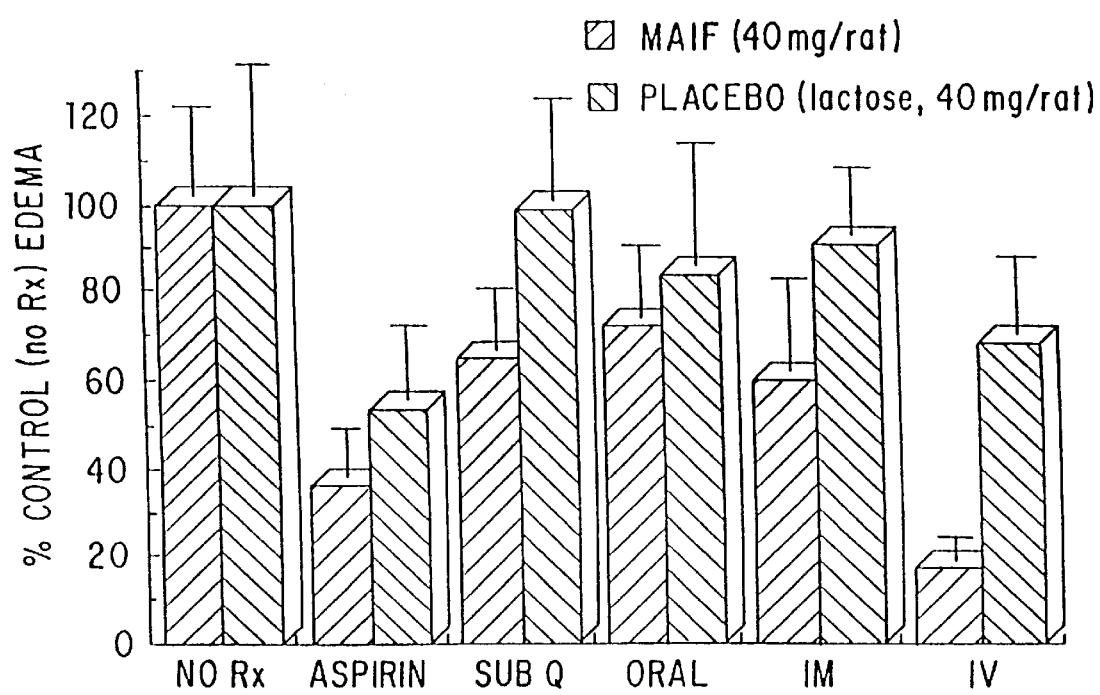
FIG. 6. Effect of hyperimmune milk factor vs. placebo (lactose) on footpad edema in rats (% control, mean±SD, n=6).

FIG. 6 illustrates the effect, on footpad edema, of the administration of lactose and a preparation of purified MAIF orally (ORAL), intramuscularly (IM), subcutaneously (SUB Q), and intravenously (IV). Also shown are a positive control (aspirin) and a nontreated control (NO $R_x$).

The preparations were administered prior to carrageenan challenge according to the following schedule: Aspirin: orally, 30 minutes prior; Subcutaneous MAIF: 1 hour prior; Oral MAIF: 24, 16 and 1 hour prior; intramuscular MAIF: 30 minutes prior; intravenous MAIF: at the time of challenge (isotope was also injected).

The results indicate that, expressed as the percentage of average control edema in each separate assay, the anti-inflammatory factor, by all routes of administration, inhibited edema formation. Forty milligrams of the MAIF preparation given intravenously almost completely abrogated the inflammatory response to carrageenan. These results demonstrate the anti-inflammatory activity of MAIF and, in view of the results of Experiment 1 above, suggest that the order of effectiveness for different routes of administration is IV>IP>IM>SUB Q>ORAL.

Experiment 3: Effect on Edema of Intravenous and Extended Oral Administration: Dose Response.

Figure 7:
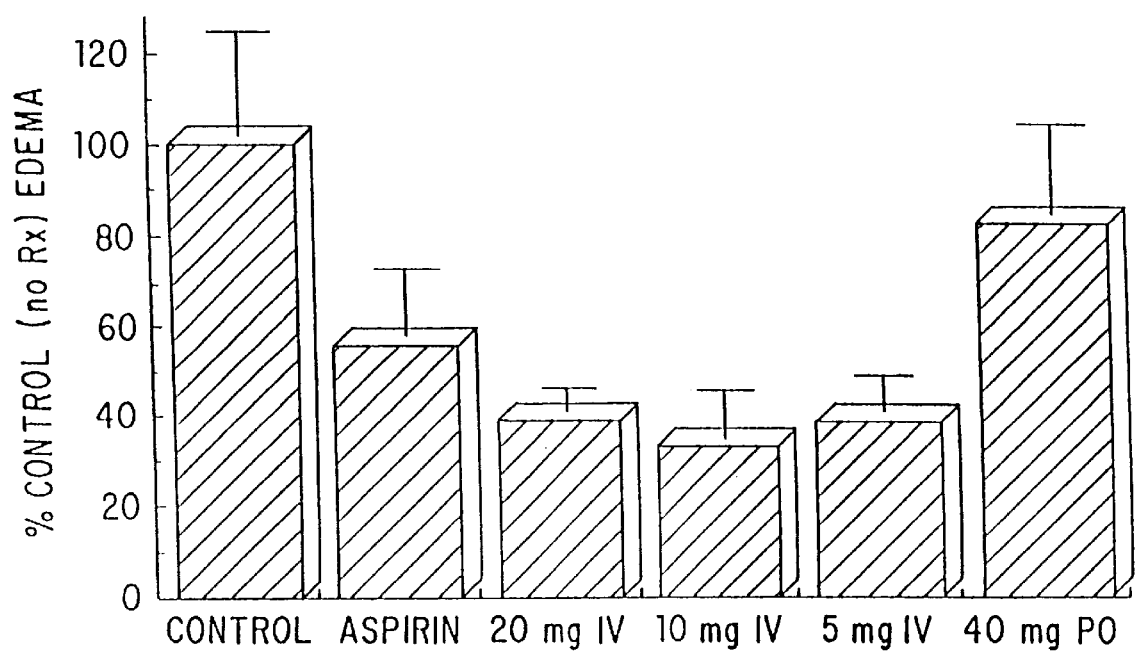
FIG. 7. Effect of iv and oral MAIF on footpad edema in rats (% control, mean±SD, n=6).

FIG. 7 shows the effects of IV and oral administration of a purified preparation of anti-inflammatory factor on footpad edema in rats. MAIF oral treatment (40 mg per rat per day) was given daily for six days and also one hour before carrageenan challenge (PO). Intravenous treatments (5, 10, 20 mg) were given at the time of carrageenan challenge (IV). Also shown are a positive control (aspirin) and a negative control (no treatment).

The results shown in FIG. 7 indicate that all three dosages of the MAIF preparation result in anti-inflammatory activity that exceeds even the activity of aspirin in the assay, whereas extended oral administration results in marked but limited activity.

Figure 8:
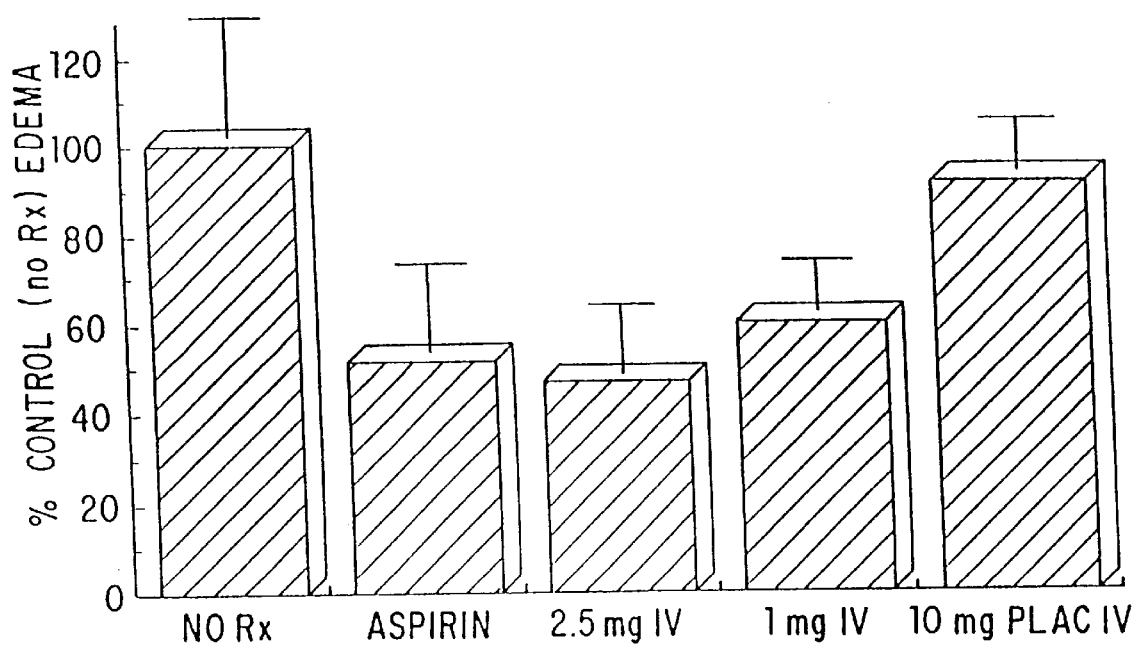
FIG. 8. Effect of low iv dosage of MAIF on footpad edema in rats (% control, mean±SD, n=6).

The study was therefore extended to examine the effects of further reduced intravenous dosages of anti-inflammatory factor. Intravenous dosages of lactose placebo were included as a control. The results of these studies are shown in FIG. 8. Intravenous dosages of 2.5 and 1 mg of the MAIF preparation (IV) induced anti-inflammatory activity in the range of the activity induced by aspirin. 10 ml of intravenous lactose placebo (10 mg PLAC IV) did not induce activity in that range.

Figure 9:
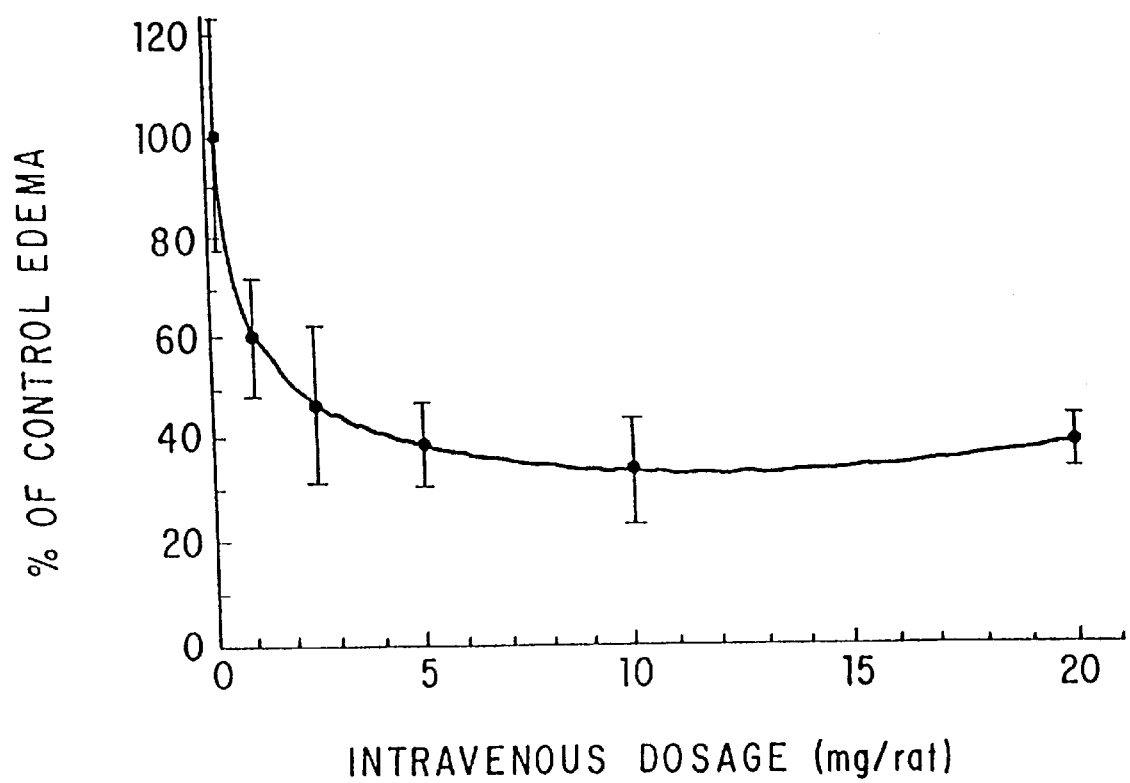
FIG. 9. Intravenous dose-response curve for MAIF in rat paw edema test (% control, mean±SD, n=6).

An intravenous dose-response curve was derived by combining the results of Experiments 2 and 3 and expressing these results as percentage average control edema (no treatment) in each separate assay. The curve is shown in FIG. 9.

The conclusions that may be drawn from the quantitative rat paw edema tests are as follows: milk fraction peak I from the G-10 column, extracted and purified as described in U.S. Pat. No. 4,956,349, consistently shows anti-inflammatory activity when tested in the rat paw edema model. A dosage of 4 mgs of MAIF preparation per rat given intravenously at the time of carrageenan injection is sufficient to drastically inhibit edema and was therefore chosen as a standard against which other preparations would be compared in further experiments.

EXAMPLE 8

Anti-Inflammatory Properties of Preparations of Hyperimmune Milk Obtained from Identical Twin Cows The effect of vaccination on the anti-inflammatory activity of milk was investigated by testing the bioactivity of various milk fractions obtained from identical twin cows. Based on the extraction methods described in U.S. Pat. No. 4,956,349, an extraction scheme utilizing ultra-filtration was devised. The processing sequence was as follows:

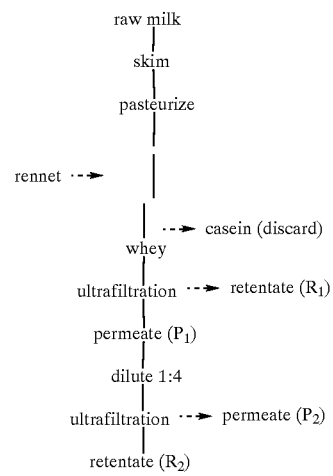

Milk samples were prepared from immunized twin cows, non-immunized control twin cows, and reconstituted skim milk powder previously prepared from immunized cows. The sample group consisted of 45 sets of identical twin cows. One cow of each twin set was vaccinated bi-weekly with Stolle S100 mixed bacterin (described in U.S. Pat. No. 4,956,349). The bioactivity of the various fractions was tested by intravenous injection using the rat carrageenan footpad assay described above.

The hypotheses to be tested were that (a) hyperimmunization was responsible for the anti-inflammatory activity described above. (b) MAIF could be extracted on a commercial scale by ultra-filtration, and (c) dilution of the permeate would cause aggregation of the anti-inflammatory factor, causing it to be retained by the 30,000 molecular weight ultra-filtration membrane.

Figure 10:
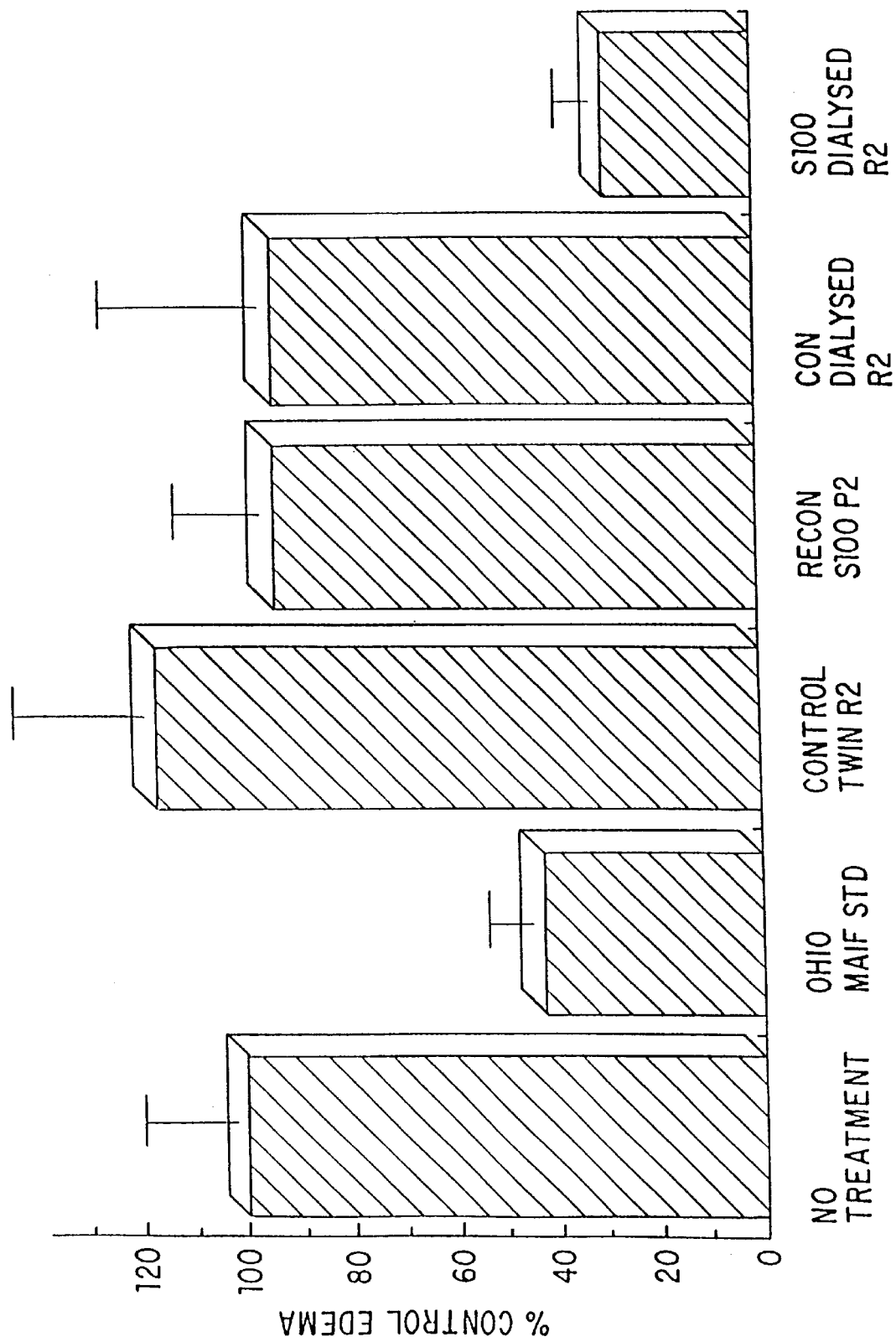
FIG. 10. Run 1, twin herd/ultrafiltration experiments (% average control edema, mean±SD, n=6).

FIG. 10 illustrates the results of a twin herd ultra-filtration experiment designed to test the bioactivity of various fractions made from the milk of non-vaccinated control twins and from reconstituted milk powder from immunized cows. The fractions that were tested are as follows: Peak I, G-10 column preparation, 4 mls (OHIO MAIF STD); $R_2$ final retentate from non-vaccinated twin (CONTROL TWIN $R_2$); $P_2$ final permeate from the reconstituted milk powder (RECON S100 $P_2$); dialyzed $R_2$ final retentate from non-vaccinated twin (CON DIALYZED $R_2$); dialyzed final retentate from the reconstituted milk powder (S100 DIALYZED $R_2$).

No anti-inflammatory activity could be detected in the $R_2$ final retentate fraction prepared from nonimmunized cows, even after dialysis. No anti-inflammatory activity was detected in the final permeate $P_2$ fraction prepared from the reconstituted milk powder. The reconstituted milk powder retentate $R_2$ fraction, following dialysis, exhibited anti-inflammatory activity in the range of the activity of the MAIF standard.

Figure 11:
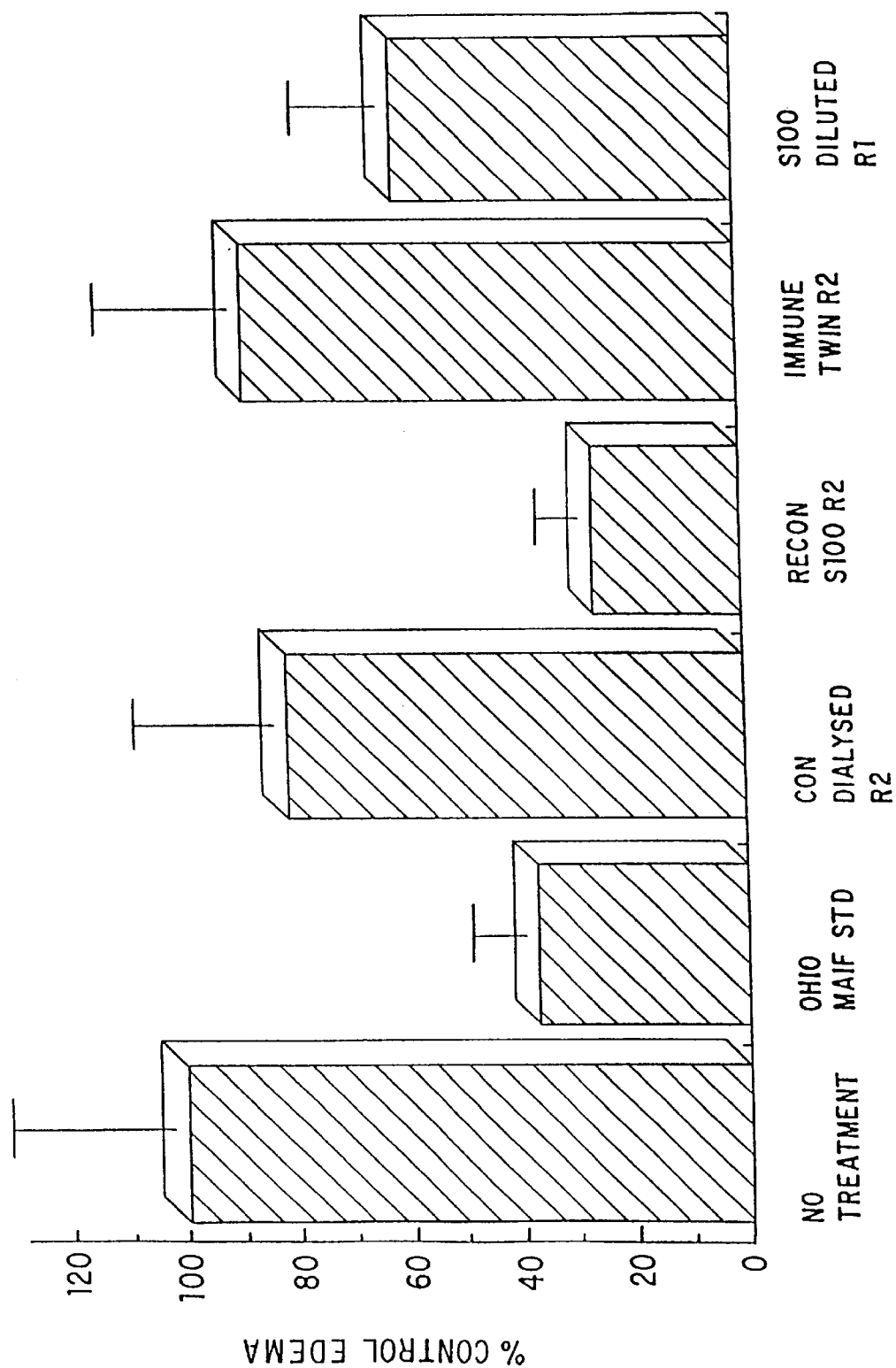
FIG. 11. Run 2, twin herd/ultrafiltration experiments (% average control edema, mean±SD, n=6).

FIG. 11 illustrates the results of twin herd ultra-filtration experiments designed to test the bioactivity of various milk fractions made from vaccinated and nonvaccinated twin cows and from reconstituted milk powder from immunized cows. The fractions that were tested are as follows: Peak I, G-10 column preparation, 4 ml (OHIO MAIF STD); dialyzed final retentate $R_2$ from non-vaccinated twins (CON DIALYZED $R_2$); final retentate $R_2$ from the reconstituted milk powder (RECON S100 $R_2$); the final retentate $R_2$ from vaccinated twins (IMMUNE TWIN $R_2$); first retentate R1 from the reconstituted milk powder, diluted for: 1 (S100 DILUTED R1).

Little anti-inflammatory activity was detected in the dialyzed retentate $R_2$ from non-vaccinated control twins or in the non-dialyzed retentate $R_2$ from the vaccinated twins. Some activity is detectable by scattergram. $R_2$ retentate prepared without dialysis from reconstituted Stolle milk powder from immunized cows was strongly anti-inflammatory. However, the preparation made by dilution of the reconstituted milk before ultrafiltration rather than dilution of whey made from the milk was only marginally active. This result indicates that anti-inflammatory activity is more efficiently extracted from the whey fraction.

Figure 12:
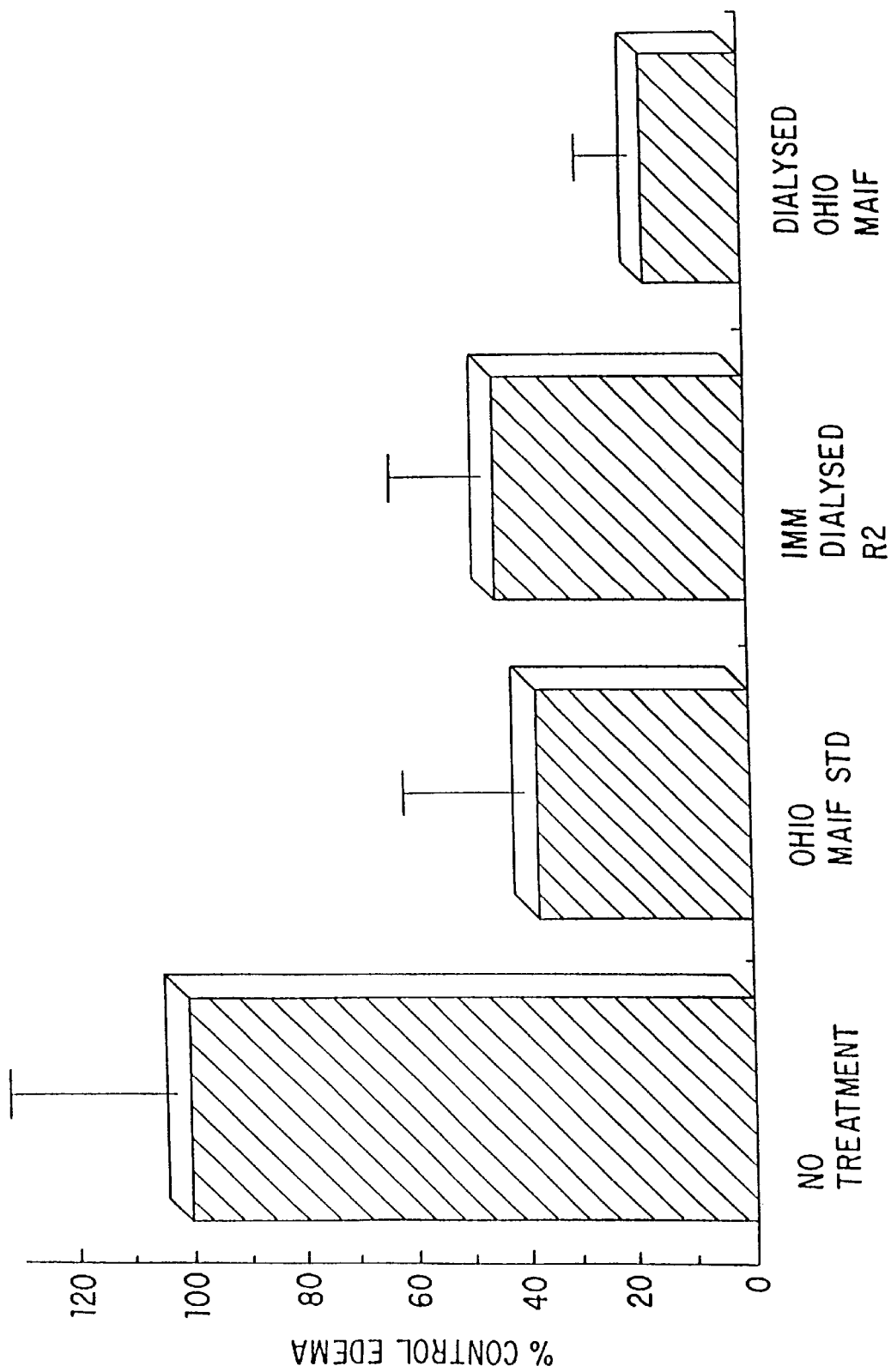
FIG. 12. Run 3, twin herd/ultrafiltration experiments (% average control edema, mean±SD, n=6).

FIG. 12 illustrates the results of twin herd ultrafiltration experiments designed to test the bioactivity of dialyzed retentate from vaccinated twin cows. The fractions tested are as follows: Peak I, G-10 column preparation (OHIO MAIF STD); dialyzed final retentate $R_2$ from vaccinated twins (IMM DIALYZED $R_2$); dialyzed final retentate from the G-10 preparation (DIALYZED OHIO MAIF). The results show that anti-inflammatory activity was present in the $R_2$ fraction from the immunized twin after dialysis. Dialyzed MAIF was more active in the assay than the nondialyzed MAIF standard. This result suggests that dialysis is an effective means of further concentrating the milk factor responsible for anti-inflammatory activity.

The results presented in FIGS. 10–12 above support the following conclusions: (1) anti-inflammatory activity can be extracted from reconstituted milk from immunized cows by ultrafiltration of the diluted permeate. (2) anti-inflammatory activity was not demonstrated in the above-preparations that were made from the milk of non-immunized cows. (3) anti-inflammatory activity was demonstrated in the final retentate $R_2$ after ultrafiltration of diluted permeate prepared from the milk of immunized cows, but dialysis was necessary in order to demonstrate the activity.

EXAMPLE 9

Stability of MAIF, Heating, and Proteinase Treatment of MAIF

The previous evidence that the milk anti-inflammatory factor was chemically not a protein or a peptide was based largely on chemical analyses that consistently showed an almost complete absence of nitrogen. For further characterization of the anti-inflammatory factor, several preparations were tested in the rat paw edema assay, using 4 mgs of peak I, G-10 column preparation, intravenously as the standard. The following treatments were done: proteinase (pronase) treatment for six hours; six hours no proteinase treatment control; untreated positive control; heating at 100° C. for 30 minutes.

Figure 13:
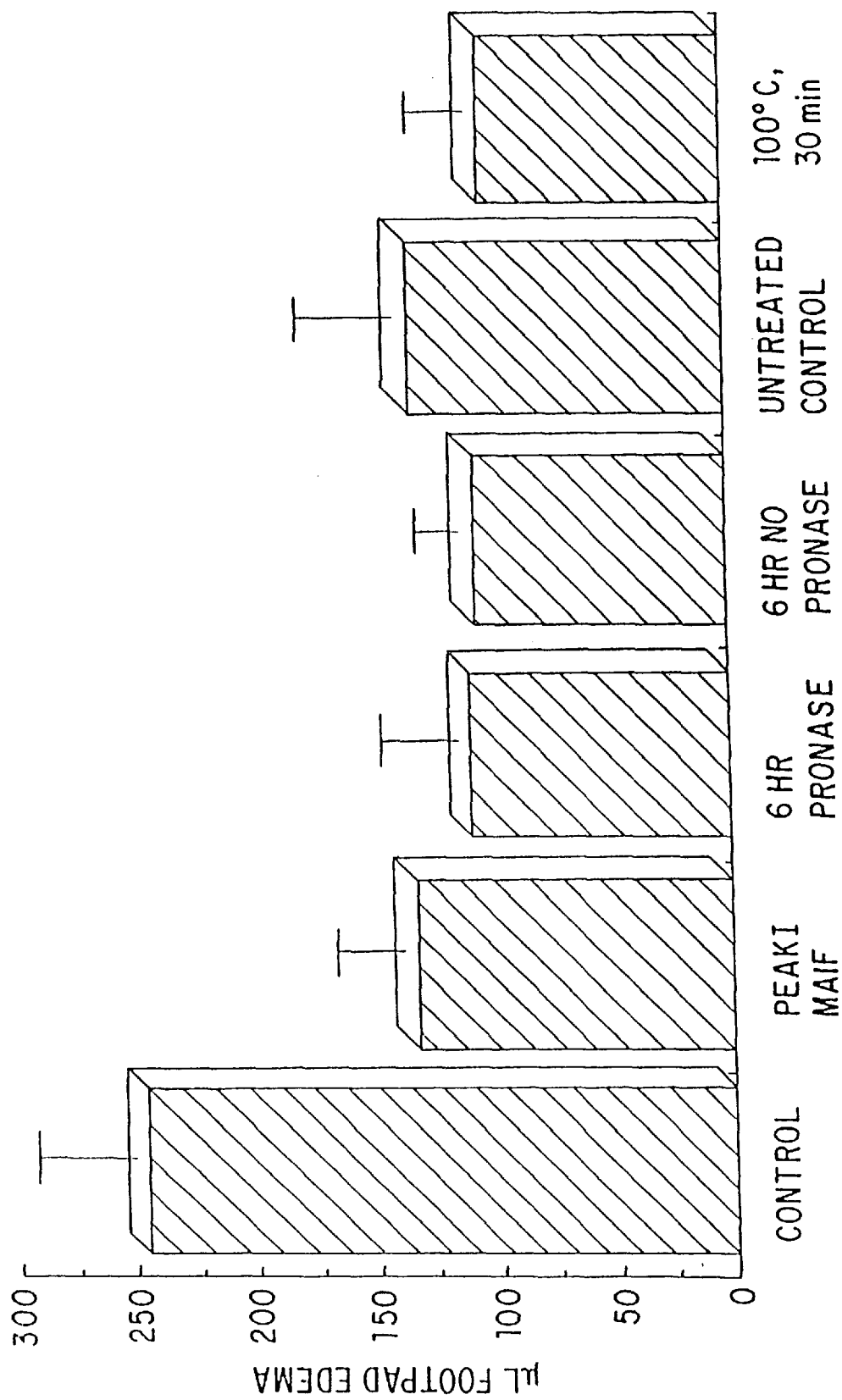
FIG. 13. Effect of various treatments of MAIF on inhibition of footpad edema in rats ($\mu$L footpad edema, mean±SD, n=6).

The results of this assay are illustrated in FIG. 13. The conclusions derived from this study were that the anti-inflammatory activity is not due to a protein or peptide and that the anti-inflammatory factor is not inactivated by boiling. The effectiveness of pronase treatment was verified by the finding that parallel pronase treatment completely denatured milk protein.

EXAMPLE 10

Anti-Inflammatory Activity of Further Purified MAIF and Whey Protein Concentrate from Immunized Cows Retentate and permeate from ultrafiltration using an Amicon YM5 membrane were tested for biological activity using intravenous administration in the rat paw edema assay. In this process, the MAIF in peak I of the G-10 column, prepared according to U.S. Pat. No. 4,956,349, was further purified by ultrafiltration on an Amicon YM5 membrane. This membrane retains molecules of 5000 molecular weight or greater. Whey protein concentrates (WPCs) were also prepared from milk from immunized animals and filtered through the YM5 membrane. The following samples were tested in the assay using 4 mg peak I, G-10 column preparation, intravenously as the standard: permeate from Amicon YM5 ultrafiltration; retentate from Amicon YM5 ultrafiltration; WPC from immunized cows, 30 mgs per rat; WPC from commercial production (non-immunized cows), 30 mg per rat.

Figure 14:
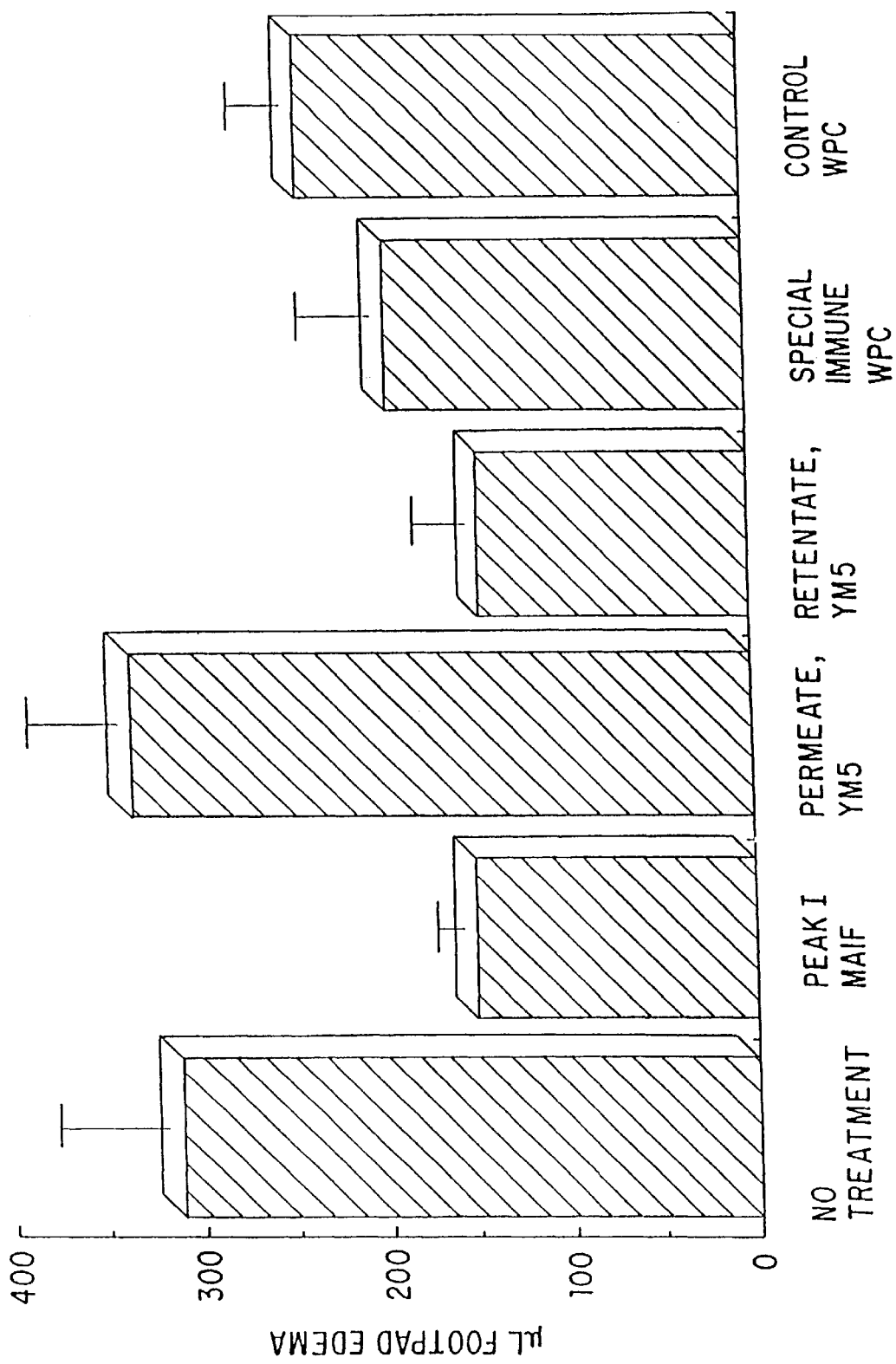
FIG. 14. Effect of fractions of MAIF and of immune wpc on inhibition of footpad edema in rats ($\mu$L footpad edema, mean±SD, n=6).

The results of this assay are illustrated in FIG. 14. It is clear from these results that all of the activity is in the retentate which comprised approximately 0.5% of the total weight of the fraction applied to the YM5 filter. The reduction of edema seen in this experiment was achieved following administration of 20–25 micrograms of material.

Regarding the activity of WPC, WPC made from hyperimmunized animals clearly showed anti-inflammatory activity as expected. Interestingly, WPC made from non-immunized animals also showed anti-inflammatory activity. The presence of anti-inflammatory activity in the milk of nonimmunized cows is not surprising since it must be a natural substance. Its detection reflects the sensitivity of the bioassay.

EXAMPLE 11

Continuous Monitoring of Carrageenan Induced Footpad Edema

Figure 15:
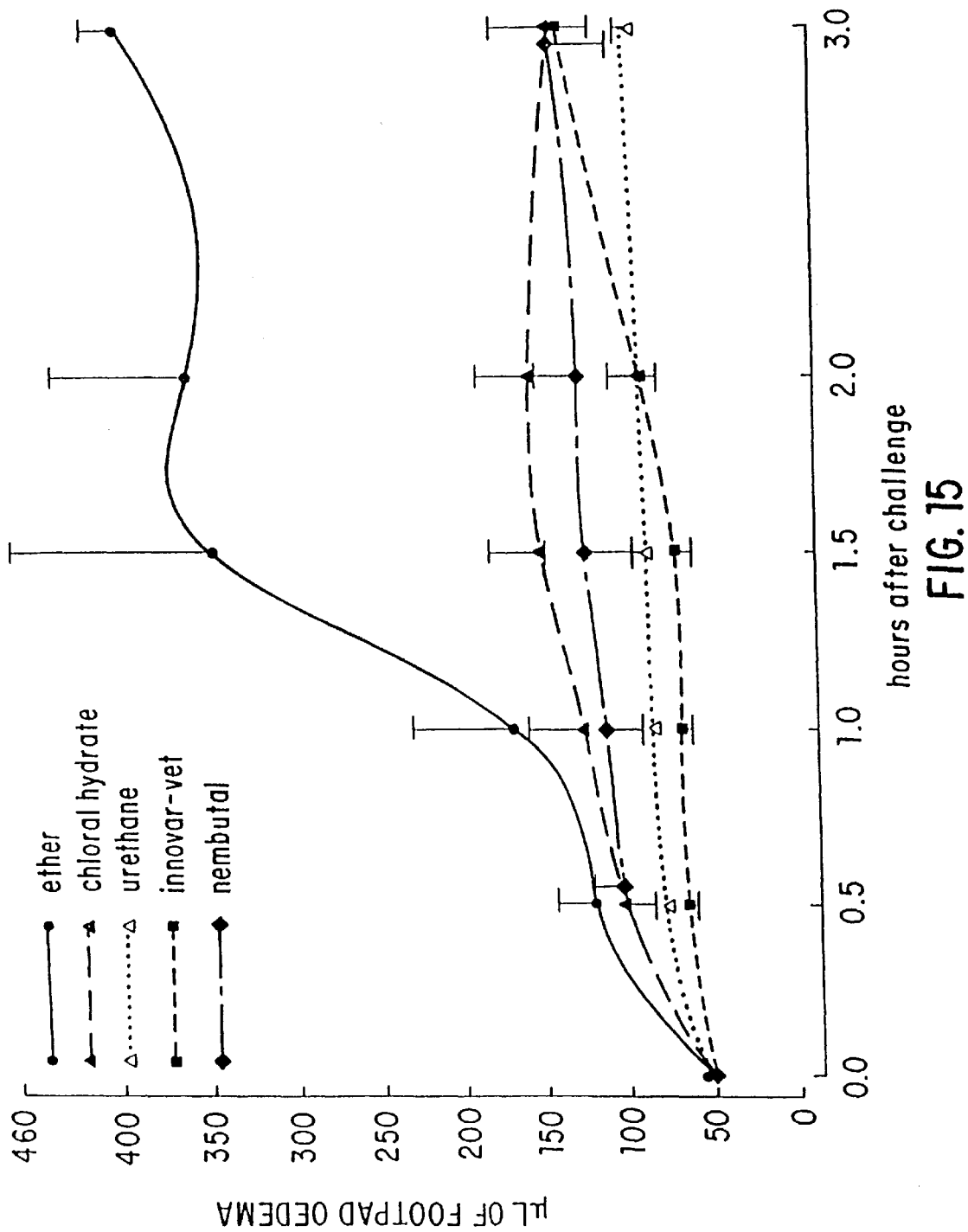
FIG. 15. Effect of five different anesthetics on the response to carrageenan in the rat footpad. The accumulation of edema was monitored at selected intervals in the same animals. n=6 for each data point.

It was established that 4 mg of MAIF preparation given intravenously at the time of carrageenan injection reduced the accumulation of edema in the footpad by between 40% and 50%. Although these results provided evidence that the material contained an anti-inflammatory moiety, there was little indication of the site of action or pharmacological profile of MAIF. In order to obtain such data it was necessary to establish a method that allowed the continuous monitoring of footpad edema throughout the response to carrageenan. This was achieved by holding the rat foot in a demounted Gamma radiation detector. The procedure required animals to be anesthetized for up to four hours and, as anesthetics are known to suppress the inflammatory response, it was first necessary to determine the effect of anesthetics on the carrageenan-induced edema. Five agents commonly used to induce anesthesia in rats were therefore evaluated; these were ether, chloral hydrate, Innovar-vet, nembutal and urethane. The results are shown in FIG. 15.

Figure 16:
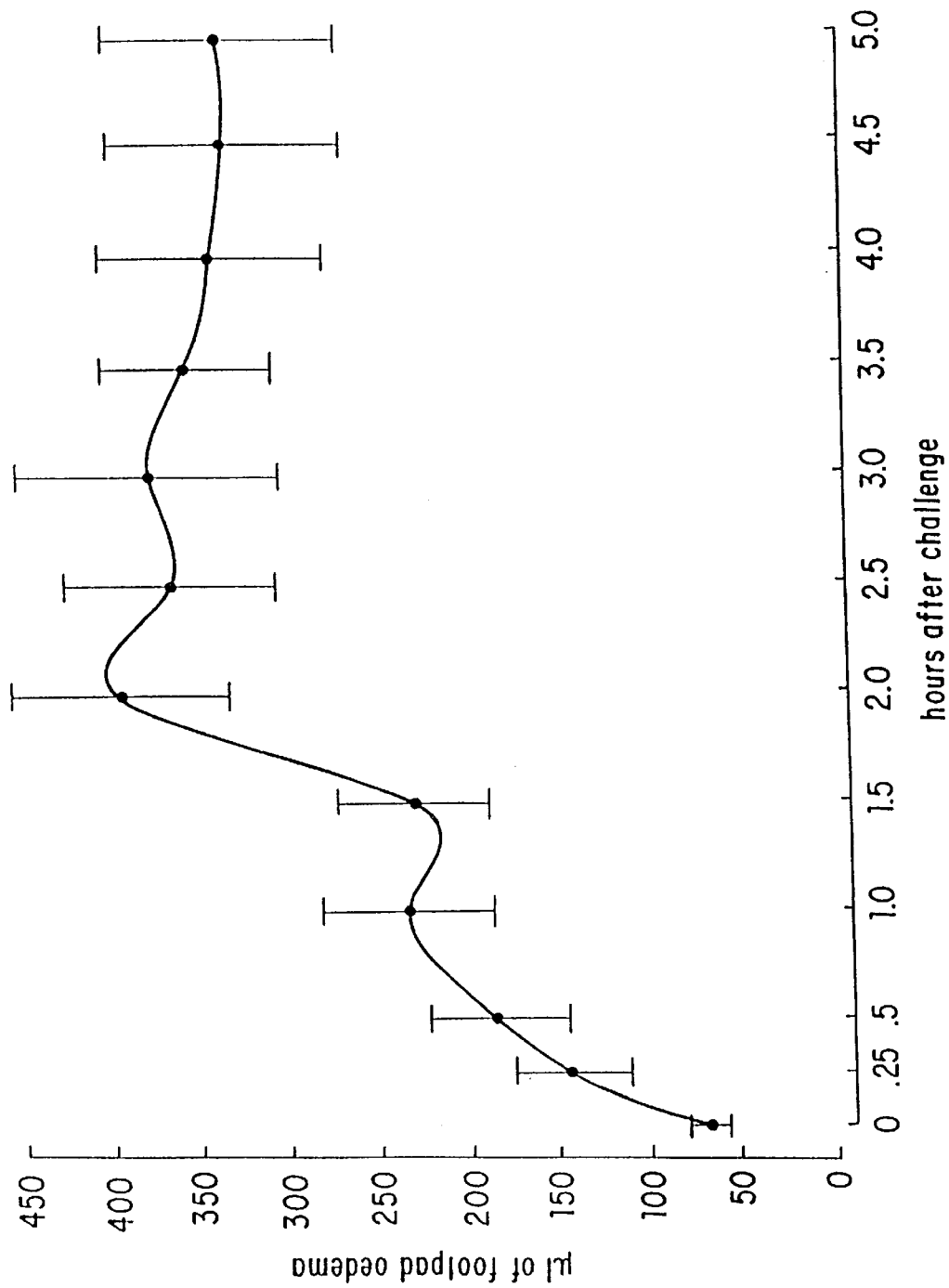
FIG. 16. Demonstration of the biphasic nature of the response to carrageenan in the rat footpad. n=5 for each data point. Ether was used as the anesthetic.

It was clear from these results that ether was the anesthetic of choice when the inflammatory response was to be evaluated by this technique. The shape of the curve obtained when ether was used indicated a biphasic response. To delineate the response in more detail a further experiment was carried out in which the volume of edema was measured at 12 time points over a 5 hour period. The results confirmed a biphasic response. The early response occurred between 0 and 1 hour after challenge and late phase response between 1.5 and 2 hours (FIG. 16).

The two phases, which have also been observed by other investigators, have been termed the non-phagocytic inflammatory response (NPIR) and the phagocytic inflammatory response (PIR), respectively.

Figure 17A:
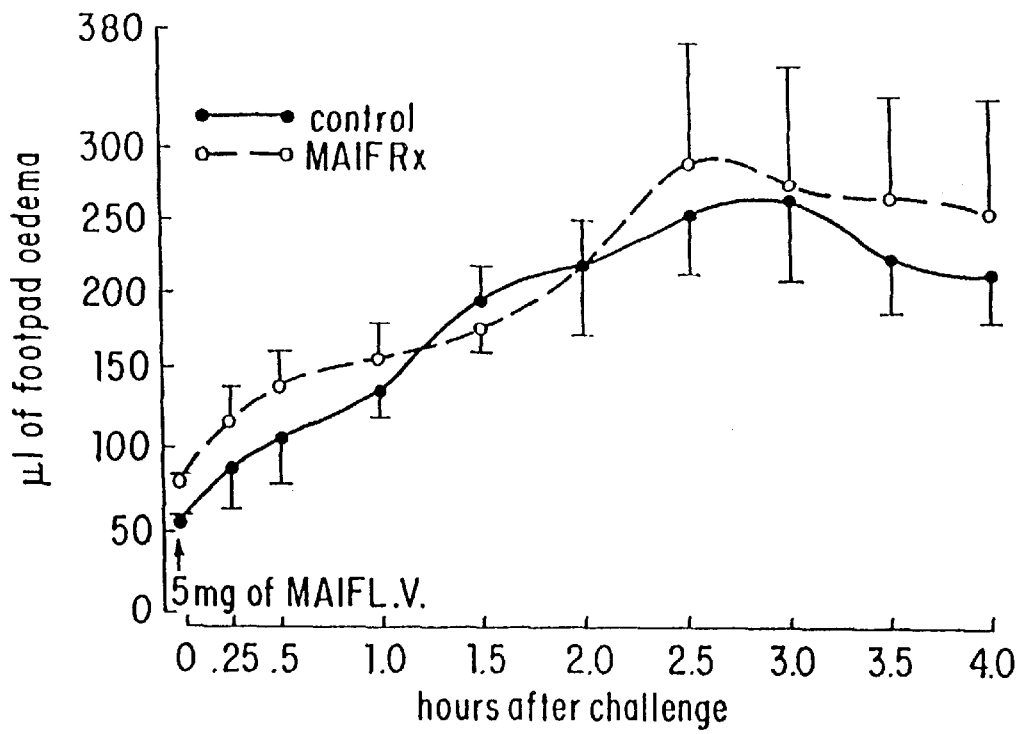
FIG. 17(A–B). MAIF, administered at either 5 mg per rat (A) or 40 mg per rat (B) does not inhibit the inflammatory response to carrageenan in ether-anesthetized rats. n=4 for all data points.
Figure 17B:
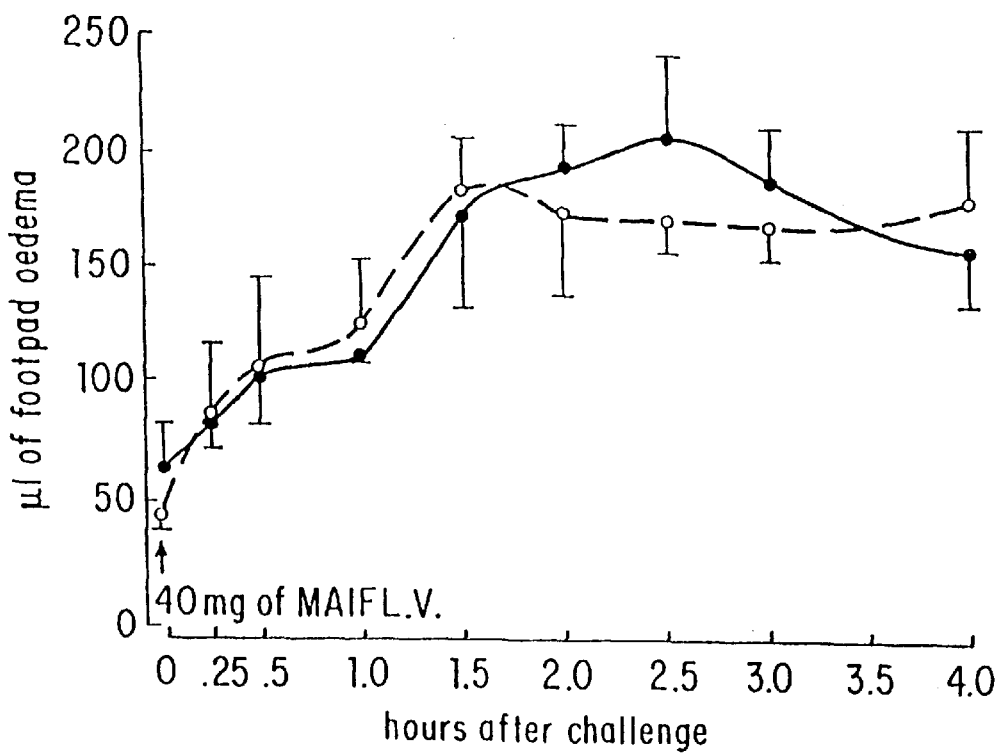

The NPIR is initiated, in response to injury, by soluble mediators such as histamine and bradykinin while the PIR depends on the participation of neutrophils. The protocol, therefore, was to administer MAIF and monitor the accumulation of edema continuously in an effort to determine whether the anti-inflammatory properties of the agent were a result of an effect on the early non-cellular (NPIR) or the later cellular (PIR) phase. 5 mg or 40 mg of MAIF preparation per rat were administered intravenously at the time of carrageenan challenge and the accumulation of edema monitored at regular intervals over a four hour period. Neither dose affected the accumulation of edema during either phase (FIG. 17).

This result was surprising as many previous analyses, in which the effect of purified preparations of MAIF on carrageenan induced edema 4 hours after challenge was determined, had demonstrated considerable anti-inflammatory activity in the fractions. It was likely, therefore, that the continuous exposure to ether suppressed or inactivated the active anti-inflammatory component of MAIF in vivo.

Figure 18:
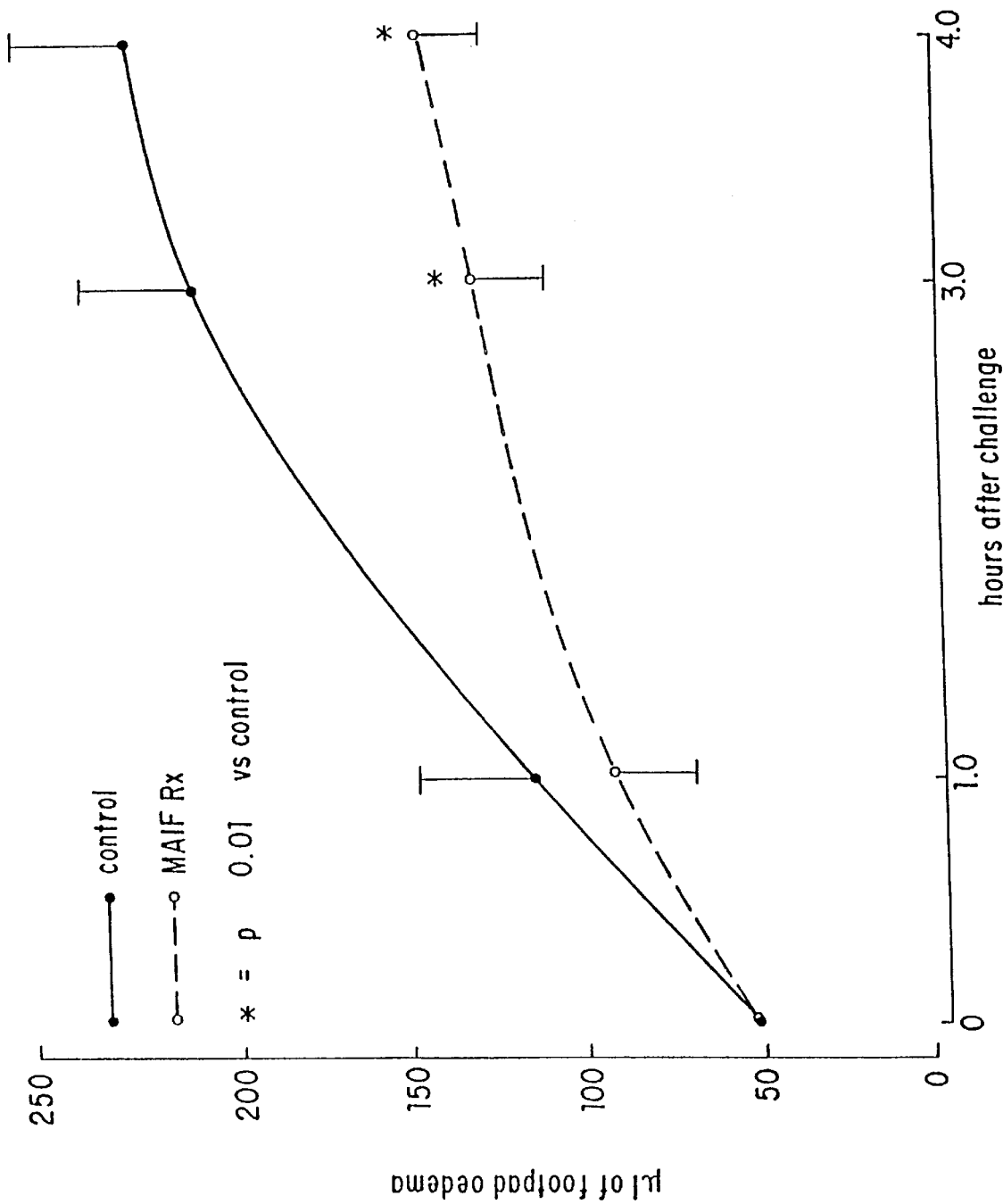
FIG. 18. Suppression of carrageenan-induced edema accumulation during the secondary, phagocytic-cell mediated, response by 40 mg of MAIF injected i.v. at the time of carrageenan challenge (time 0). n=12 for each data point in the control group and n=10 for each data point in the MAIF-treated group.

Previous studies indicated that short term exposure to ether did not affect the activity of the anti-inflammatory factor. Therefore, an experiment was done in which the effect of MAIF on progressive edema accumulation was determined at only four time points, O, 1, 3 and 4 hours, thus limiting the exposure of the animals to ether. The 1 hour time point was chosen to assess the affect on the early non-phagocytic inflammatory response while the 3 and 4 hour measurements were selected to quantify the effect on the later phagocytic inflammatory response. In this experiment the MAIF preparation administered at 40 mg resulted in a reduction in the accumulation of edema during the secondary, phagocytic-cell mediated phase, but had no significant effect on the primary, soluble mediator driven phase (FIG. 18).

The following conclusions can be drawn from this series of experiments.

1. Ether is the preferred anesthetic for use in experiments where the inflammatory response to carrageenan is to be monitored continuously.
2. Continuous ether anesthesia inhibits the in vivo anti-inflammatory activity of anti-inflammatory factor in the carrageenan footpad assay.
3. MAIF ameliorates inflammation by inhibiting the late, phagocytic-cell mediated phase of the inflammatory response to carrageenan.

EXAMPLE 12

Time Course of the Effect of MAIF on Carrageenan Induced Footpad Edema

A further series of experiments were carried out in which the agent was administered at selected time points before or after the injection of carrageenan rather than at the time of challenge. The purpose of the study was to provide information on (a) the most effective time for administration of MAIF in relation to the inflammatory stimulus.
(b) the biological half life of the anti-inflammatory moiety.
(c) the points in the development inflammatory response affected by MAIF.

Figure 19:
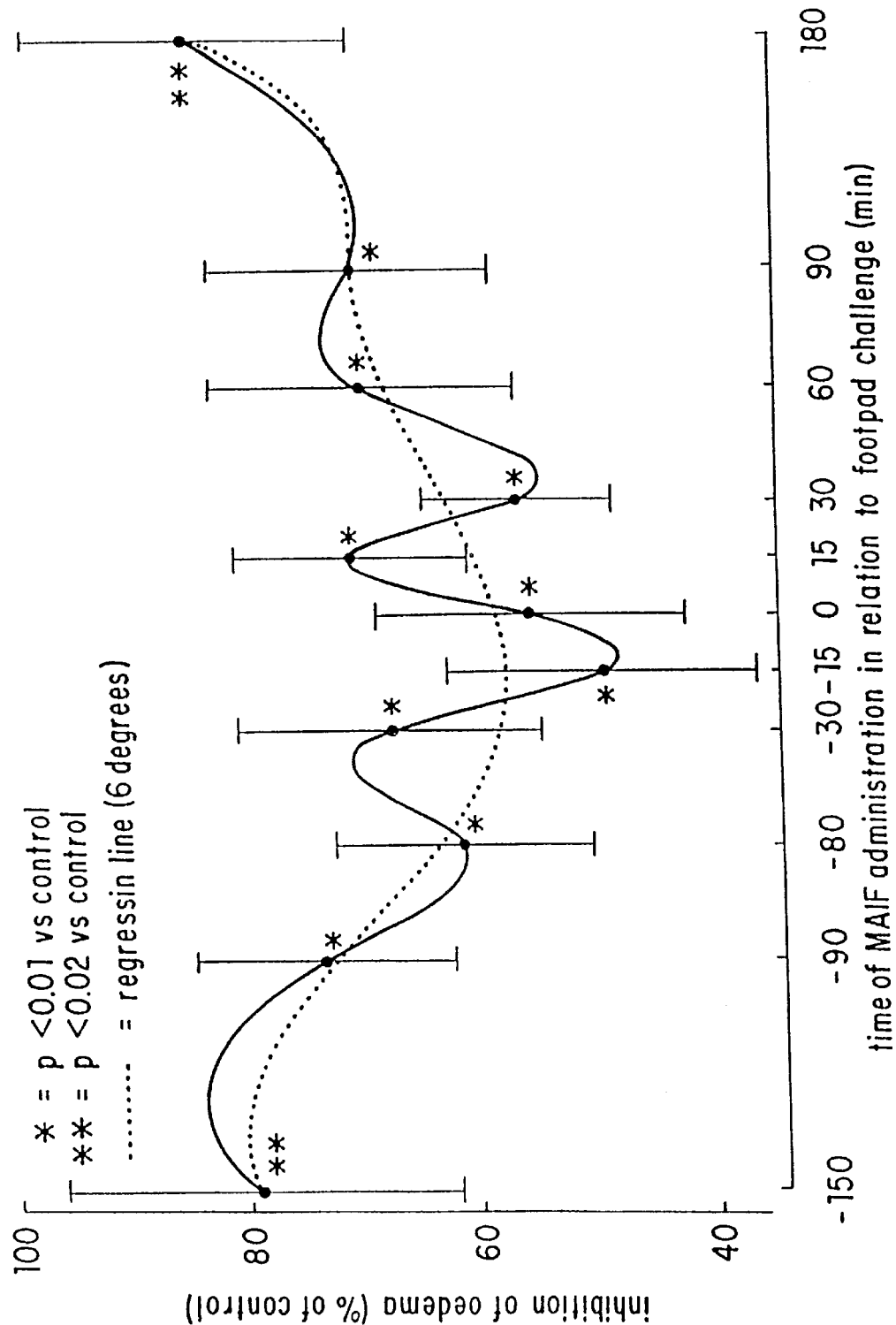
FIG. 19. Effect of MAIF, given i.v. at 4 mg per rat at different times, on the response to carrageenan in the rat footpad. Edema was assessed 4 hours after challenge in all cases. n=12 for each data point.

The study was carried out in three parts. A preparation of MAIF was administered intravenously at a dose of 4 mg/rat at one of 11 time points, ranging from 150 minutes before, to 150 minutes after injection of carrageenan. Results of this experiment are shown in FIG. 19 and Table 5.

TABLE 5

| Experiment | Time of A in relation to challenge (min) | Mean foot volume of control groups ($\mu l \pm SD$) | Mean foot volume of MAIF groups ($\mu l \pm SD$) | Inhibition of edema by MAIF (% of control volume ± SD) |
|---|---|---|---|---|
| 3 | −150 | 311 ± 65 | 246 ± 52 | 79 ± 17 |
| 2 | −90 | 304 ± 71 | 211 ± 33 | 73 ± 11 |
| 2 | −60 | 304 ± 71 | 186 ± 34 | 61 ± 11 |
| 1 | −30 | 391 ± 63 | 261 ± 49 | 67 ± 13 |
| 3 | −15 | 311 ± 65 | 152 ± 41 | 49 ± 13 |
| 1,2,3 | 0 | 336 ± 78 | 184 ± 42 | 55 ± 13 |
| 3 | 15 | 311 ± 65 | 218 ± 30 | 70 ± 10 |
| 1 | 30 | 391 ± 63 | 218 ± 30 | 56 ± 8 |
| 2 | 60 | 304 ± 71 | 212 ± 40 | 69 ± 13 |
| 2 | 90 | 304 ± 71 | 216 ± 37 | 70 ± 12 |
| 3 | 150 | 311 ± 65 | 261 ± 42 | 84 ± 14 |

A significant inhibition of edema was observed at all time points studied; however, the level of inhibition was less at the outer extremes (±150 min). An interesting cyclic response to MAIF administration was seen in those groups treated closer to the point of challenge. The fact that MAIF was more effective when given 30 minutes after challenge than when given 15 minutes after challenge supports the concept that the secondary, phagocytic-cell mediated, phase of the response is inhibited by the agent. The preparation of MAIF strongly inhibited the response to carrageenan when administered 15 minutes before or at the time of challenge. It is apparent, furthermore, that the agent has a relatively long half life in the serum (1–2 h) and its effectiveness is related to the time of challenge and the dynamic nature of the inflammatory response.

It is thus surmised that the anti-inflammatory effect is due to an effect on inflammatory cells, likely the neutrophils.

EXAMPLE 13

Effect of MAIF on the Reverse Passive Arthus Reaction

The possibility that the anti-inflammatory factor might affect neutrophil involvement was investigated by evaluating the ability of the material to modulate the reverse passive Arthus reaction (RPA). This immune complex-induced response is primarily neutrophil mediated and agents which affect the development of the reaction do so via an effect on these cells. To induce the RPA, rats were injected intradermally with rabbit antibody to ovalbumin and intravenously with native ovalbumin. Ovalbumin/ovalbumin-antibody immune complexes form in and around the dermal blood vessel walls, host neutrophils bind to the Fc portion of the antibody and an intense inflammatory reaction is initiated. It should be noted that, although the response is initiated by immune-complexes, it takes place independently of the host's immune system.

Three parameters are used to quantify the RPA. These are, (1) edema—measured using the accumulation of $^{125}$I-HSA, (2) hemorrhage—assessed by in vivo pre-labelling RBC's with $^{59}$Fe and (3) neutrophil accumulation—measured by determining tissue levels of the neutrophils specific enzyme myeloperoxidase (MPO). These assays are known to those of ordinary skill in the art.

Eighteen rats were divided into three groups of six. Rabbit anti-ovalbumin (40 $\mu l$) was injected intradermally at four sites on the back of each animal and 2 mg of ovalbumin injected intravenously immediately afterwards. One group of animals received no other treatment and served as controls. The second group were injected intravenously with 20 mg of a lactose preparation, while the final group were injected intravenously with 20 mg of a purified preparation of MAIF. Both lactose and MAIF preparation were administered with the ovalbumin. The severity of the reaction was assessed 3.5 hours after challenge. When the MAIF preparation was administered intravenously at a dose of 20 mg/rat prior to the initiation of the RPA response, there was a highly significant inhibition of the three parameters used to measure the response (Table 6, FIG. 20). The lactose control material also caused a modest and marginally significant suppression of neutrophil accumulation and hemorrhage. This indicates that there is a small amount of anti-inflammatory activity in normal milk.

TABLE 6

| Group | Neutrophil accumulation: Units of MPO | μl of Edema | Haemorrhage: μl of RBC |
|---|---|---|---|
| Control | 0.30 ± .157 | 107 ± 29 | 4.8 ± 3.1 |
| Lactose | 0.214 ± .176** | 104 ± 23 | 3.0 ± 1.5** |
| MAIF | 0.056 ± .013 | 60 ± 27* | 1.5 ± 1.7* |

* = p < 0.01
** = p < 0.05

As the neutrophil is the primary mediator of the RPA, these results provided additional evidence that MAIF was capable of inhibiting the inflammatory response via an effect on neutrophil function.

EXAMPLE 14

Effect of MAIF on Neutrophil Migration

In order to participate effectively in an inflammatory response, neutrophils must first migrate from the vasculature to the site of inflammation. To determine whether anti-inflammatory factor interfered with neutrophil migration, a model of inflammation employing the subcutaneous implantation of sterile polyurethane sponges was used. The sponges are removed at intervals after implantation and by weighing the sponges and then extracting and counting the cells in the infiltrate, both the fluid and cellular phase of the response can be quantified. Twenty four hours after implantation >95% of the cells found in the sponge are neutrophils.

Figure 21B:
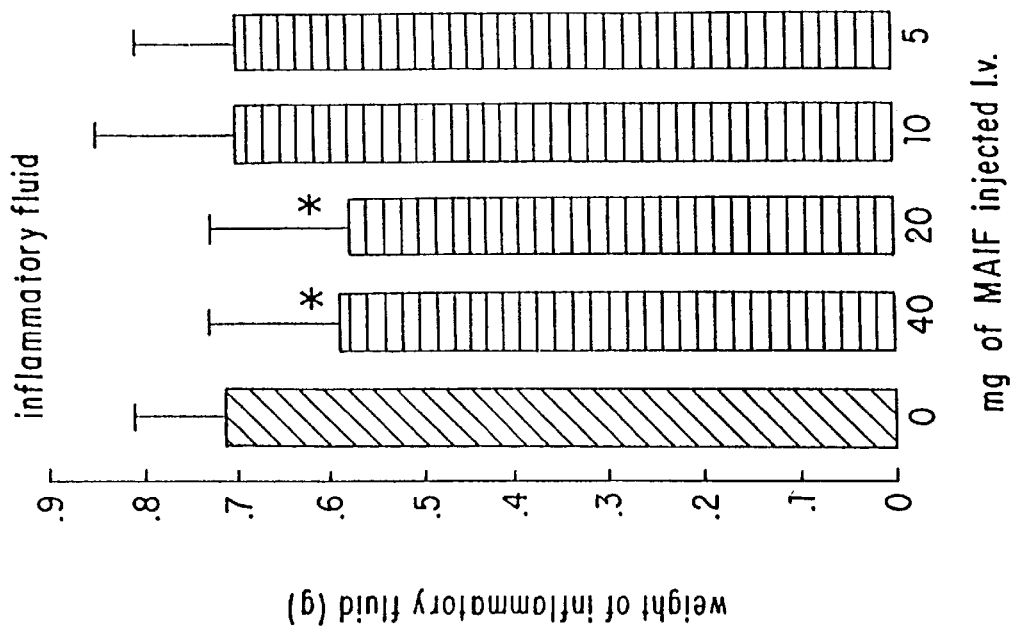
FIG. 21. Effect of decreasing doses of MAIF on the ability of neutrophils to emigrate from the vasculature into subcutaneously implanted sterile sponges. *=p<0.01.
Figure 21A:
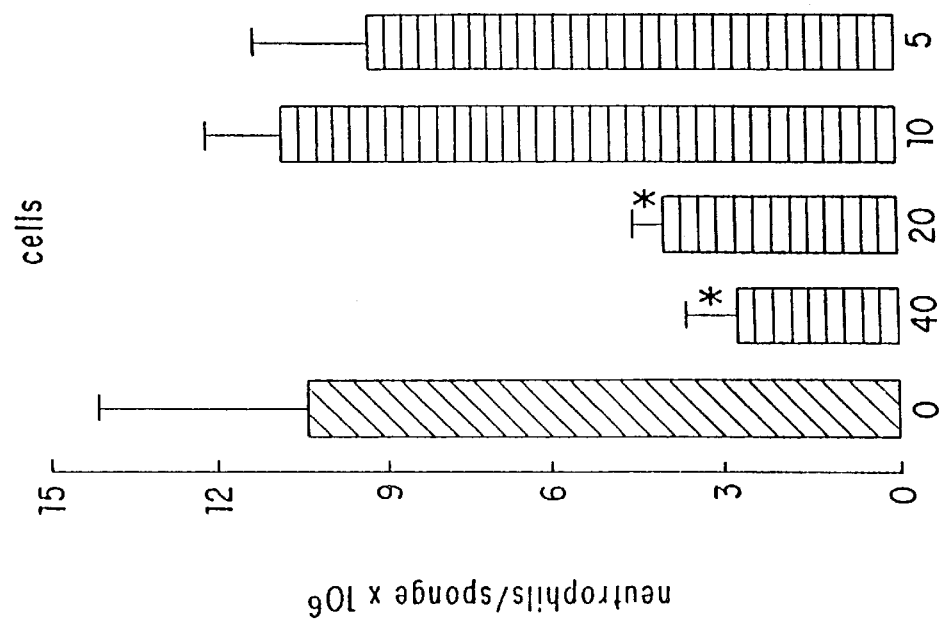

Two experiments have been carried out. In the first, animals were treated with either 5, 10, 20, or 40 mg of a purified MAIF preparation at the time of sponge implantation. Sponges were removed 24 hours after implantation. Each group consisted of between 5 and 8 rats and two sponges were implanted in each animal. The results are shown in FIG. 21.

Twenty or 40 mg of MAIF preparation, administered intravenously at the time of sponge implantation, had a marked effect on the ability of inflammatory cells to migrate. A less marked, but equally significant, inhibition of fluid accumulation was also seen. The two lower doses of MAIF had no demonstrable effect in this model of inflammation.

Figures 22A, 22B:
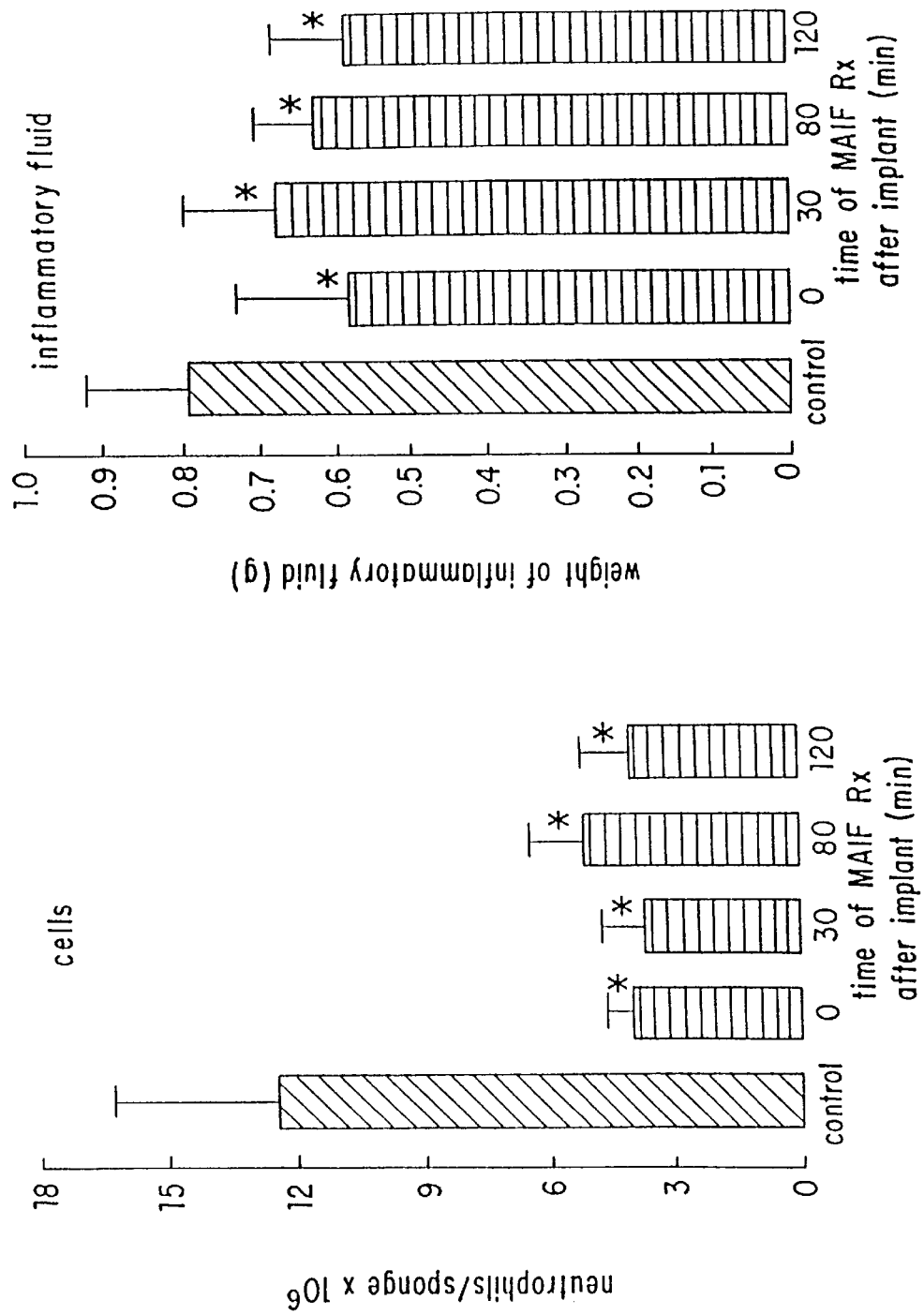
FIG. 22. Effect of MAIF, administered at a dose of 20 mg per rat, to inhibit the ability of inflammatory cells to accumulate in subcutaneously implanted sponges when administered at the time of implant or up to 120 minutes after implant. *=p<0.01.

A second experiment, designed to delineate the temporal relationship between the inflammatory challenge (sponge implantation) and MAIF administration, was carried out. In this study, 20 mg of MAIF preparation were administered intravenously 30, 60 or 120 minutes after sponge implantation. A fourth, control, group was left untreated. There were five animals in each group. Two sponges were implanted in each animal and these were removed after 24 hours. The results are illustrated in FIG. 22. Included on this graph are results obtained from a sample group of rats that received 20 mg of the MAIF preparation at the time of implantation (see FIG. 21).

Figure 23:
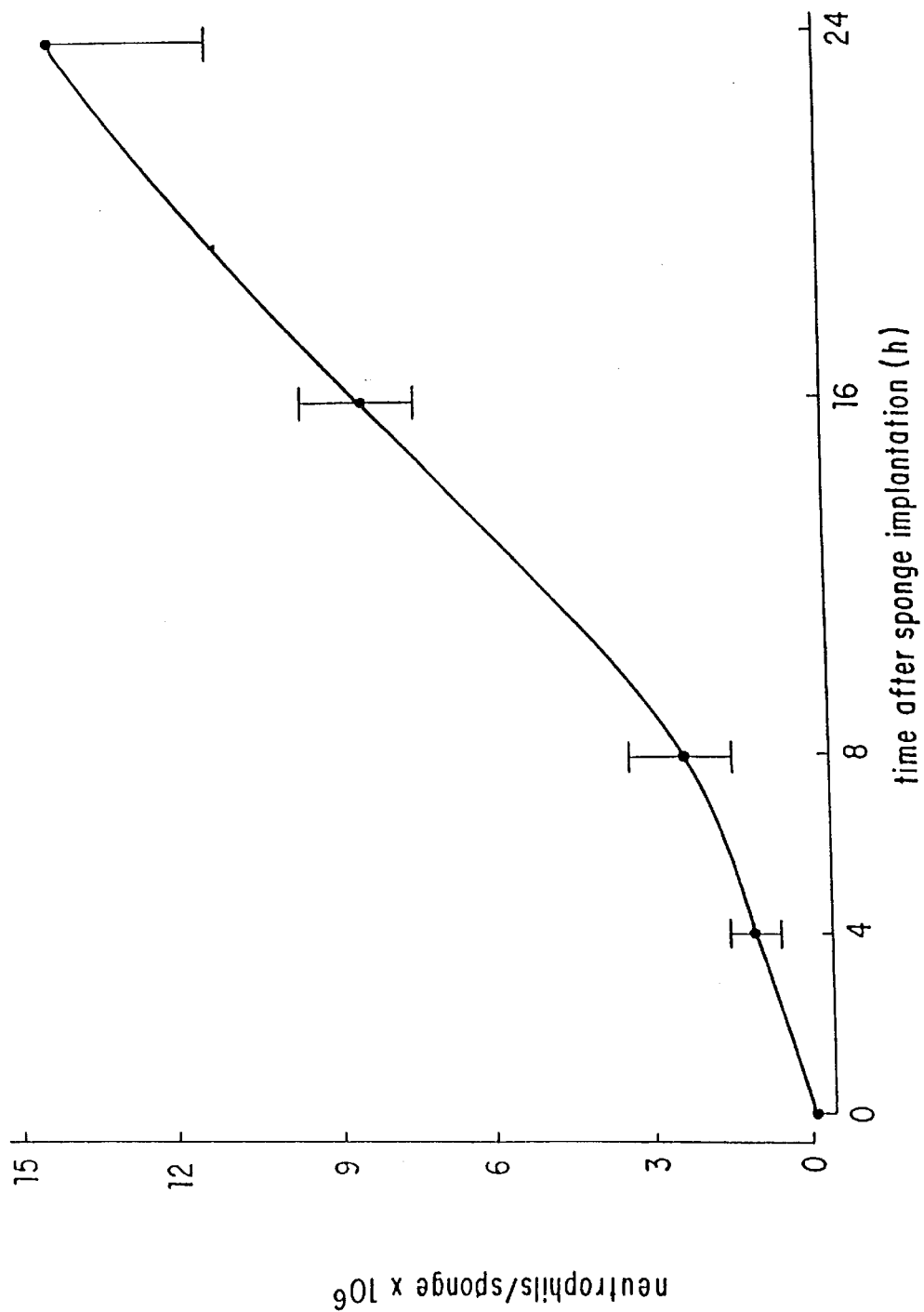
FIG. 23. Time course of the cellular inflammatory infiltration into subcutaneously implanted sponges in normal animals.

Results from the time-course of the effect of MAIF on carrageenan-induced footpad edema show MAIF to be comparatively ineffective when administered 60 minutes or later after challenge. It is noteworthy that while 20 mg of the MAIF preparation was required to suppress the inflammation associated with the sponge implantation, 4 mg was sufficient to inhibit the carrageenan-induced edema. Without intending to be held to this interpretation, this disparity may be related to the different level of provocation presented to the host by the two stimuli. The sponge implant is a relatively benign stimulus which induces a slow inflammatory response and the bulk of the cells accumulate between 8 and 16 hours after implantation (FIG. 23). On the other hand the subcutaneous injection of carrageenan is a very strong stimulant which induces a correspondingly strong response over a relatively short period (FIG. 16).

EXAMPLE 15

Alternative Method of a Purifying the Anti-Inflammatory Factor from Milk (Preparation "AIF")

The following Example describes a method for purifying the anti-inflammatory factor from milk in its lowest molecular weight, unaggregated form. The preparation resulting from the purification steps described herein has been given the designation "AIF" in order to distinguish it from the preparation obtained using the procedure described in Example 2. In the present Example and in the Example which follows (i.e. Example 16) the active factor within the preparations is referred to simply as the "anti-inflammatory factor". All of the purification steps were performed so as to minimize possible contamination with bacteria or pyrogens. Sterile water was used to prepare solutions and all glassware was depyrogenated.

Step 1: <10,00 Molecular Weight ("MW") Ultrafiltration

Fresh S100 immune skim milk (see Example 1 for a description of procedures used in obtaining the immune milk) was pumped through a 10,000 MW cutoff ultrafiltration membrane (Filtron) at a pressure of 30 psi. The permeate was collected in depyrogenated bottles maintained on ice. Permeates were sterile filtered and refrigerated until use. The <10,000 MW permeate contains the milk anti-inflammatory factor as well as low molecular weight peptides, oligosaccharides and a large amount of lactose. Anti-inflammatory activity in the permeate occurs in a low molecular weight, unaggregated form.

Step 2: DEAE-Sepharose Chromatography

Initial fractionation of anti-inflammatory activity was performed on DEAE-Sepharose. A 5×50 cm column containing one liter of DEAE-Sepharose was equilibrated with permeate buffer. Permeate buffer is a sterile, endotoxin-free solution containing the diffusible ions found in bulk milk in the appropriate concentrations. Permeate buffer contains $CaCl_2$, $MgCl_2$, NaCl, NaCitrate and $NaH_2PO_4$. Typically, approximately eight liters of <10,000 MW permeate were pumped onto the DEAE-Sepharose column at a flow rate of about 500 ml per hour. Column eluate was monitored at 280 nm. The column was washed with distilled water until the 280 absorbance returned to baseline (about 6 to 8 liters of distilled water were typically required). Anti-inflammatory activity was bound to the column and was eluted with about 4 liters of 0.5 M ammonium acetate in water, pH 7.4. The eluate was lyophilized to dryness and weighed. The weight of recovered material obtained from eight liters of permeate was typically between 15 and 20 grams. Since ammonium acetate is completely volitized during lyophilization, the residual weight represents the weight of bound material. Anti-inflammatory activity was assayed in the mouse neutrophil migration inhibition assay.

Step 3: H-40 Chromatography

The material eluted from the DEAE-Sepharose column was further fractionated on a sizing column in order to separate the factor responsible for anti-inflammatory activity from other low molecular weight components. Eight grams of the DEAE sample was dissolved in 50 ml of distilled water and applied to a 2.5×150 cm column containing 736 ml of Toyopearl HW-40 (Rohm and Haas) equilibrated in water. The column was developed in distilled water at a flow rate of 40 ml per hour and eluate was monitored at 280 nm. Fractions were collected and assayed for anti-inflammatory activity in the mouse neutrophil migration inhibition assay. Fractions evidencing activity and minimal absorbance at 280 nm were pooled and lyophilized. Approximately 80 mg of material containing anti-inflammatory activity was recovered from eight liters of permeate.

Step 4: AffiGel 601 Chromatography

The final purification step involved affinity chromatography of the active factor in a column packed with a boronate-derivatized polyacrylamide based medium (AffiGel 601, Bio-Rad) which has an affinity for coplanar adjacent cis hydroxyl groups. Forty mg of low molecular weight HW-40 derived material was equilibrated in 10 ml of 0.25 M ammonium acetate, pH 7.0, and applied to the AffiGel column which had also been equilibrated in 0.25 ammonium acetate. Eluate was monitored at 280 nm. The column was washed with 400 ml of 0.25 M ammonium acetate at a flow rate of 50 ml per hour until the 280 nm absorbance decreased to background. The AffiGel column was then eluted with 1600 ml of 0.1 M formic acid, pH 2.8. The eluate was tested for activity in the mouse neutrophil migration inhibition assay and lyophilized to dryness. Approximately 8 to 10 mg of bound material containing anti-inflammatory activity was recovered from 8 liters of permeate.

The preparation obtained by this method is given the designation "AIF". The preparation was substantially purified with respect to the anti-inflammatory factor but is not homogeneous. The preparation exhibits anti-inflammatory activity in the mouse neutrophil migration inhibition assay, in the rat paw edema assay, in the rat ear swelling assay and blocks neutrophil binding to rat mesentery venule endothelium (visualized by intravital microscopy). Based upon comparative analyses in the mouse neutrophil migration inhibition assay, AIF is approximately 55,000 fold more purified than the original skim milk <10,000 MW permeate.

EXAMPLE 16

Effect of Preparations of Anti-inflammatory Factor on the Adhesion of Neutrophils to Endothelial Cells and on the Emigration of Neutrophils from the Vasculature The effect of the anti-inflammatory factor on the adhesion of neutrophils to endothelial cells and on the emigration of neutrophils from the vasculature was tested. Two different preparations of anti-inflammatory factor were used. One preparation was made using the purification procedure described in Example 2. For the purposes of the present Example, this preparation is referred to simply as "MAIF". The other preparation of anti-inflammatory factor was made using the purification procedure described in Example 15 and is referred to both in that Example and in the present Example as "AIF". It is to be understood that both MAIF and AIF contain within them the anti-inflammatory factor at different states of purity.

Chemicals:

Human serum albumin, trypsin, platelet-activating factor (PAF), phorbol myristate acetate (PMA), propidium iodide, and Histopaque were obtained from Sigma Chemical Co., St. Louis, Mo. Human Neutrophil elastase was purchased from Calbiochem. A murine anti-human CD18 monoclonal antibody ($IgG_1$-subclass; FITC conjugate) and a murine anti-keyhole limpet hemocyanin ($IgG_1$-subclass; FITC conjugate), used as a negative control antibody, were purchased from Becton Dickinson Systems Inc., Mountain View, Calif. Simply Cellular™ Microbeads were purchased from Flow Cytometry Standards Corp., Research Triangle Park, N.C. Other reagents were the best grade commercially available and were used without further purification.

In Vivo Methods:

Intravital microscopy experimentation. Twenty-four male Wistar rats (180–250 g) were maintained on a purified laboratory diet and fasted for 24 hr prior to surgery. The animals were initially anesthetized with pentobarbital (12 mg/100 g body weight). A right carotid artery and jugular vein were cannulated to measure systemic arterial pressure (Statham P23A pressure transducer and a Grass physiologic recorder) and drug administration respectively. A midline abdominal incision was made and the animals were placed in a supine position. A segment of the mid-jejunum was exteriorized through the abdominal incision and all exposed tissue was covered with saline soaked gauze to minimize tissue dehydration. The mesentery was carefully placed over an optically clear viewing pedestal that allowed for transillumination of a 2 $cm^2$ segment of tissue. The temperature of the pedestal was maintained at 37° C. with a constant temperature circulator (Fisher Scientific, model 80). Rectal and mesenteric temperatures were monitored using an electrothermometer. The mesentery was suffused with warmed bicarbonate-buffered saline (pH 7.4). An intravital microscope (Nikon Optiphot-2, Japan) with an X25 objective lens (Leitz Wetzlar L25/0.35, Germany) and X10 eyepiece was used to observe the mesenteric microcirculation. A video camera mounted on the microscope projected the image onto a color monitor and the images were recorded for playback analysis using a video cassette recorder. Single unbranched venules with diameters ranging between 25 and 40 $\mu$m were selected for study. Venular diameter was measured on line using a video caliper. The number of adherent and emigrated neutrophils was determined off-line during playback of videotaped images. A neutrophil was considered adherent to venular endothelium if it remained stationary for 30 seconds or more. Rolling neutrophils were defined as those white blood cells that moved at a velocity less than that of erythrocytes in the same vessel. Leukocyte rolling velocity was determined by the time required for a leukocyte to traverse a given distance along the length of the venule.

Experimental protocol. After all hemodynamic parameters were in steady state, images from the mesentery were recorded for 5 minutes. The mesentery was then superfused for 60 minutes with 100 nM PAF in the presence of either 40 or 5 mg/rat of the MAIF preparation (iv.). Measurements of aforementioned parameters were again performed at 30 and 60 min of PAF superfusion. In two experimental groups, the mesenteric preparations were again exposed to PAF as described above but, at 30 minutes, they received either 40 or 5 mg/rat of the MAIF preparation. In three additional experiments, the AIF preparation was given either as a pretreatment or as a post-treatment.

In Vitro Methods

Isolation of Neutrophils. Neutrophils from healthy donors were purified by dextran sedimentation followed by hypotonic lysis and Histopaque centrifugation. Except for the dextran sedimentation step, which was performed at room temperature, the cells were kept at 4° C. throughout the isolation procedure. Cell preparations contained 95% neutrophils and greater than 99% of these were viable as determined using Trypan Blue. After isolation, neutrophils were resuspended at a final concentration of $2\times10^6$ cells/ml in phosphate buffered saline (PBS). Aliquots of cells were then incubated at 37° C. for 20 minutes with varying concentrations of either the MAIF or the AIF preparation. After washing, neutrophils were incubated in the dark at 4° C. for 30 minutes with saturating concentrations of fluorescein-conjugated murine anti-human CD18, human CD11b, IGG coated microbeads (Simply Cellular™ microbeads) or the murine negative control antibody.

Immunofluorescence Staining and FACS Analysis. Direct immunofluorescence as a measure of CD18 surface expression was determined by analysis on a FACScan (Becton Dickinson Systems Inc., Mountain View, Calif.) using the channel number (log scale) representing the mean fluorescence intensity of 10,000 cells. The logarithmic channel numbers were converted to linear values using methods well-known in the art. The specific mean fluorescence intensity for cells stained by CD18 antibodies was calculated after subtracting the mean fluorescence intensity of the cells exposed to the negative control antibody. Non-viable cells were screened out using propidium iodide.

Superoxide Assay. Superoxide production from isolated neutrophils was measured following PMA and N-formyl-Met-Leu-Phe ("fMLP") stimulation in the presence of various concentrations of MAIF. The reduction of cytochrome C by activated neutrophils was measured using a spectrophotometer (Hitachi U2000) at 550 nm. Briefly, sample was added to two cuvettes and one cuvette was used as a reference. The latter contained superoxide dismutase (superoxide scavenger). Neutrophils were allowed to equilibrate at 37° C. for 5 min in the presence of various concentrations of MAIF and the cells were then stimulated with either PMA or FMLP. Superoxide production was measured for 3 min.

Protease Release. $^{125}$I-labelled albumin was coated onto wells and allowed to dry overnight. Unbound albumin was washed and then PMA-stimulated neutrophils were incubated within the wells for one hour in the presence or absence of various concentrations of MAIF. Free radioactivity within the supernatant of the wells was divided by total radioactivity within each well to assess the level of proteolysis.

Figure 24:
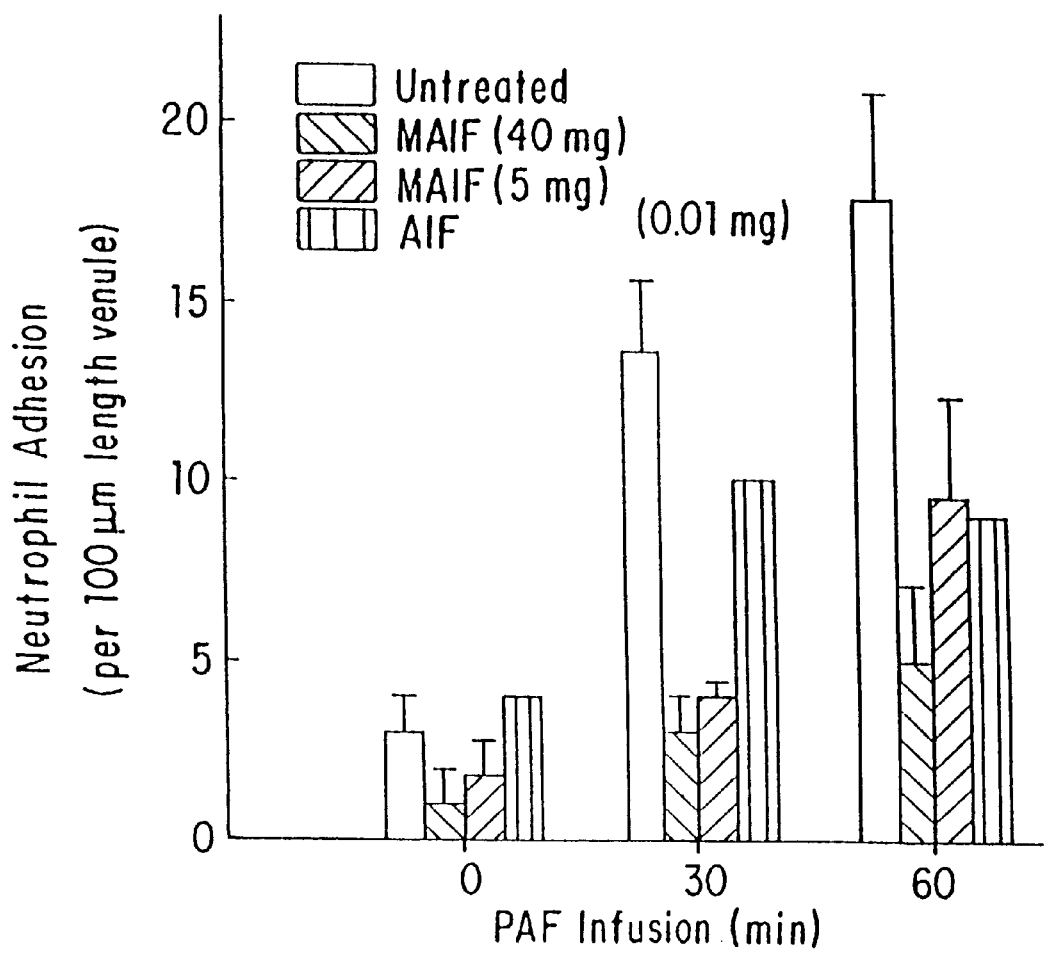
FIG. 24. Effect of preparations of anti-inflammatory factor on platelet-activating factor (PAF) induced adhesion of neutrophils to venules.
Figure 25:
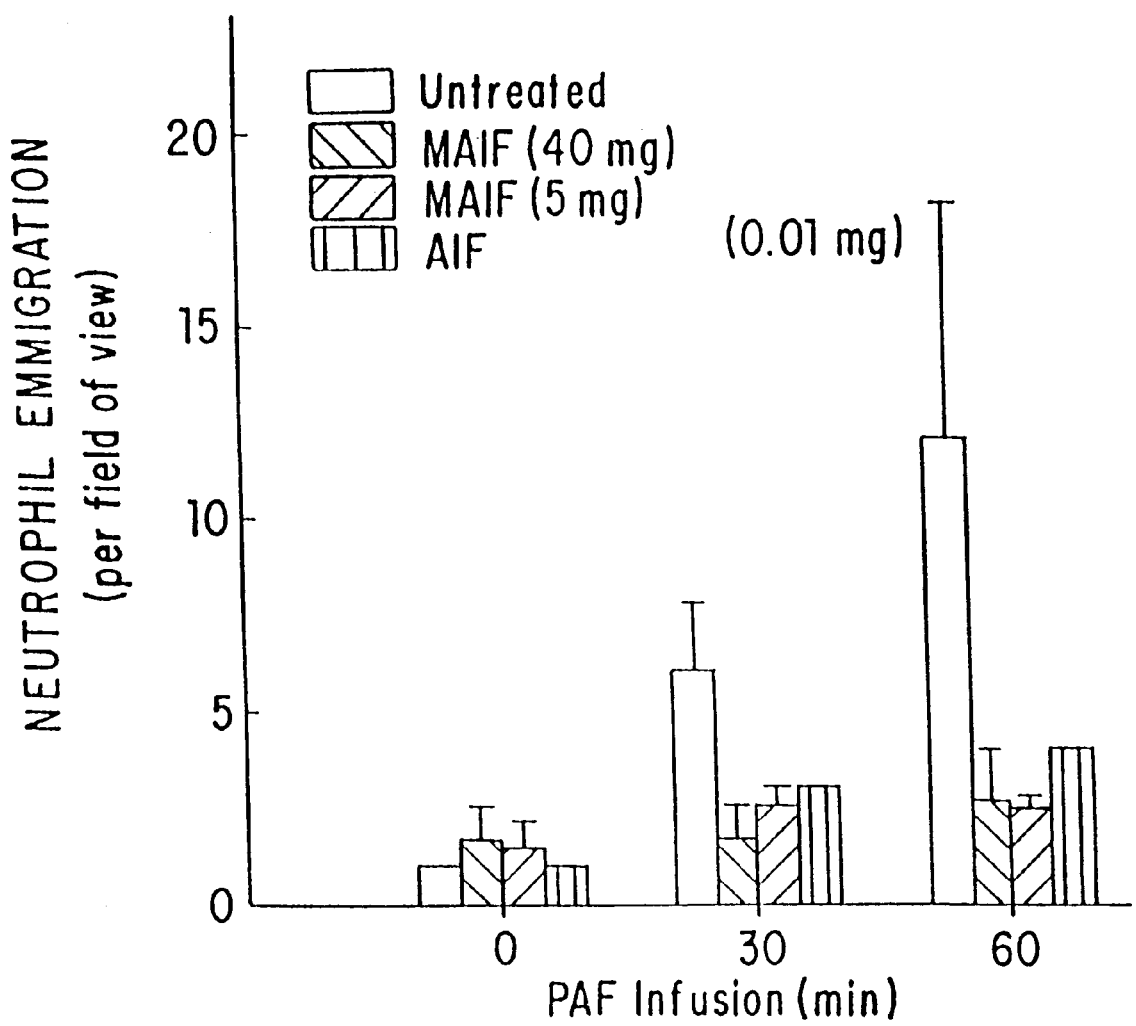
FIG. 25. Effect of preparations of anti-inflammatory factor on PAF-induced neutrophil emigration.
Figure 26:
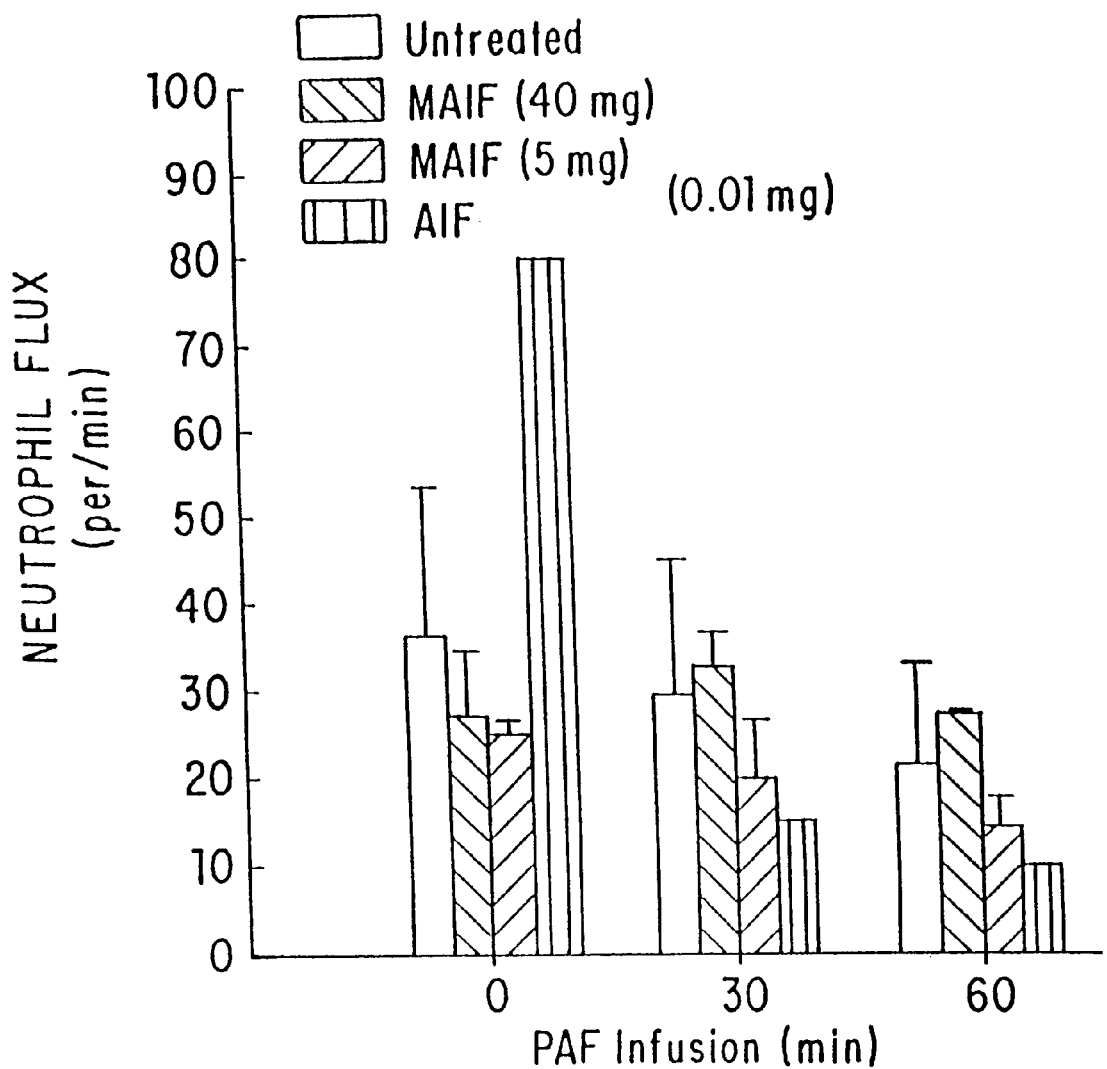
FIG. 26. Effect of preparations of anti-inflammatory factor on PAF-induced flux of neutrophils through venules.

Results:

Results are summarized in FIGS. 24–30 and Tables 7–9. FIG. 24 demonstrates that PAF superfusion increased neutrophil adhesion to postcapillary venules approximately 6-fold over a 60 min period. 40 mg/rat of the MAIF preparation reduced the PAF-induced neutrophil adhesion by more than 90% at 30 minutes and by more than 80% at 60 minutes. Interestingly, MAIF pretreatment seemed to also reduce the number of adherent neutrophils prior to exposure of PAF. The lower concentration of MAIF (5 mg per rat) was less effective, reducing leukocyte adhesion by 50% at 60 min. The AIF preparation at a concentration of 0.01 mg per rat was found to reduce leukocyte adhesion by about 50% at 60 min. At a tenfold higher concentration of AIF, a very large increase in leukocyte adhesion was observed (data not shown). The adhesion was so dramatic that the videotape could not be analyzed. FIG. 25 shows the effect of MAIF and AIF on neutrophil emigration. MAIF at a concentration of 40 mg per rat and 5 mg per rat and AIF at a concentration of 0.01 mg per rat were found to completely prevent the increase in neutrophil emigration with time of PAF exposure. Neutrophil flux did not appear to change significantly in the MAIF treated group compared with the untreated group (FIG. 26). When AIF was given, we initially observed more neutrophils rolling than usual, however the number decreased with time.

Figure 27:
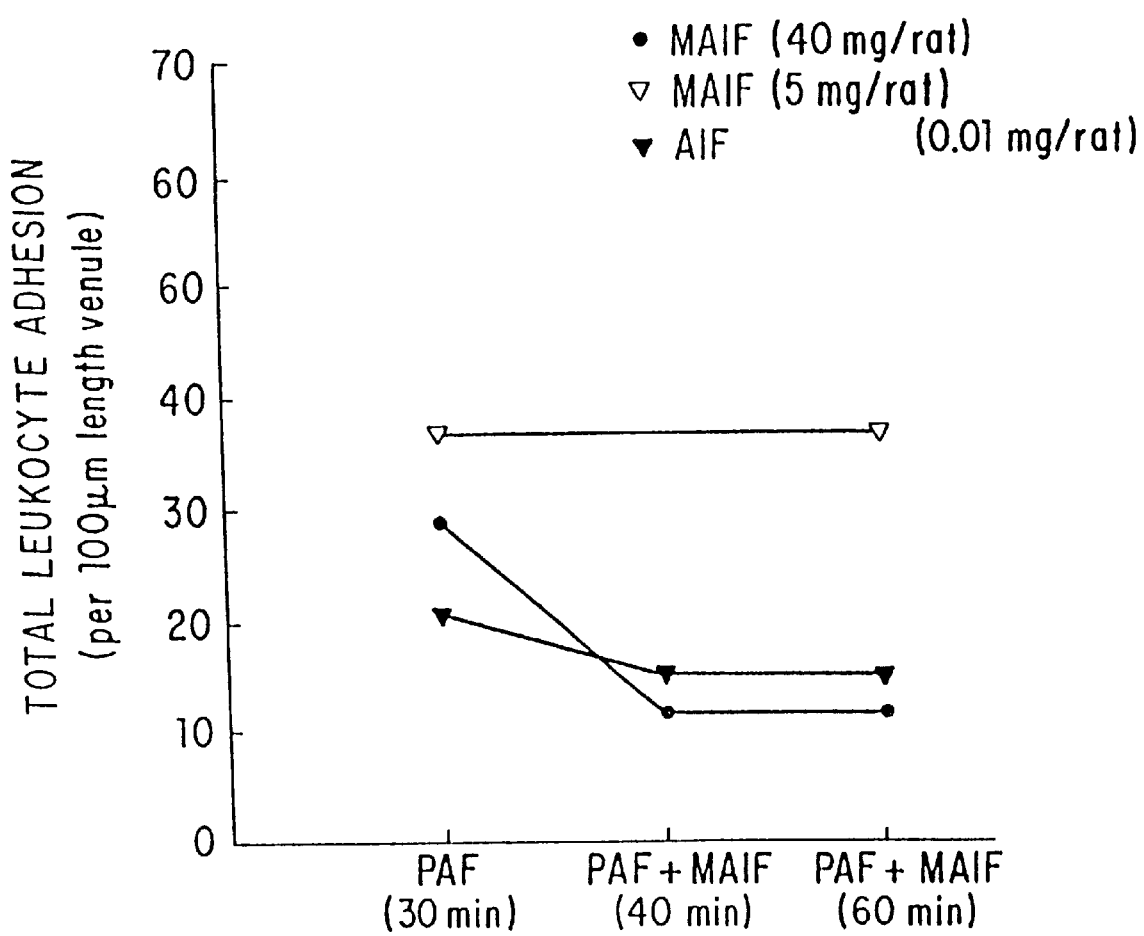
FIG. 27. Reversal of neutrophil adhesion by preparations of anti-inflammatory factor. 27a shows the effect of the MAIF preparation (40 mg/rat) in reducing the number of neutrophils adhering to venules in response to PAF. 27b shows the effect of the MAIF preparation (40mg/rat) on new neutrophil-endothelial cell adhesions.
Figure 27A:
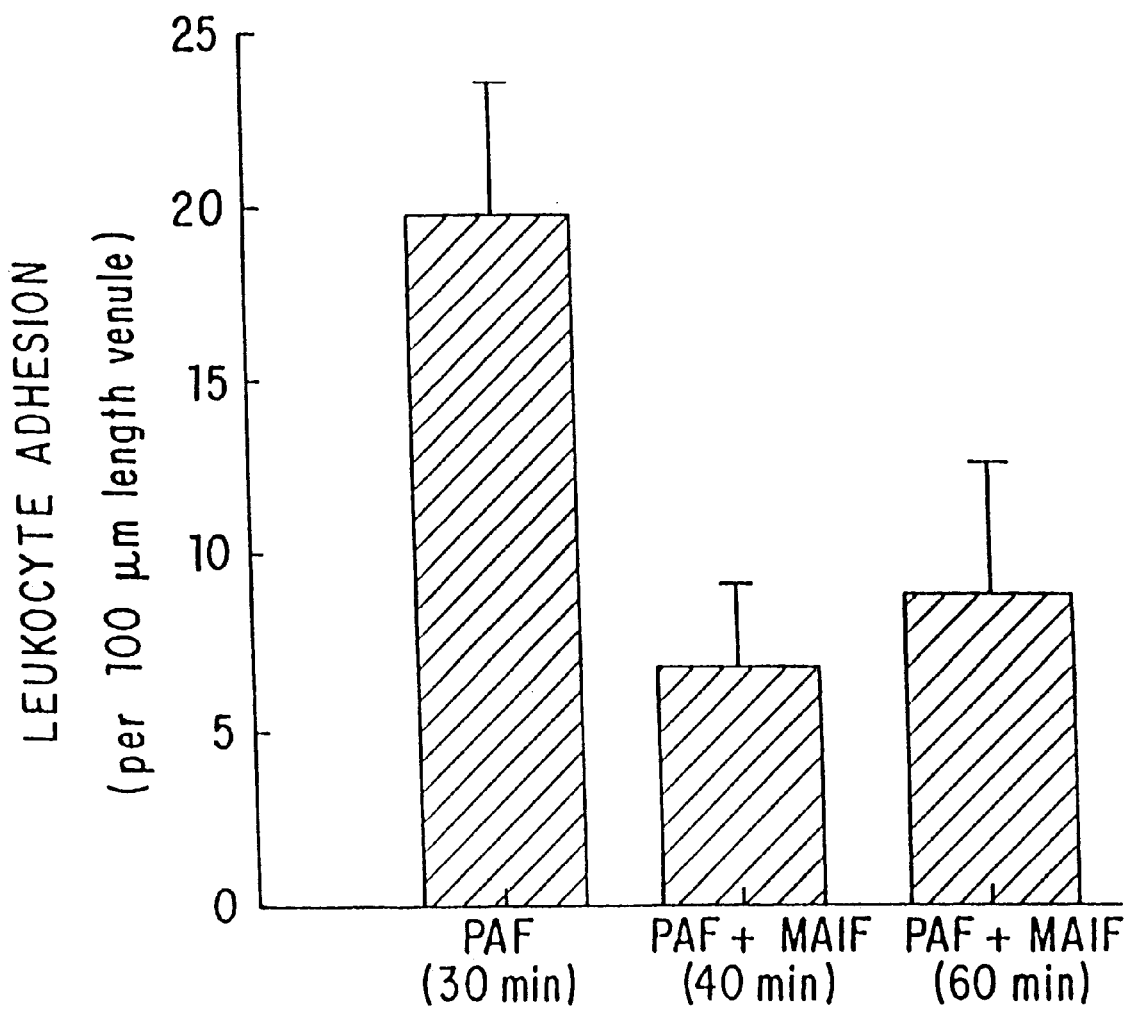
Figure 27B:
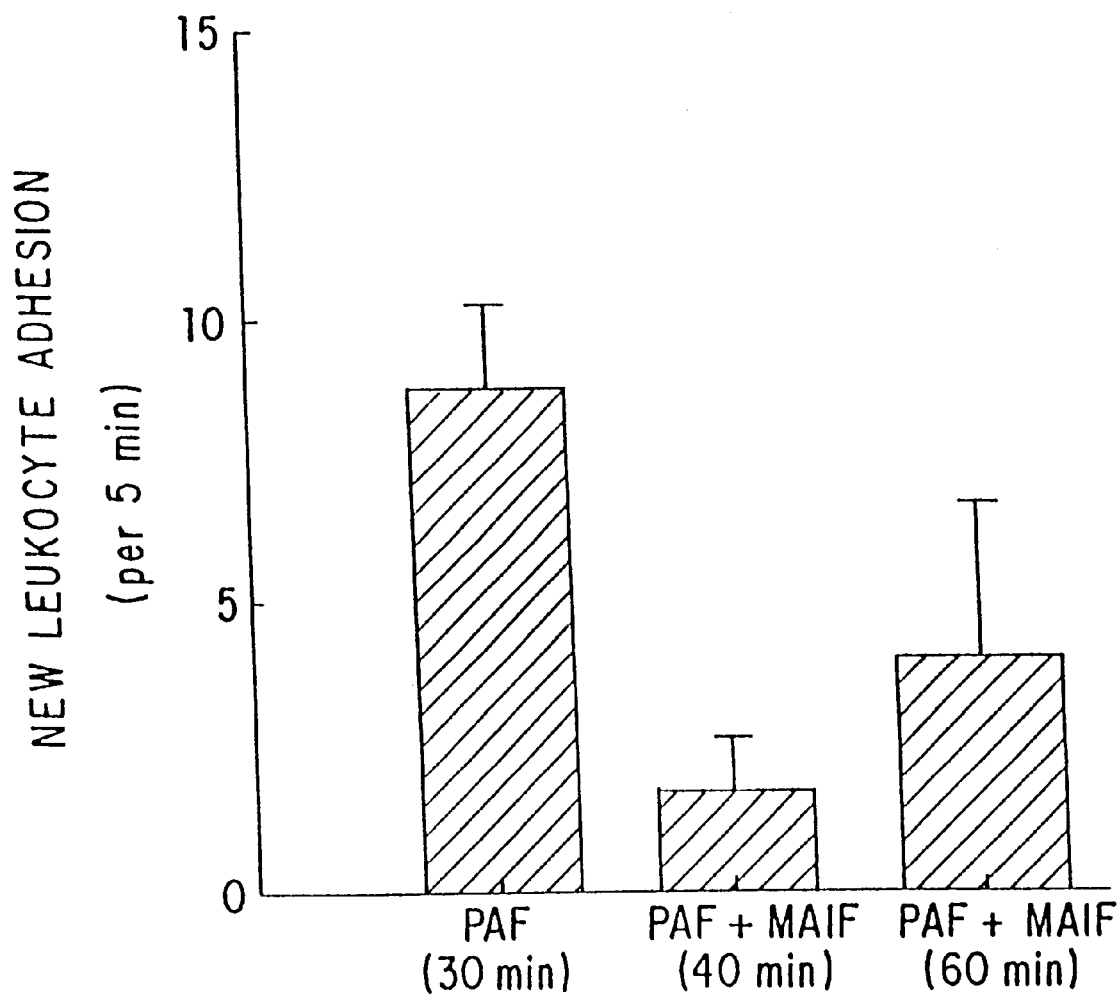
Figure 28:
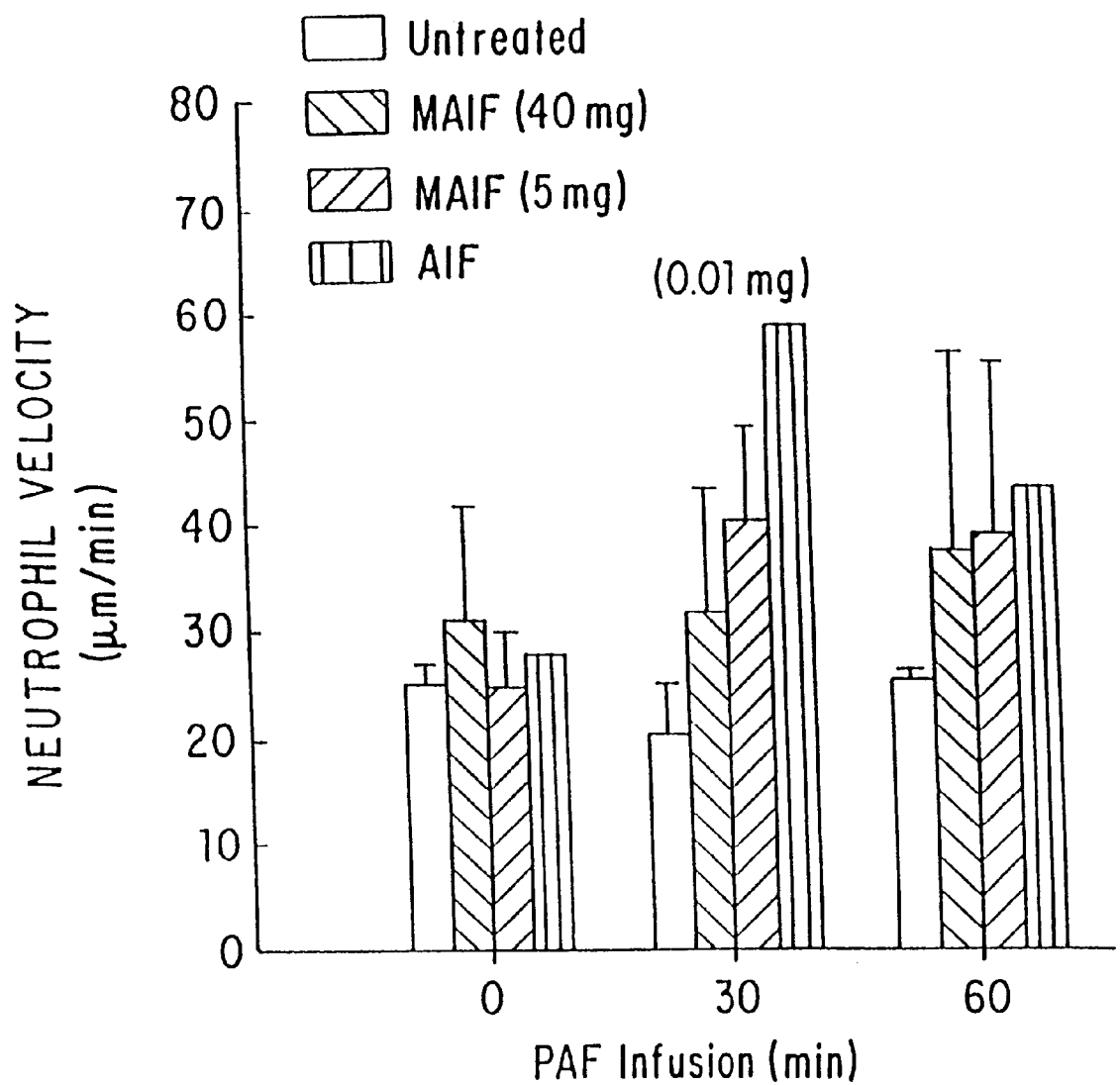
FIG. 28. Effect of preparations of anti-inflammatory factor on the velocity of neutrophils in venules.
Figure 29:
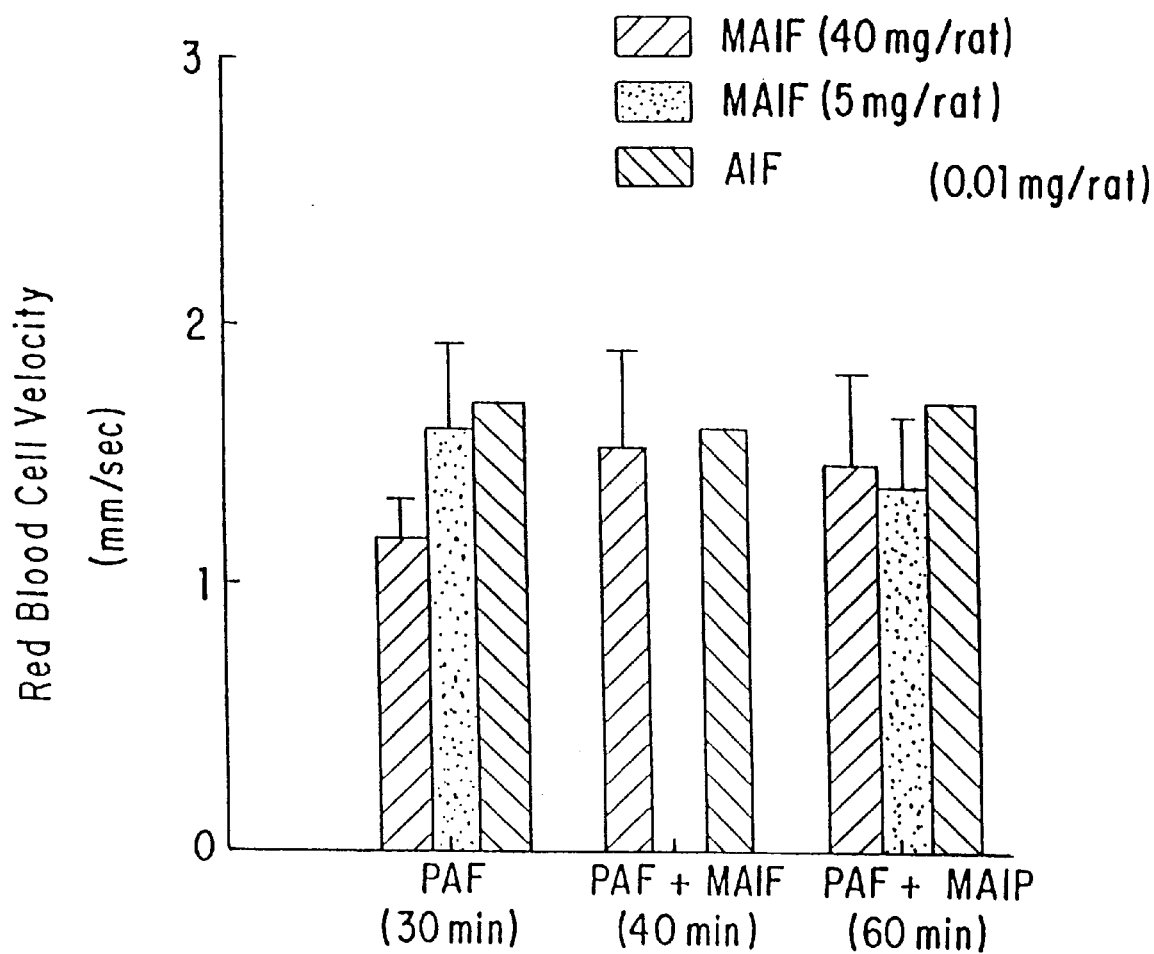
FIG. 29. Effect of preparations of anti-inflammatory factor on the velocity of red blood cells in venules.
Figure 30:
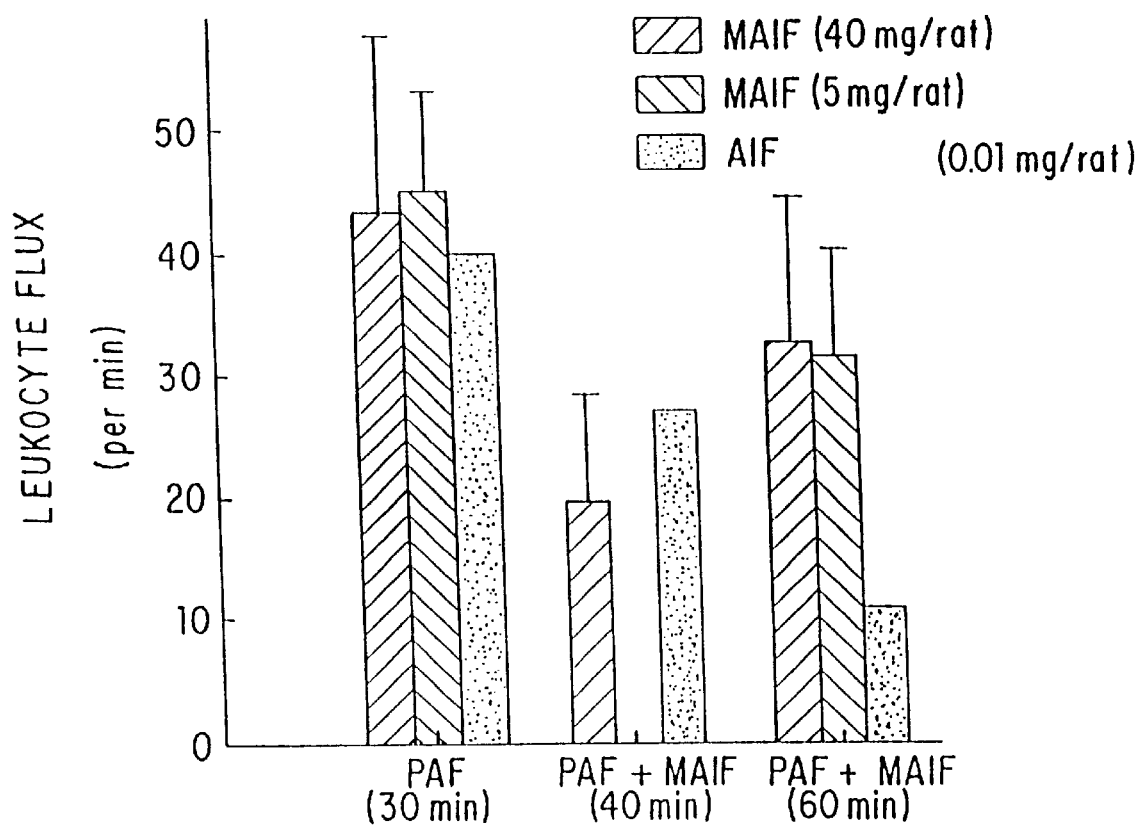
FIG. 30. Effect of anti-inflammatory factor on leukocyte flux in venules.

In a second series of experiments, the various anti-inflammatory agents were administered after neutrophils were already adherent (FIG. 27). In this series of experiments, leukocyte adhesion was reversed by an MAIF dose of 40 mg/rat but not by a dose of 5 mg/rat. AIF at a dose of 0.01 mg per rat reversed neutrophil adhesion by approximately 25%. To further assess the effect of the higher concentration of MAIF (40 mg/rat), the number of adherent neutrophils at the start of the recording procedure and the number of new neutrophils that adhered over 5 min at each period were examined. FIG. 27a demonstrates that there were fewer neutrophils adherent following 10 min of MAIF administration indicating that the anti-inflammatory factor had actually "peeled off" adherent neutrophils. Moreover, FIG. 27b clearly demonstrates that MAIF blocked new neutrophil-endothelial cell adhesions. The speed with which neutrophils rolled along the length of venules did not change between groups or with time with the exception that AIF may have increased neutrophil rolling velocity (FIG. 28). This effect was rather interesting in light of the fact that red blood cell velocity remained unchanged (FIG. 29). The results suggest that a simple increase in hydrodynamic forces cannot explain the increase in neutrophil rolling velocity. Neutrophil flux also was unaffected by MAIF but was again reduced by AIF (FIG. 30).

In vitro data indicates that the anti-inflammatory factor does not interfere with the activation of neutrophils per se. The superoxide radical scavenger, superoxide dismutase completely blocked cytochrome c reduction by PMA and fMLP-stimulated neutrophils, suggesting that this is a superoxide-mediated process. MAIF at extremely high concentrations only minimally affected cytochrome c reduction, suggesting that MAIF does not directly scavenge superoxide (Table 7). Protease release was not affected by MAIF (data not shown).

It was found that the binding of anti-CD18 monoclonal antibody could be reduced with MAIF or AIF (Table 8). This did not occur with the CD11b antibody. Binding of CD18 antibody to IgG coated microbeads was also not affected by the MAIF or AIF preparations suggesting that the anti-inflammatory factor was not affecting the ability of the anti-CD18 monoclonal antibody to bind to substrate but was, more likely, acting upon the ligand, CD18. The same pattern was observed with stimulated neutrophils (Table 9). It should be noted that the binding to CD18 varied between days because different cells were used each day. Therefore, a direct comparison of the results in Table 8 with those in Table 9 cannot be made.

TABLE 7

Effect of MAIF on Superoxide Secretion by Cells

| MAIF | PMA-Stimulated Superoxide Production (nmole/min/$10^7$ cells) | fMLP-Stimulated Superoxide Production (nmole/min/$10^7$ cells) |
|---|---|---|
| 0.0 mg/ml | 153 | 55 |
| 0.1 mg/ml | 145 | 50 |
| 1.0 mg/ml | 143 | 40 |
| 5.0 mg/ml | 140 | 32 |
| 10.0 mg/ml | 127 | — |

TABLE 8

Effect of Anti-Inflammatory Factor on the Availability of CD18 and CD11 Cell Surface Antigens

| Unstimulated Neutrophils | Mean Channel Fluorescence Anti-CD18 Antibody | Mean Channel Fluorescence Anti-CD11 Antibody |
|---|---|---|
| Neutrophils alone | 314.24 | 1594.57 |
| +0.1 mg/ml MAIF | 234.26 | 1553.74 |
| +1.0 mg/ml MAIF | 262.78 | 1796.00 |
| +0.1 µg/ml AIF | 248.28 | 1577.04 |
| +1.0 µg/ML AIF | 188.93 | 1554.61 |
| Beads + Anti-CD18 Antibody | | 60.03 |
| +1 mg/ml MAIF | | 88.61 |
| +1 mg/ml AIF | | 84.99 |

TABLE 9

Effect of MAIF on the Availability of CD18 Cell Surface Antigens on Stimulated and Unstimulated Neutrophils

| | Mean Channel Fluorescence |
|---|---|
| Unstimulated Neutrophils | 236.95 |
| + MAIF 1 mg/ml | 216.08 |
| + MAIF 5 mg/ml | 251.51 |
| Stimulated Neutrophils | 266.69 |
| + MAIF 1 mg/ml | 158.68 |
| + MAIF 5 mg/ml | 171.96 |

Discussion:

The data in the above Example suggests that the anti-inflammatory factor prevents neutrophil adhesion and emigration in venules in a dose-dependent manner. More importantly however, the anti-inflammatory factor could, within a brief period (10 min), reverse neutrophil adhesion to these vessels. The only other agents that cause adherent neutrophils to release their hold on the endothelium with such efficiency are monoclonal antibodies directed against the CD11/CD18 glycoprotein complex on the neutrophil. MAIF did not appear to have any effect on blood flow through the individual vessels or on systemic blood pressure, suggesting that hemodynamic factors such as shear stress could not account for the reversal of leukocyte adhesion. Although leukocyte rolling appears to be a prerequisite for leukocyte adhesion, MAIF did not effect leukocyte rolling velocity or leukocyte flux. The latter result suggests that the anti-inflammatory factor did not affect the number of neutrophils that rolled through the vessel and therefore, that the reduction in adherent leukocytes was not a result of fewer leukocytes interacting with the endothelium. The fact that leukocyte rolling velocity as well as leukocyte flux remained unchanged suggests that adhesion molecules on neutrophils and endothelium responsible for leukocyte rolling (1L-selectin, P-selectin) were not affected by the anti-inflammatory factor in the MAIF preparation.

It has been reported that the leukocyte may regulate its own adhesion by releasing superoxide as well as proteases. It was therefore conceivable that the lack of leukocyte adhesion in the presence of MAIF and AIF was due to the ability of these preparations to block the release superoxide or proteases. This possibility is untenable in light of the fact that MAIF had little effect on superoxide or protease release and did not interact with released proteases or scavenge released superoxide. Moreover, the MAIF did not appear to affect neutrophil viability as assessed with propidium iodide making a direct cytotoxic effect of the anti-inflammatory factor on neutrophils unlikely.

For a neutrophil to adhere and emigrate it must have an intact CD11/CD18 glycoprotein complex. Immunoneutralization of the adhesion complex completely impairs the ability of the neutrophil to permanently adhere to the endothelium and emigrate into the surrounding tissue. Since neutrophil adhesion and emigration is a rate limiting step in the tissue injury associated with a number of inflammatory conditions, an agent that interferes with these processes would also likely block the inflammatory response. In the present study, both MAIF and AIF dramatically reversed neutrophil adhesion and blocked neutrophil emigration induced by PAF. Because of the similarity between AIF-, MAIF- and anti-CD18 monoclonal antibody induced reversal of neutrophil adhesion, it seemed possible that the anti-inflammatory factor within AIF and MAIF exerted its effect by directly interacting with the CD18 glycoprotein complex. The in vitro data presented above supports this view, in that both AIF and MAIF blocked the ability of an anti-CD18 antibody to bind to the CD18 glycoprotein complex. In contrast, neither AIf nor MAIF affected the binding of CD11b to its respective monoclonal antibody. Finally, the AIF and MAIf preparations did not interfere with the ability of the anti-CD18 monoclonal antibody to bind to IgG-coated microbeads. Therefore, it can be concluded that the anti-inflammatory factor interacts with the CD18 complex directly and prevents CD18 from binding to various ligands, including endothelial cell adhesion molecules.

EXAMPLE 17

Effect of MAIF on Circulating Leucocytes

Several pharmacological agents can inhibit neutrophil migration. While some, such as cyclophosphamide, are cytoreductive and act by inhibiting hemopoiesis in the bone marrow, other agents, such as steroids and the non-steroidal anti-inflammatory drugs, have specific sites of action and do not result in leucocytosis. It was important therefore to determine the effect of the anti-inflammatory factor on circulating white blood cell numbers and ratios.

Figure 31B:
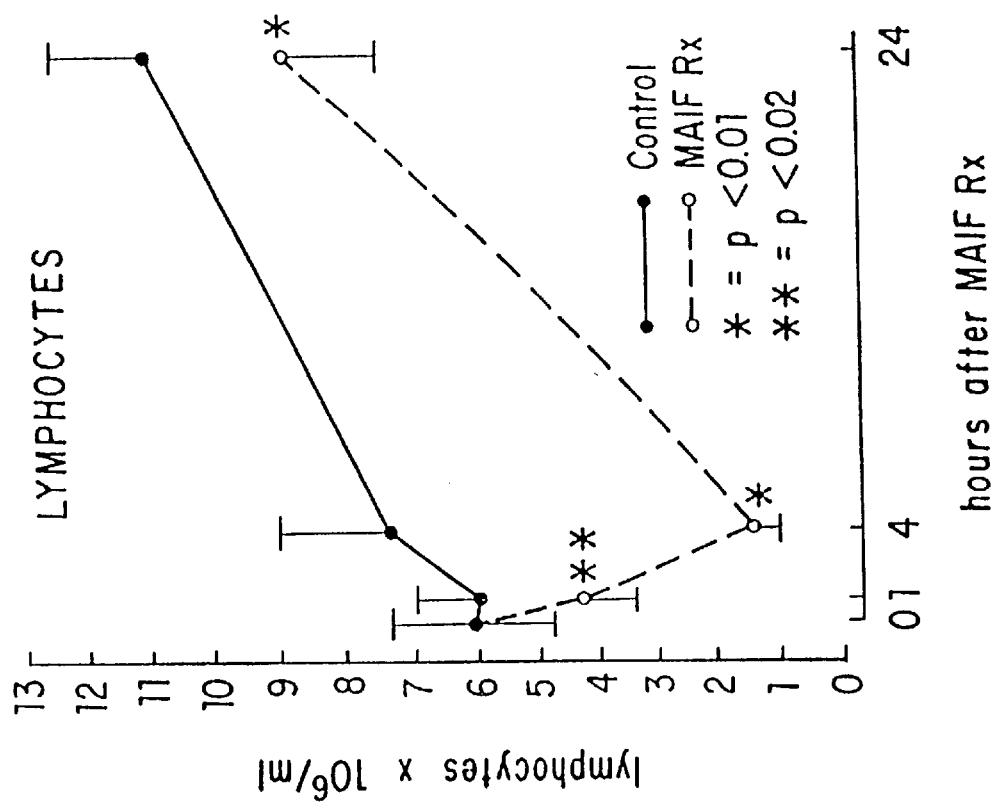
FIG. 31. Effect of 40 mg of the MAIF preparation administered i.v. on the number of circulating neutrophils and lymphocytes in the 24 hours following injection.
Figure 31A:
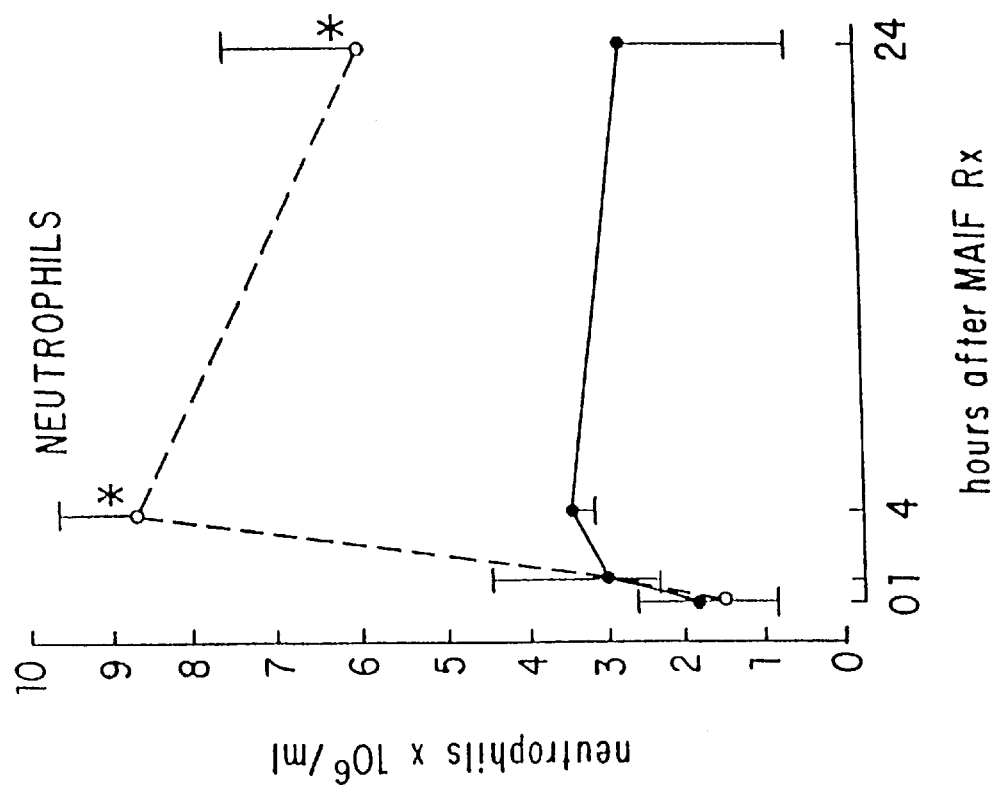

Two experiments were done. In the first, the MAIF preparation was administered intravenously at a dose of 40 mg/rat to one group of 6 animals and a control group was injected with saline. Blood samples were obtained at baseline, 1, 4, and 24 hours after treatment. The results are summarized in FIG. 31.

Figure 32:
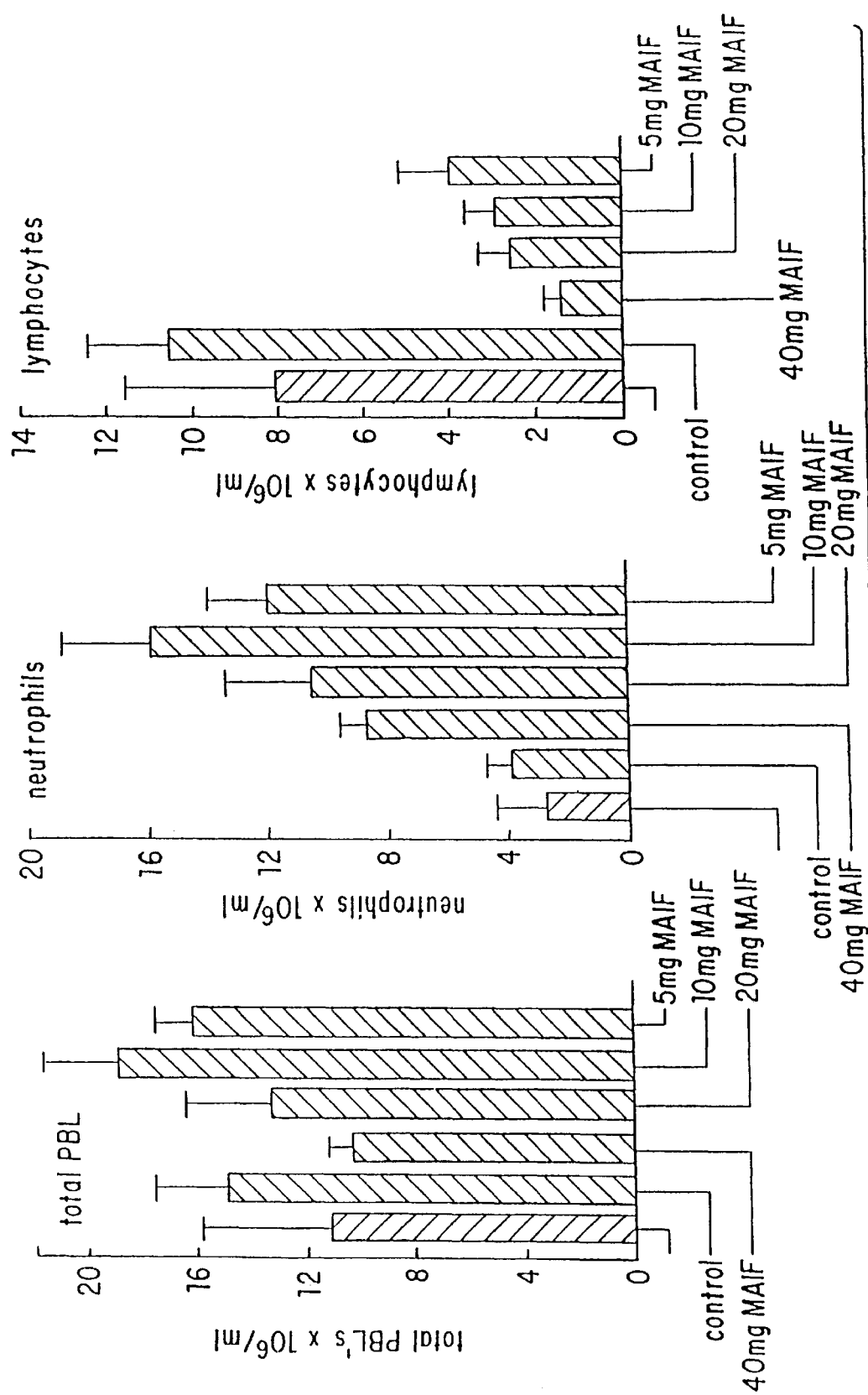
FIG. 32. Dose-response relationship between i.v. administration of the MAIF preparation and circulating leukocyte numbers (p<0.01).

MAIF administration resulted in an increase in circulating neutrophil numbers, maximal at 4 hours, and a corresponding decrease in the number of peripheral blood lymphocytes. A further dose-response study was carried out in which a group of rats were injected intravenously with saline, 5, 10 or 20 mg of the MAIF preparation. Blood from each rat had been taken 7 days previously to provide baseline values and was taken again 4 hours after the injection of MAIF. The results are shown in FIG. 32. Included on the graph are the results obtained from the sample taken 4 hours after the administration of 40 mg the MAIF preparation (see FIG. 31).

All doses of MAIF resulted in an increase in the number of circulating neutrophils and a decrease in the number of lymphocytes. While the effect on lymphocytes was linearly related to dose, the increase in neutrophil numbers was in the form of a curve, the greatest effect being observed in those animals given 10 mg.

These results support the concept that the anti-inflammatory factor modulates inflammation by affecting the adhesion of neutrophils to endothelial cells.

Data were also obtained pertaining to the effect of three other cell-targeted, anti-inflammatory/immunomodulatory agents on circulating leucocytes in the rat. The steroidal drug, methylprednisolone, causes a change in the lymphocyte/ neutrophil ratio analogous to that seen with MAIF. The temporal relationship between drug administration and effect is somewhat different. The anti-rejection/anti-inflammatory agent cyclosporin A also causes an increase in the number of circulating neutrophils but lymphocyte numbers are either increased or not affected depending on the dose. In contrast, the cytotoxic drug cyclophosphamide depletes both circulating lymphocytes and neutrophils. The effects of the anti-inflammatory factor would appear to closely parallel the action of methyl-prednisolone.

EXAMPLE 18

Effect of the Anti-inflammatory Factor on Lymphocyte Function

The ability of the anti-inflammatory factor to induce a reversible decrease in the number of circulating lymphocytes (Example 17) prompted further investigation of the effect of the factor on lymphocyte function. Graft versus Host (GvH) and Host versus Graft (HvG) analyses were used to determine the effect of the factor on T lymphocyte function.

In the HvG analysis, parental Dark Agouti rats ("DA") were injected i.v. with 20 mg of the MAIF preparation 48, 24 and 3 hours before lymphocytes from their F1 hybrid offspring (DA×Hooded Oxford rats) were injected into their footpads. Thus, the effect of the anti-inflammatory factor on the ability of T lymphocytes from an intact host (DA) to respond to the foreign histocompatibility antigens of the F1 lymphocytes was measured. The protocol produced a highly significant reduction (30%) in the response as evidenced by a decrease in popliteal lymph node weight (FIG. 33A).

In the GvH reaction parental (DA) lymphocytes were obtained from MAIF treated parental rats (DA) and injected into the footpads of their F1 (DA×Hooded Oxford) offspring. This assay measured the in vivo responsiveness of T lymphocytes removed from the host under evaluation, i.e. from MAIF treated rats. The MAIF regimen had no effect on the GvH response (FIG. 33B).

During the preceding experiments, an apparent increase in the number of splenic lymphocytes in MAIF treated animals was noted. Further experiments showed a significant increase in both spleen weight and in spleen cell numbers (FIGS. 33C and 33D). The increase in spleen cell numbers was approximately equal to the decrease in the number of circulating cells reported previously.

Finally, the effect of the anti-inflammatory factor on the ability of isolated splenic lymphocytes to respond to the mitogen concanavalin A was determined. Administration of the MAIF preparation was found to almost totally abrogate the mitogenic response of cultured lymphocytes to this lectin (FIG. 33E).

EXAMPLE 19

Suppression of Infection Induced Inflammation by the Anti-inflammatory Factor

Experiments have been carried out to determine whether changes in serum levels of acute phase reactants (APRs) could be used to quantify the anti-inflammatory activity of the anti-inflammatory factor. The APRs are a group of proteins which are synthesized in response to an inflammatory stimulus. One of these, alpha 2 macroglobulin, is common to both man and rats and methodology for measuring this inflammatory component is available. Two intravenous injections of MAIF preparation (0 and 24 hours) did not reduce the peak response (48 hours) of alpha 2 macroglobulin. This result indicates that the factor does not affect the later inflammatory response.

EXAMPLE 20

In Vitro and in vivo Evaluation of Milk Derived Anti-Inflammatory Factor (Bovine Mammary Macrophage Assay, Infection Models in Mice)

Incubation of bovine mammary macrophages with the hyperimmune milk fraction did not detectably enhance the degree of phagocytosis but did increase the ability of macrophages to kill phagocytosed *Staphylococcus aureus*. Mice injected intraperitoneally with 10 mg of the MAIF preparation per kilogram demonstrated increased resistance to intraperitoneal challenge with lethal *Staphylococcus aureus*.

In an intra-mammary *Staphylococcus aureus mastitis* challenge model, MAIF injected mice also showed significantly less mammary inflammation and involution and increased clearance of the infectious organism. Quantitative histological analysis of mammary tissue from MAIF treated mice showed significantly more lumen, less interalveolar connective tissue, and less leukocytic infiltration compared to control mice. Mammary glands of treated mice also contained fewer colony forming units than control mice. The anti-inflammatory appears to exert its effect on the non-specific defense system by a modulation of leukocyte function.

EXAMPLE 21

Effect of the Anti-Inflammatory Factor on the Pathogenesis of Experimental Infection The most common inflammagens encountered by man are microbial and it is important to determine the effect of any agent which modulates host defenses against infection. The tissue damage which accompanies many infectious diseases is in fact caused by the host response to infection rather than by the invading organism. While the ability to modulate the inflammatory response to infection could be a useful clinical technique, it must be recognized that inhibition of the host response during infection can be disadvantageous. This is especially true in the case of neutrophil inhibition. Studies with agents which curb the participation of neutrophils in the early stages of infection have demonstrated that, while inflammation and tissue damage may be initially suppressed, the increased bacterial load that occurs as a result of the reduced cellular response eventual leads to an exacerbation of tissue damage. Thus, it is essential to evaluate the potential of the milk anti-inflammatory factor to modulate infection in order to (1) determine if the agent can reduce infection-induced tissue damage and (2) to assess whether any observed suppression of the host response is accompanied by an increase in the severity of infection.

Figure 34:
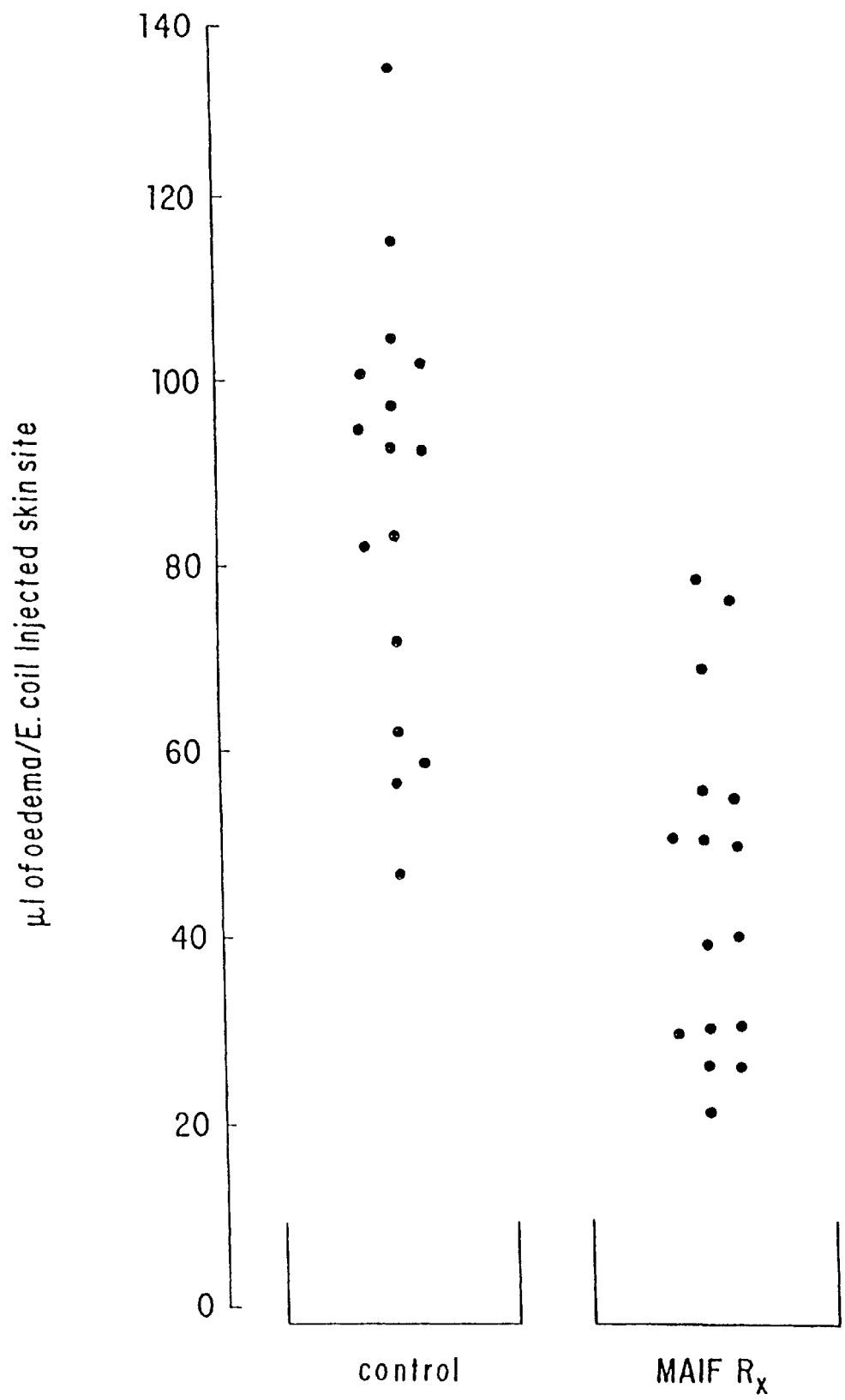
FIG. 34. Suppression of infection-induced edema by 40 mg of MAIF injected i.v. The mean values of the two groups were: controls, 87±22 µL; MAIF,45±17 µL;p<0.01.

The effect of the anti-inflammatory factor on edema formation following the intradermal injection of *E. coli* 075 was determined. Two groups of 8 animals were used. One group was untreated and served as controls while individuals in the second group were injected intravenously with 40 mg of the MAIF preparation in 0.5 ml saline. Immediately after the administration of MAIF, 100 μl of an overnight culture of *E. coli* 075 was injected intradermally at two skin sites on the shaved back of the rat, followed by the intradermal injection of 100 μl of saline at two further sites. To allow estimation of edema volume in the infected skin, 0.1 μCi of $^{125}$I-HSA was injected intravenously at the time of challenge. Six hours later the animals were anaesthetized, a blood sample obtained, the skin on the back removed and the infected and saline injected sites punched out. The volume of edema was calculated by relating tissue counts to plasma counts as described. To obtain the volume of edema which accumulates as a result of the presence of *E. coli* the edema/plasma volume of the saline-injected sites was subtracted. The results are shown in FIG. 34.

MAIF administration resulted in a 48% inhibition of edema formation. This experiment established that the anti-inflammatory factor could modulate the local inflammatory response to infection.

Figure 35:
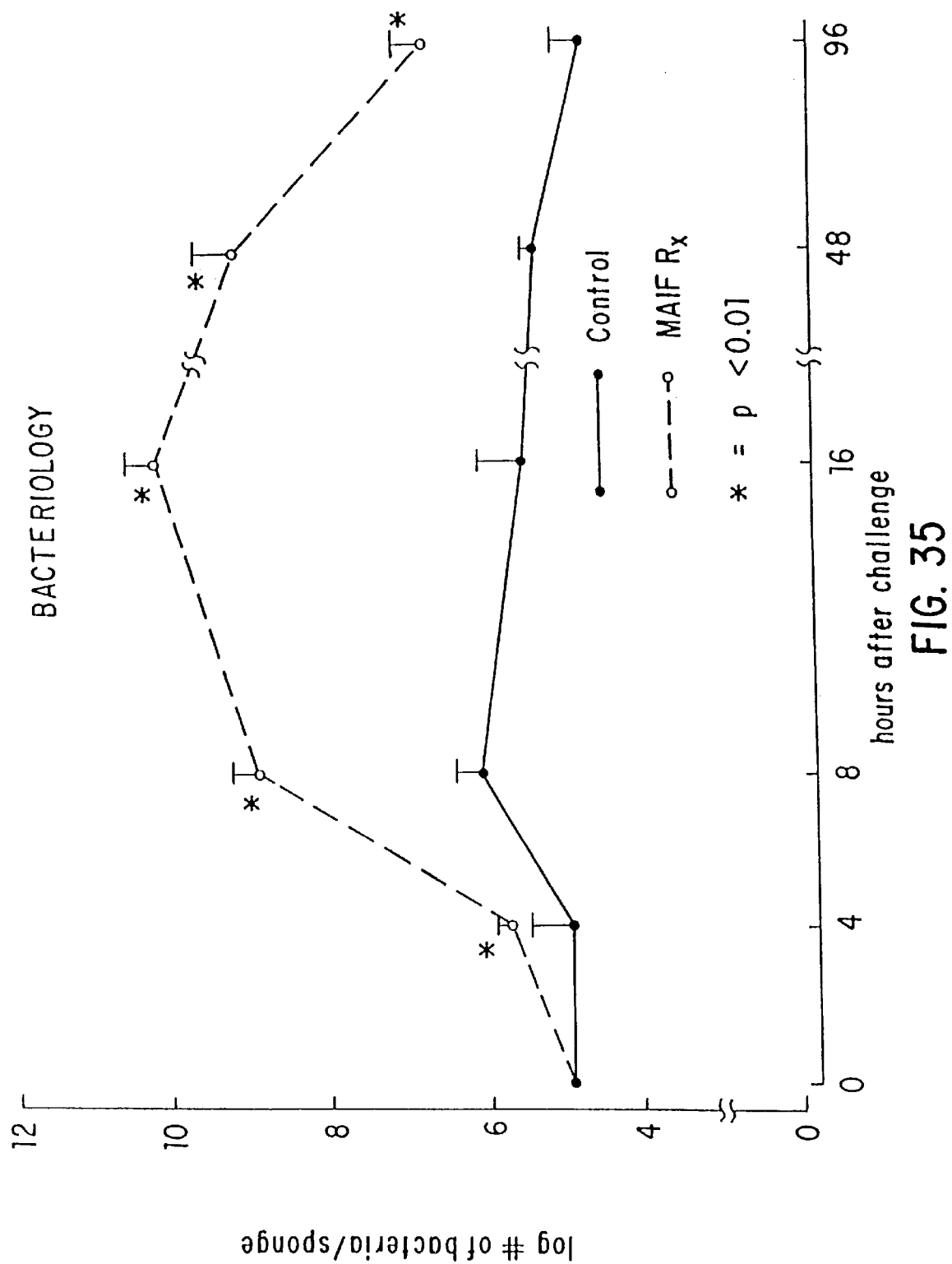
FIG. 35. Effect of MAIF given i.v. at 40 mg per rat on bacterial replication and subcutaneously implanted, $E.\ coli$-infected sponges.
Figure 37:
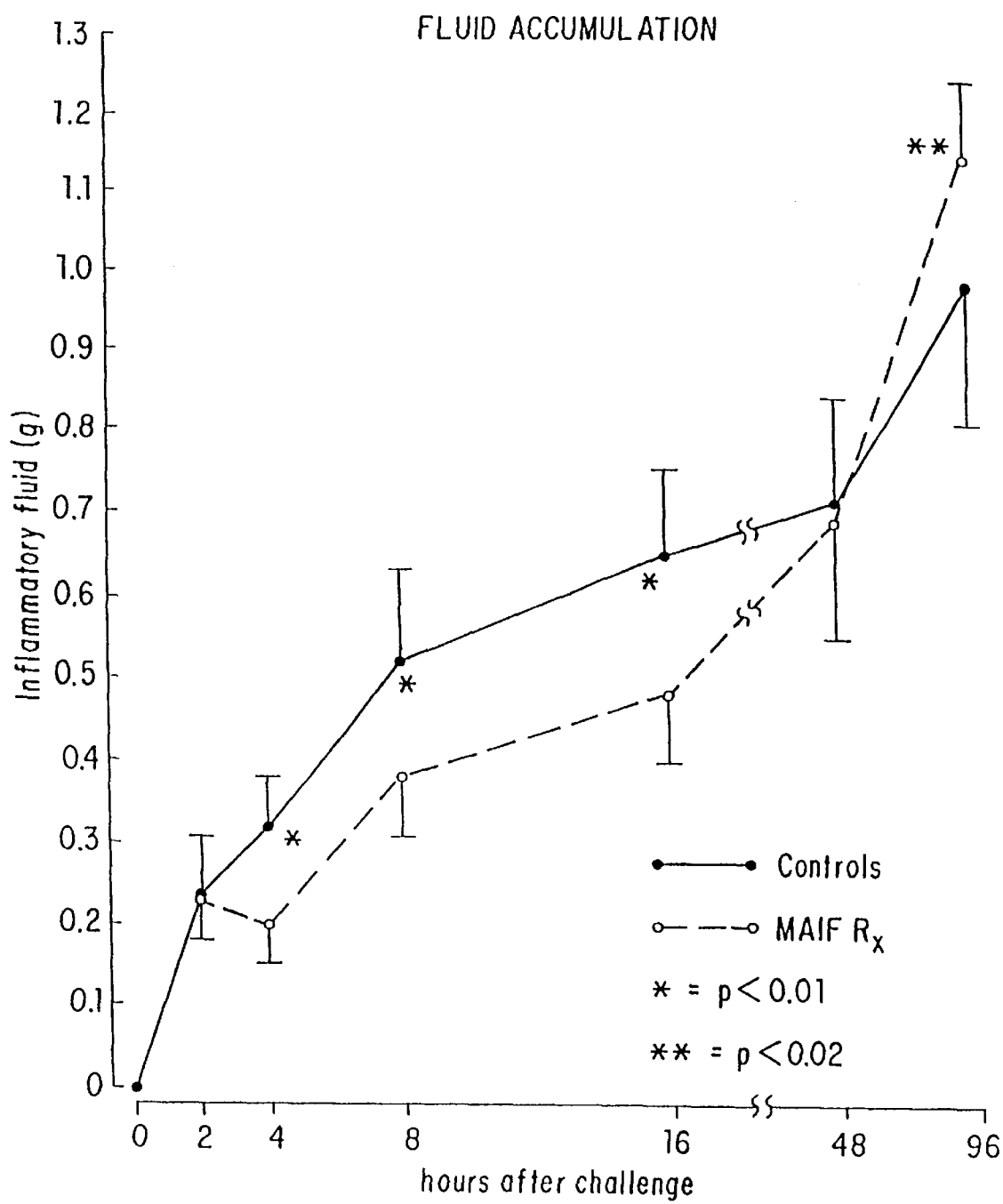
FIG. 37. Effect of MAIF (40 mg per rat, i.v.) on suppression of the intermediate phase (4–16 hours) of inflammatory fluid accumulation in $E.\ coli$-infected sponges.

In order to study the relationships between anti-inflammatory factor administration, bacterial replication, the accumulation of fluid and inflammatory cell infiltration, an alternative model of infection was employed. Polyurethane sponges, prepared and implanted as previously described, were infected with a quantitated sample of *E. coli* 075 at the time of implantation. The sponges were removed at timed intervals, weighed to determine the volume of the fluid exudate, and then squeezed in media to free the bacteria and cells from the sponge. Bacterial and cell numbers were estimated using techniques known to those skilled in the art. The following experiment was carried out using this model. Ninety animals were divided into two groups of 45. One of these groups was untreated and served as controls. The second group were injected intravenously with 40 mg of the MAIF preparation. The sponges were then implanted subcutaneously and, at the time of implantation, each sponge was inoculated with $10^5$ *E. coli* 075. Groups of 6–8 animals were killed at intervals thereafter and the bacteriological status and the size of the inflammatory infiltrate in the sponges determined. The results are illustrated in FIGS. 35–37.

The rate of bacterial replication was much greater in MAIF treated animals than in the controls and there was a 10, 1000 and 10,000 fold difference in bacterial numbers at 4, 8 and 16 hours respectively. Thereafter, bacterial numbers declined, although there was still a large difference at 96 hours (FIG. 35).

The early response to infection is the critical determinant in the outcome of an infectious episode. In this experiment the cellular infiltrate at 2, 4 and 8 h in those animals given MAIF was 27%, 35% and 46% of the control infiltrate respectively (FIG. 36B). The cells which accumulate in the first 24 h after challenge are >90% neutrophils and the suppression of this cellular component during this phase may account for the rapid increase in bacterial numbers. The accumulation of fluid at 2 hours was not affected by the administration of MAIF, but was significantly less 4, 8 and 16 hours following challenge. This is consistent with the previous finding that the anti-inflammatory factor did not suppress the primary, non-cellular phase of edema formation in the carrageenan footpad model. In previous studies, using the immunomodulatory agents cyclosporin A and methylprednisolone, a similar association between the suppression of the acute cellular inflammatory infiltrate and the promotion of bacterial replication was shown. However, in these experiments, the increased bacterial load promoted a host response between 24 and 48 hours post challenge in which there was a massive influx of neutrophils. When tissue was involved, the enhanced inflammatory response resulted in a marked exacerbation of tissue damage and scar formation. Interestingly, although administration of MAIF suppressed the early inflammatory response and was associated with a 10,000 fold increase in bacterial numbers there was no massive influx of neutrophils 24–48 hours post challenge.

EXAMPLE 22

Effect of the Anti-Inflammatory Factor on Experimental Pyelonephritis

An agent which can suppress inflammation in infection without resulting in a sequela of enhanced tissue damage would have considerable potential. A clinically relevant model of infectious disease could provide an experimental basis for establishing such potential.

Figure 38C:
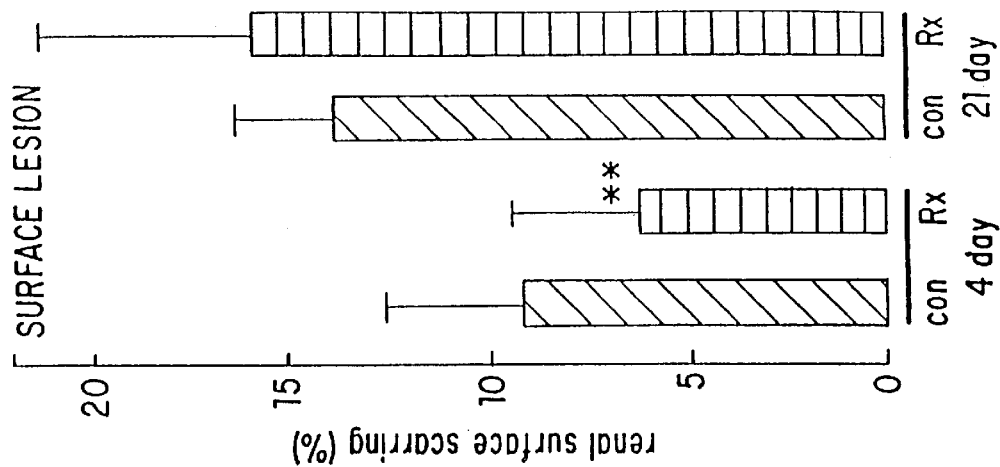
FIG. 38. Effect of 40 mg of MAIF, given intravenously at the time of challenge and 48 hours later, on the pathogenesis of experimental pyelonephritis. The dotted line on the left-hand graph represents the mean background kidney weight. *=p<0.01; **=p<0.02.
Figure 38B:
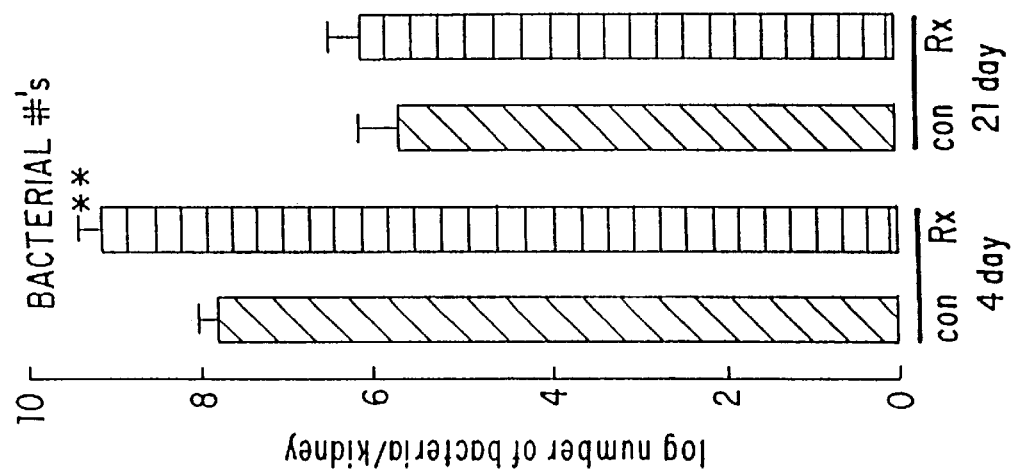
Figure 38A:
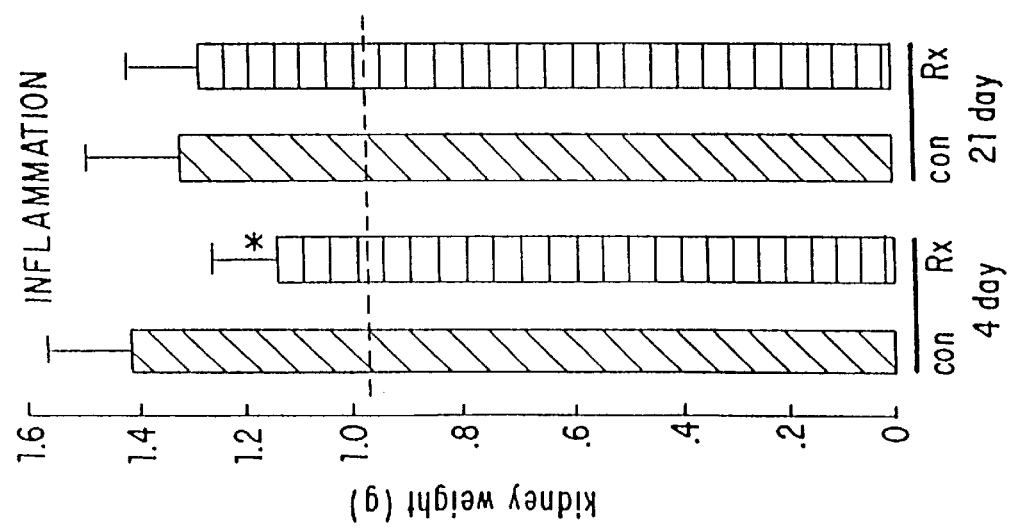

Pyelonephritis is an infectious disease which demonstrates local inflammation, tissue destruction and scar formation as cardinal histological features. A well characterized model of the disease is available, which reproduces the central pathological features of the disease in man. Pyelonephritis is induced in the rat by the direct inoculation of the surgically exposed kidney with a predetermined number of *E. coli* 075. Following challenge, bacterial numbers increase rapidly and reach a peak 3 to 4 days later. In normal animals the level of infection declines over the following 5 or 6 days and reaches a plateau at about 10 days post challenge. By 21 days the lesions have resolved and present as focal areas of indented scar tissue. To assess the effect of the anti-inflammatory factor on this model of infection, pyelonephritis was induced in both kidneys of twenty-six animals. One half of these animals were treated with the MAIF preparation intravenously at a dose of 40 mg/rat at the time of challenge and again 48 hours later. Seven animals from each group were killed 4 days after induction of pyelonephritis and the two remaining groups of six animals at 21 days. Kidneys were removed aseptically and weighed to determine the relative volume of the fluid exudate. The extent of the surface lesion size was estimated by direct visualization and the kidney homogenized to allow the enumeration of bacterial numbers. The results are shown in FIG. 38.

Four days after challenge the inflammatory response, as evidenced by the inhibition of fluid accumulation and the size of the lesions on the surface of the kidney, was suppressed by the administration of MAIF. As previously observed in the studies involving infected, subcutaneously-implanted sponges, the early suppression of inflammation resulted in a logarithmic increase in the number of bacteria in MAIF-treated animals. By 21 days there was no difference in the pathology of disease as measured by kidney weight, bacterial numbers or renal surface lesions size. Thus, while suppression of the early inflammatory response with MAIF did not result in a reduction in tissue destruction in the chronic (21 day) phase of pyelonephritis, neither did it promote the development of pathological lesions as other anti-inflammatory and immunomodulatory agents have done.

EXAMPLE 23

Summary of Experimental Data

A method was developed which allowed the accumulation of edema in the carrageenan injected footpad to be monitored continuously.

The early, non-phagocytic, phase of the inflammatory response was not affected by anti-inflammatory factor, whereas the later, cellular-driven, phase of the reaction was significantly inhibited. Further experiments, in which MAIF was administered at intervals before or after the injection of carrageenan, provided additional evidence that MAIF exerted its anti-inflammatory effect by modulating the secondary, neutrophil-mediated, inflammatory response.

The anti-inflammatory factor was shown to have a half-life of 1–2 hours following i.v. injection and development of inflammation could be suppressed when the factor was administered 30 minutes after challenge. This result is relevant to the potential therapeutic use of the anti-inflammatory factor.

The neutrophil is the principal cell involved in the acute inflammatory response. During the Arthus reaction, a >80% reduction in neutrophil accumulation was observed following MAIF administration which, in turn, was associated with a highly significant inhibition of the secondary characteristics of the inflammatory reaction, namely edema and hemorrhage. This result further implicated neutrophils as a target in MAIF-induced suppression of inflammation.

One of the key steps in the development of inflammation is the migration of neutrophils from the vasculature to the tissue. The intravenous administration of the anti-inflammatory factor was shown to result in profound and dose dependent inhibition of neutrophil migration. When the effect of the anti-inflammatory factor on peripheral blood leukocytes was investigated, a marked increase in the number of circulating neutrophils was observed, accompanied by a corresponding decrease in the number of lymphocytes. This effect was also dose-dependent, but in the case of the increase in neutrophil numbers, was not linear.

The administration of the milk anti-inflammatory factor was found to both block the adhesion of neutrophils to the endothelium and to promote the dissociation of hose neutrophils which were adherent at the time of administration. This effect is probably the result of the ability of the anti-inflammatory factor to block the interaction between cell surface CD18 antigens and other molecules. The inhibition of CD18 binding by the factor appears to be specific in that the factor prevented the binding of anti-CD18 monoclonal antibody to cells but did not similarly prevent the binding of anti-CD11b monoclonal antibody.

The blocking of intermolecular interactions involving the CD18 cell surface antigen may also account for the observation that the factor was able to inhibit the ability of host lymphocytes to respond to foreign histocompatibility antigens. In other experiments, the anti-inflammatory factor was found to block the concanavalin-induced mitogenic response in lymphocytes.

Finally, the factor significantly suppressed the early cellular response to infection, an effect which resulted in a logarithmic increase in bacterial numbers in a model of subcutaneous infection. This exacerbation of infection did not result in a rebound of the inflammatory response, as seen with other agents which suppress acute inflammation in infection. A second experiment using a clinically relevant model of infection, pyelonephritis, also demonstrated a suppressive effect on inflammation which was associated with an increase in bacterial numbers. Again no rebound effect was observed and there was no difference in the degree of tissue damage which occurred in the MAIF treated and control groups.

The following conclusions can be drawn from this series of experiments:

1. Anti-inflammatory factor, administered i.v., suppresses the secondary, neutrophil-mediated, phase of the carrageenan induced inflammatory response.
2. When evaluated in the carrageenan footpad assay the anti-inflammatory factor has a biological half-life of 1–2 hours and is effective even when administered after inflammation is induced. Subsequent experiments indicate that the effective half-life is dependent on both the dose and inflammatory stimulus employed.
3. Anti-inflammatory factor inhibits neutrophil emigration in vivo.
4. Anti-inflammatory factor administration results in an increase in the number of circulating neutrophils and a corresponding decrease in lymphocyte numbers.
5. Anti-inflammatory factor suppresses host defenses against infection, probably via an effect on neutrophil emigration.
6. Anti-inflammatory factor blocks interactions between cell surface CD18 antigens and other molecules.
7. Anti-inflammatory factor blocks the adhesion of neutrophils to the endothelium.
8. Anti-inflammatory factor promotes the dissociation of adherent neutrophils from the endothelium.
9. Anti-inflammatory factor blocks the ability of host lymphocytes to respond to foreign histocompatibility antigens.
10. Anti-inflammatory factor blocks the mitogenic response of lymphocytes.

The experimental data obtained in these studies demonstrate clearly that milk anti-inflammatory factor has a marked effect on both neutrophils and lymphocytes. The effects observed may be the result of a direct effect of anti-inflammatory factor on cells per se, or the result of the suppression (or stimulation) of some other cellular or soluble mediator which indirectly alters the biological activities of cells. It is also widely accepted that most pharmacological agents have multiple actions and it is possible that the anti-inflammatory factor will be found to affect a number of other, as yet unidentified, biological processes.

EXAMPLE 24

Method of Obtaining Highly Purified MAIF

The isolation of a bioactive factor in a highly purified form suitable for compositional and structural analysis requires the availability of a large source of starting material, the development of large-scale production and processing capabilities and the establishment of the necessary biological and biochemical assays required to confirm biological activity at every step of the purification procedure. Methods for preparation of MAIF from skimmed milk similar to those described earlier in this application were used to produce a MAIF preparation with a degree of purity suitable for preliminary analytical studies. A preferred method for the preparation of MAIF in large quantities suitable for handling, transportation, storage and processing is disclosed below. The following procedures will permit the production of a highly purified form of MAIF in quantities sufficient for composition and structural studies to be performed.

Materials

Chemicals were all reagent grade. Water used for large-scale preparative procedures was sterile water for injection or was freshly prepared pyrogen-free deionized water. Spray-dried rennet whey produced from hyperimmune milk was used for the production of large-scale amounts of MAIF.

Standardized MAIF Preparation

In order to compare the MAIF activities in different batches of milk from hyperimmune cows or from control cows, a standardized procedure involving ultrafiltration and ion exchange chromatography was adopted to prepare a partially purified, highly active sample. A convenient volume (3 to 100 liters) of fresh, cold skimmed milk was subjected to ultrafiltration through the Minisete unit (Omega membrane) at 30 psi until the volume of filtrate collected was equal to ⅔ of the starting volume of milk. A convenient volume of standardized, <10,000 daltons (<10K daltons) permeate (250 ml, 500 ml, etc.) was applied to a DEAE column that was 26.7% of the permeate volume. The column was washed with a volume of deionized water 2 times that of the permeate and eluted with a volume of 0.15 M NaCL equal to 58.3% of the permeate volume. The MAIF activity in standardized DEAE preparations was determined in the neutrophil migration inhibition assay (see below) and was defined as the percent inhibition of neutrophil migration induced by a 3 mg/120–150 gm rat dose.

Neutrophil migration inhibition activities of samples resulting from further purification of MAIF were compared to the activities of standardized DEAE MAIF preparations. All samples were also evaluated for their pro-inflammatory potential in a tumor necrosis factor induction assay (see below).

Highly Purified MAIF Preparation

Ultrafiltration. Ninety liters of fresh, cold (4° C.), non-pasteurized skimmed milk from hyperimmunized cows was pumped through a 25° C. in-line warming bath and then passed through a Minisette (Filtron) ultrafiltration cassette containing an Omega (model #OS010C01) membrane with a molecular weight cut-off of <10K daltons. Inlet pressure was maintained at 30 psi. The resulting permeate (<10K permeate) was collected on ice until a volume of sixty liters was accumulated. The <10K permeate was used immediately for further purification by ion exchange chromatography or was frozen and stored at −20° C. or was lyophilized.

For large-scale production of MAIF, 18 kg of whey powder from hyperimmune milk was dissolved in 300 liters of cold (4° C.) pyrogen-free, water. The cold whey was passed through a process filter and was then pumped through a 400 ft$^2$ spiral-wound 1000 MW cut-off ultrafiltration membrane (DESAL model GE2540F) at a pressure of 300 psi until the retentate became ⅓ of the starting volume. During ultrafiltration the retentate was chilled by recirculation through a 10° C. in-line heat exchanger. The <1K filtrate was collected at 4° C. in sterile containers and was frozen at −20° C. and lyophilized.

Ion Exchange Chromatography. Sixty liters of cold fresh <10K permeate was applied directly to a 37 cm×15 cm column (Pharmacia, Model KS 370/15) containing 16 liters of diethyl-aminoethyl (DEAE)-Sepharose Fast Flow ion exchange resin (Pharmacia #17-0709-05) at a flow rate of 4.8 liters/hr. using a low pressure peristaltic pump. The column effluent was monitored at 280 and 254 nm with a Pharmacia Dual Path UV monitor (Model 19-24217-01). The loaded column was washed with 120 liters of sterile deionized water to elute unbound material until the 280 nm absorbance of the effluent returned to baseline. Bound components were eluted with 35 liters of 0.15 M NaCl. The column eluate was lyophilized and stored in amber glass vials in the dark. MAIF activity in column eluates was determined in the neutrophil migration inhibition assay (see below).

Size Exclusion Chromatography. Partially purified DEAE preparations of MAIF were separated on a preparative TSK G2500PW (21.5×600 mm) size exclusion HPLC chromatography column (TosoHaas, Montgomeryville, Pa.) equilibrated with 0.15 M NH$_4$OAc on a Hewlett-Packard Model 1090 HPLC with an automatic injector and a diode array detector. Lyophilized DEAE-MAIF (100 mg) was dissolved in 0.25 ml of 0.15 M NH$_4$OAc and injected onto the column. The column was eluted with 0.15 M NH$_4$OAc at a flow-rate of 5 ml/min. The effluent was monitored at 220 and 280 nm, however, diode array data was stored for all wavelengths between 190 and 600 nm. Fractions (9 ml) were collected on an LKB ULTRARAC fraction collector. To prepare large quantities of MAIF, multiple samples of 100 mg each were separated on the TSK column and collected into the same set of tubes. Tubes containing the active factor were pooled, lyophilized and weighed.

Organic Partition Extraction. MAIF was selectively isolated from bound salts by an organic partition extraction method in which the semipurified TSK-MAIF sample was dissolved in distilled water, alkalized, extracted with n-hexane to remove neutral lipids, acidified and then extracted with ethyl acetate. 50 to 100 mg of TSK-MAIF was dissolved in 2 ml deionized water in a tared extraction vessel. The pH of the solution was adjusted to 8.0 with 4 drops of 0.02 N NH$_4$OH. Two milliliters of n-hexane were added and the mixture was shaken vigorously. The upper phase consisting of hexane was removed, dried and weighted. The remaining aqueous solution was acidified to pH 3.5 with 100 drops of citric acid. Five milliliters of ethyl acetate was added and the mixture was shaken vigorously and centrifuged at 1000 rpm to separate layers. The ethyl acetate layer was transferred to a tared vessel. The extraction was repeated with a second 5 ml volume of ethyl acetate. The ethyl acetate layers were combined, dried under nitrogen and weighed.

Reversed-Phase HPLC. A Zorbax SB-C$_{18}$ reversed phase HPLC column (Mac-Mod) was used to separate the weakly ionic negatively charged MAIF components freed of bound salts by the ethyl acetate extraction procedure. Separations were achieved with an ion-pairing isocratic mobile phase consisting of 35% methanol, 20 mM octylsulfonate, and 0.025% trifluoroacetic acid (TFA). Samples of up to 50 mg of extracted material were dissolved in 35% methanol, 0.025% TFA and applied to the column. The column was developed at a flow-rate of 1 ml/min. The column eluate was monitored at 214 and 280 nm. Selected fractions were tested for MAIF activity in the neutrophil migration inhibition assay (see below).

Neutrophil Migration Inhibition Assay. MAIF anti-inflammatory activity was determined in a pleural neutrophil migration inhibition assay. Female, white laboratory rats weighing 120 to 150 g were injected intrapleurally with 1.0 ml of 1% kappa carrageenin in PBS to induce neutrophil migration into the pleural cavity. Immediately, the rats were injected intraperitoneally with 0.5 ml doses of MAIF samples in PBS. PBS was used as a control. After four hours, the rats were sacrificed, pleural exudates were collected, and the emigrated neutrophils were counted.

Tumor Necrosis Factor Assay. The capacity of MAIF samples to induce pro-inflammatory cytokines as an indicator of endotoxin contamination was evaluated in a tumor necrosis factor induction assay. Test samples are diluted in RPMI medium and incubated with J774 mouse macrophage cells in a 24-well plate at 37° C. for four hours. The quantity of TNF released from the macrophage cells as a result of incubation with test samples is quantitated by specific TNF ELISA assay. Aliquots of cell supernatants are incubated in anti-TNF monoclonal antibody coated plates overnight at room temperature. Bound TNF is detected in the wells with a biotinylated second antibody developed with a streptavidin peroxidase—TMB substrate system. Developed color is quantitated at 450 mn and compared to a standard curve of TNF.

RESULTS

Standardization of Preparative Methods

Figure 39:
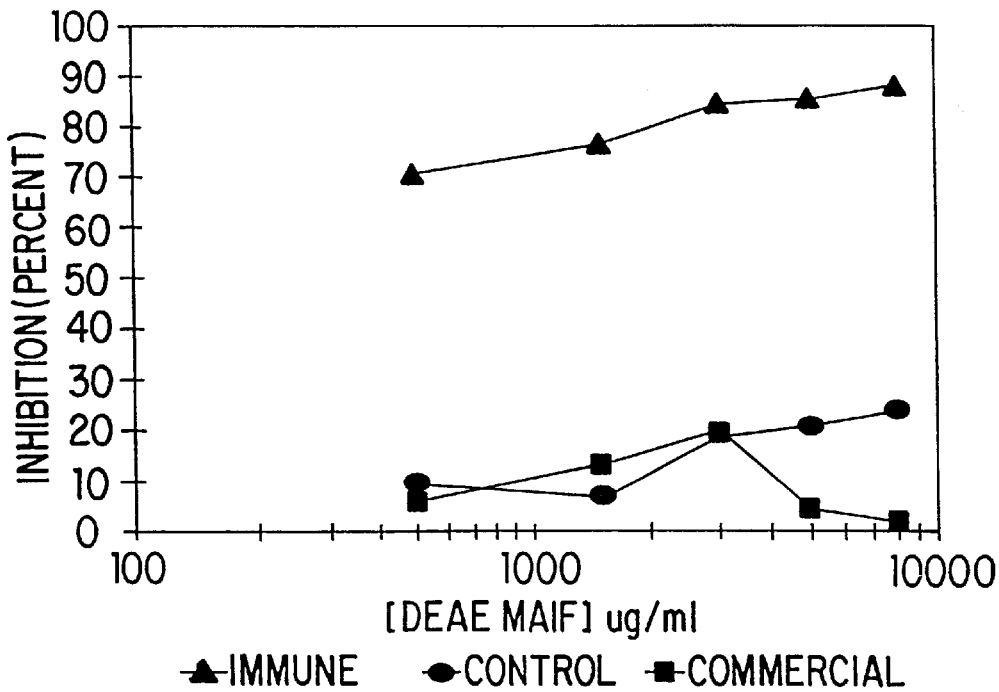
FIG. 39. Comparison of standardized hyperimmune and control MAIF. MAIF prepared by standardized methods was tested at doses of 0.5, 1.5, 3, 5 and 8 mg/120–150 gm. female rat for their ability to inhibit the migration of neutrophils to inflammatory sites. Reference to "commercial" is to off the shelf powdered skim milk.
Figure 40:
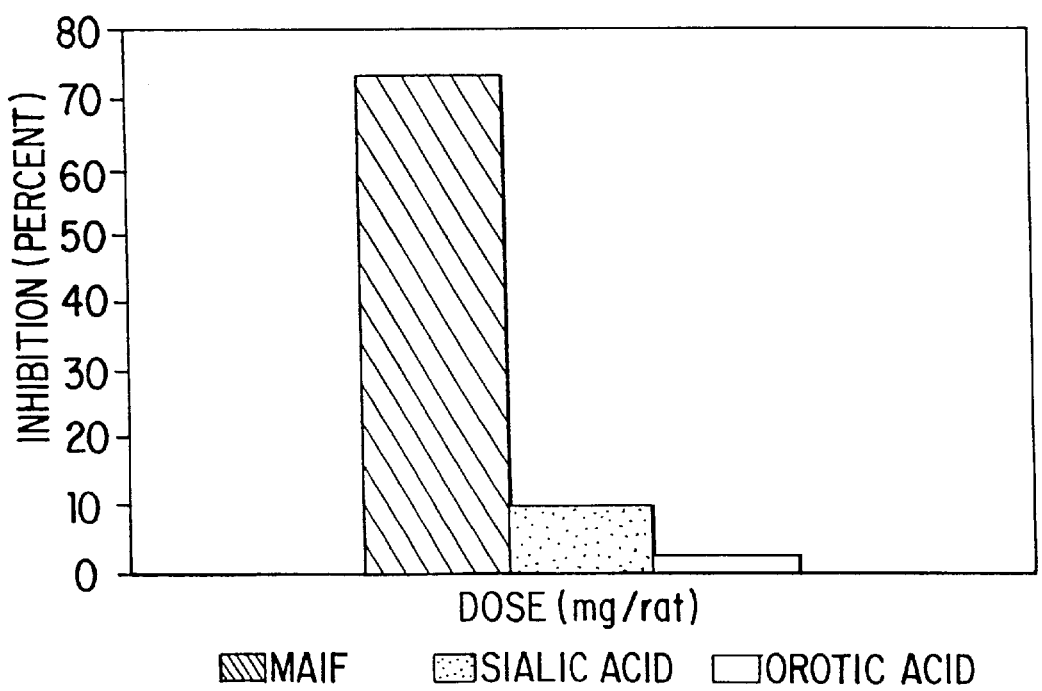
FIG. 40. Comparison of MAIF and other milk components. The activity of standardized MAIF prepared from hyperimmune milk was compared with sialic acid and orotic acid, known components of milk believed to have anti-inflammatory activity.

Reproducible methods involving ultrafiltration and DEAE column procedures and analysis of comparable samples in the rat neutrophil migration inhibition assay were established for the production of highly active MAIF preparations. The adoption of standardized purification methods permitted quantitation of MAIF activity in specific milk products and in large-scale production batches. To evaluate the standardized method, MAIF was prepared from hyperimmune milk, from control milk obtained from non-immunized cows and from a commercial powdered milk and was tested blind in the neutrophil migration inhibition assay. MAIF samples were tested at doses of 0.5, 1.5, 3, 5, and 8 mg/120–150 gm rats for their ability to inhibit the migration of neutrophils to inflammatory sites (FIG. 39). MAIF from hyperimmune milk produced a maximum neutrophil inhibition of more than 70% at the 3 mg dose. Fresh control milk and commercial control milk each produced only 18% inhibition at the 3 mg dose. The activity of standardized MAIF prepared from hyperimmune milk was compared with sialic acid and orotic acid, known components of milk believed to have anti-inflammatory activity (FIG. 40). Neither the sialic acid nor the orotic acid exhibited any inhibitory activity on the migration of rat neutrophils in the doses tested.

MAIF Purification by Preparative HPLC

Figure 41:
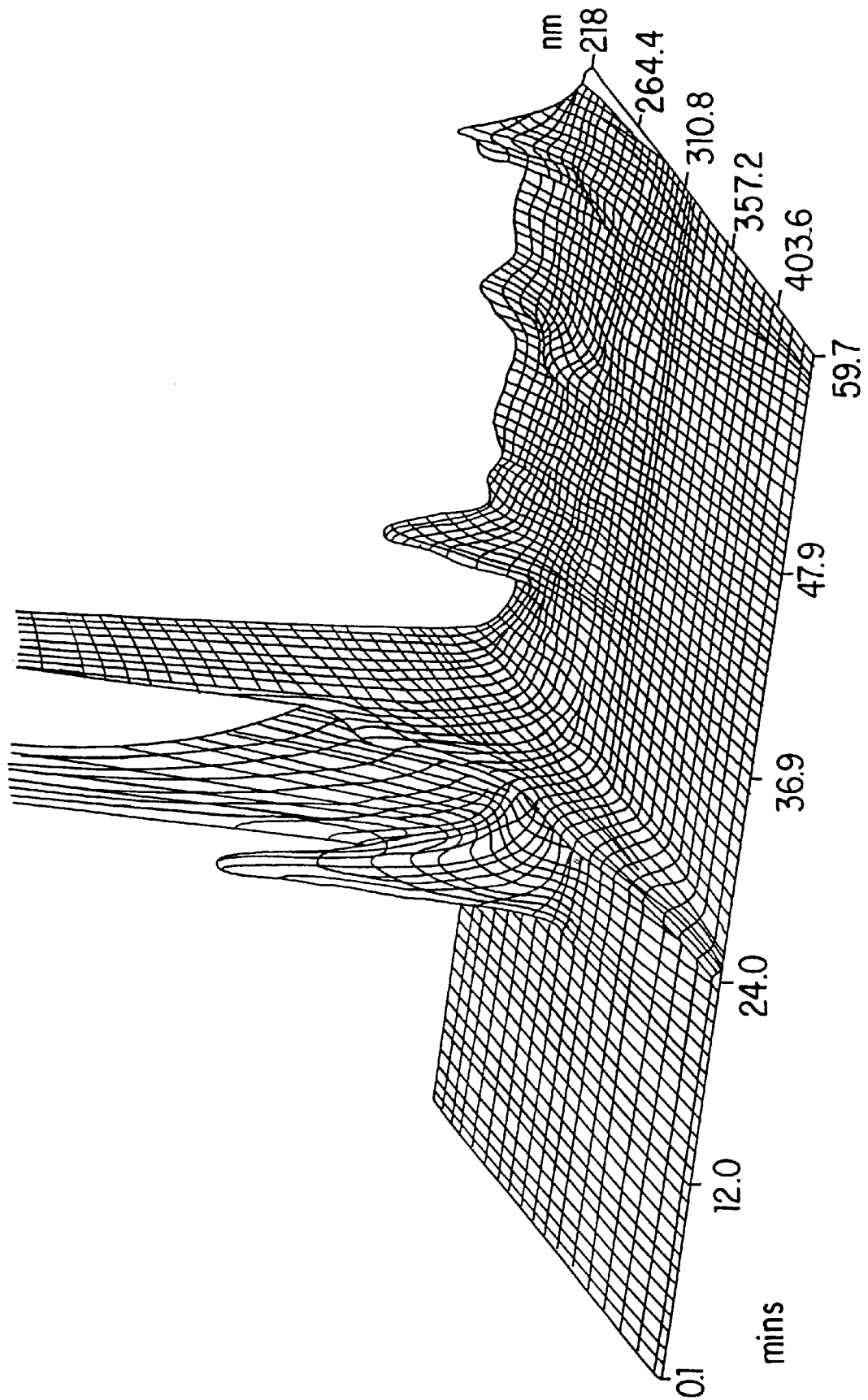
FIG. 41. Analysis of the composition of the DEAE-derived MAIF by size exclusion HPLC.

The use of DEAE ion exchange chromatography to prepare MAIF resulted in a 25-fold purification of the anti-inflammatory activity with respect to the <10K permeate. Analysis of the composition of the DEAE-derived MAIF by size exclusion HPLC (FIG. 41) indicated the presence of two major components at 17 and 25 minutes and six or more minor components which eluded between 30 and 60 minutes. Analysis of pooled fractions in the neutrophil migration inhibition assay demonstrated that the major concentration of MAIF activity occurred in the 25 minute peak. These results indicated that a preparative size separation step would permit the preparation of a more highly purified preparation of MAIF. Attempts to achieve comparable results on a preparative liquid chromatography medium did not provide adequate separations. A preparative HPLC TSK2500PW column, eluted with 0.15 M $NH_4OAc$, provided excellent separation of the 25 minute MAIF peak. DEAE-MAIF was separated on the HPLC column in 100 mg runs and the pooled 25 minute peak was lyophilized. The 0.15 M $NH_4OAc$ elution buffer was selected because all buffer salts would be completely removable from isolated MAIF samples during lyophilization. However, when repeated 100 mg runs of DEAE-MAIF were fractionated by preparative HPLC, recovered weights of the 25 minute peak exhibited only a 10% reduction in weight. Elemental analysis of the MAIF peak indicated that more than 40% of the weight could be attributed to salt. Several salts, including sodium chloride, sodium acetate and magnesium chloride, were tested to determine their elution position on the TSK 2500PW column. Each salt eluted between 35 and 40 minutes. This result indicated that salts were specifically bound by the MAIF compound eluting at 25 minutes.

Elimination of Contaminating Salt

In order to free the MAIF compound from bound salts, an organic partition extraction method was used in which the HPLC purified MAIF preparation was alkalized to expose negatively charged groups and extracted with hexane to remove hexane soluble contaminants. The aqueous phase was then acidified to protonate negative charges, extracted into ethyl acetate and weighed. The extracted residue exhibited a reduction in weight of more than 96%. Analysis of the dried ethyl acetate fraction in the neutrophil migration inhibition assay demonstrated strong MAIF activity and required as much as a 10,000 fold reduced dose of the highly purified MAIF to obtain the same level of neutrophil migration inhibition as MAIF obtained prior to the organic partition extraction (FIG. 42).

Production of MAIF by <1K Ultrafiltration

Figure 43:
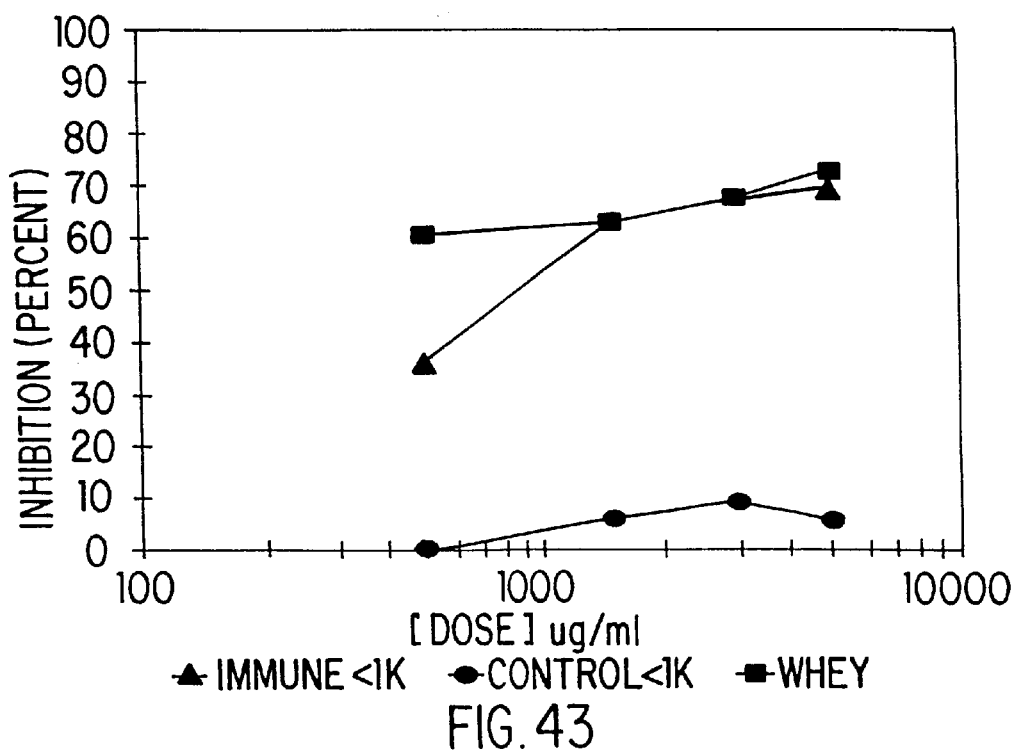
FIG. 43. Analysis of hyperimmune whey and preparations of <1,000 dalton filtrate from hyperimmune whey in the neutrophil migration inhibition assay in comparison to <1,000 dalton filtrate prepared identically from control whey.
Figure 44:
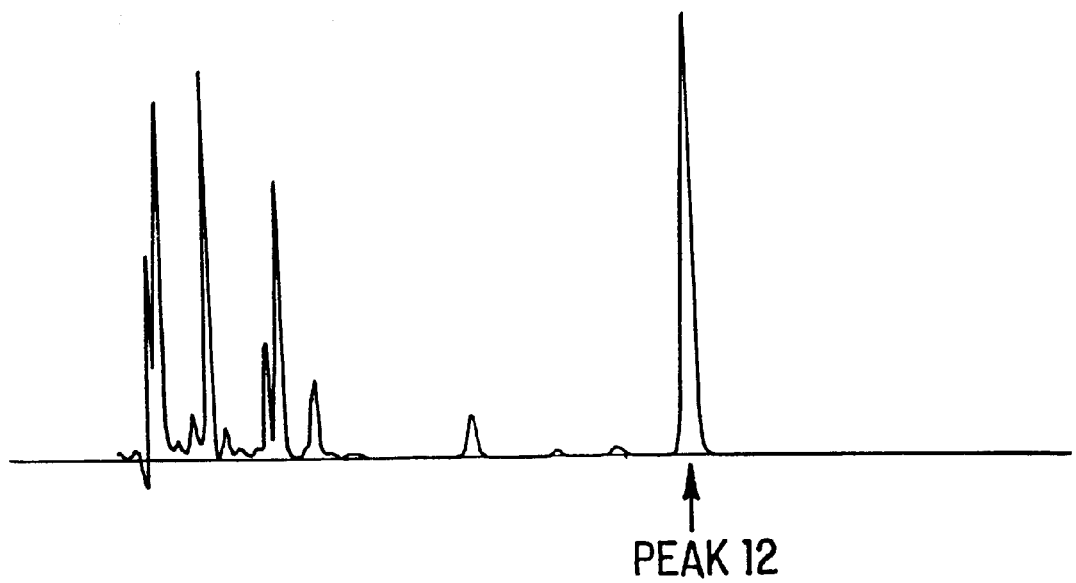
FIG. 44. Analysis of organic extracts of the <1,000 dalton filtrate on reversed-phase HPLC exhibiting a prominent peak at approximately 12 minutes (Peak 12) as well as several other components.

A large-scale isolation and purification procedure for the production of quantities of MAIF sufficient for biochemical characterization, compositional analysis and structural characterization has been developed using powdered hyperimmune whey as the starting material. Whey is subjected to ultrafiltration on a 1000 MW cut-off ultrafiltration membrane. The collected filtrate can be lyophilized or concentrated by reverse osmosis and spray dried. Hyperimmune whey and preparations of <1K filtrate from hyperimmune whey routinely inhibited neutrophil migration, while <1K filtrate prepared identically from control whey had low inhibitory activity (FIG. 43). Since endotoxin, certain salts, and a large portion of the whey lactose are rejected by the UF1000 membrane, <1K filtrates contain relatively low salt and lactose and are TNF negative. Organic extracts of the <1K filtrate had activity in the neutrophil migration assay. Analysis of extracts of <1K filtrates on reversed-phase HPLC exhibited a prominent peak at approximately 12 minutes (Peak 12) as well as several other components (FIG. 44). Reversed-phase analysis of the organic extracts of hyperimmune whey revealed the presence of an identical peak at 12 minutes. Preparations from control milk contained small or undetectable amounts of Peak 12. These results indicate that partition extraction of the <1K filtrate resulted in the removal of significant amounts of salt and other contaminants and permits the preparation of a more highly purified preparation of MAIF than previously obtainable.

MAIF Purification by Reversed-Phase HPLC

Figure 45:
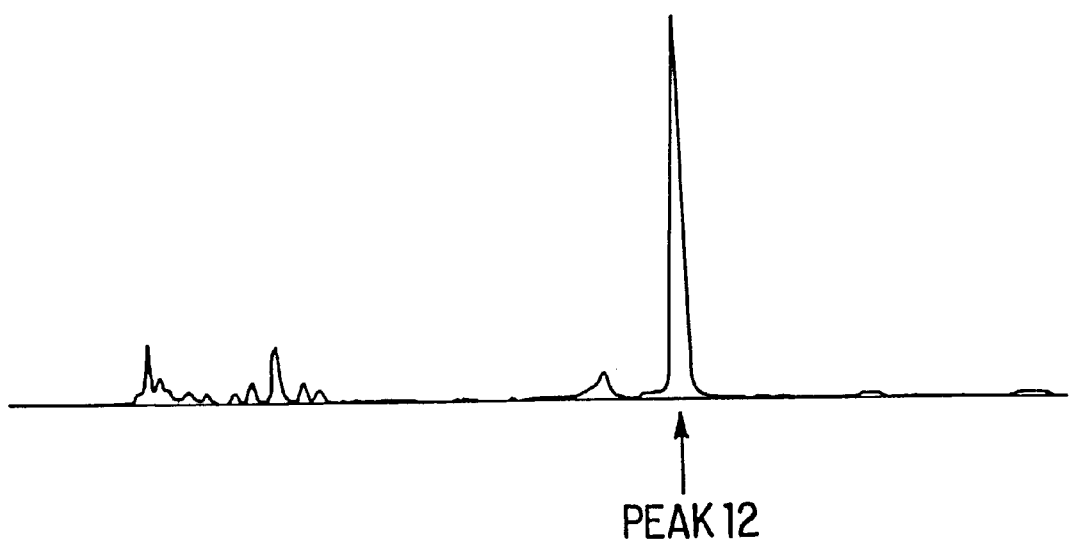
FIG. 45. Analysis of fractions containing Peak 12 from reversed-phase HPLC that have been pooled, lyophilized and rechromatographed on reversed-phase HPLC in a mobile phase containing only methanol and water.
Figure 46:
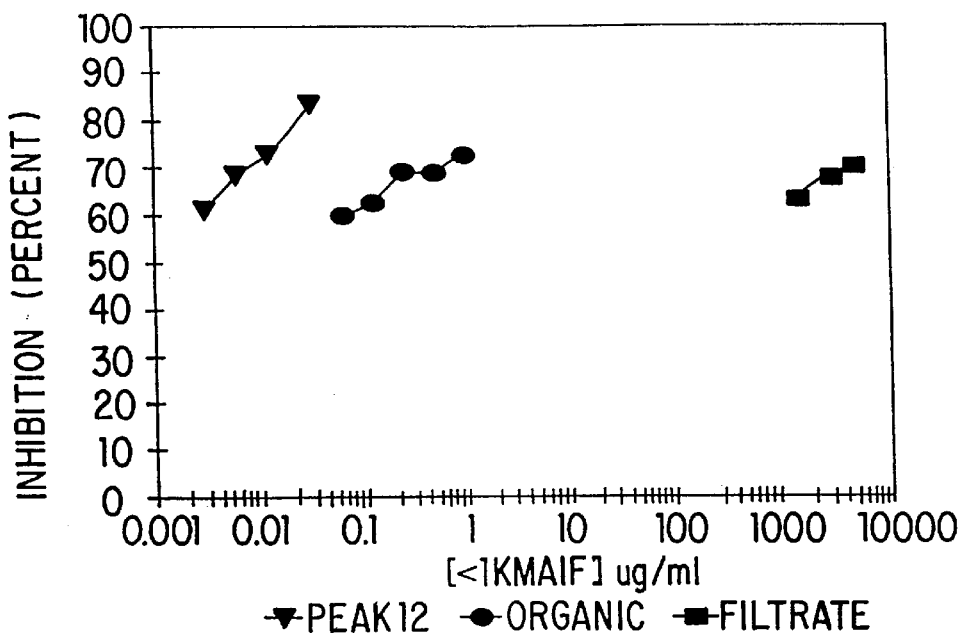
FIG. 46. Analysis of rechromatographed fractions containing Peak 12 in the neutrophil migration inhibition assay. Peak 12 showed 60% to 80% inhibitory activity at doses of 3 to 30 nanograms.
Figure 47:
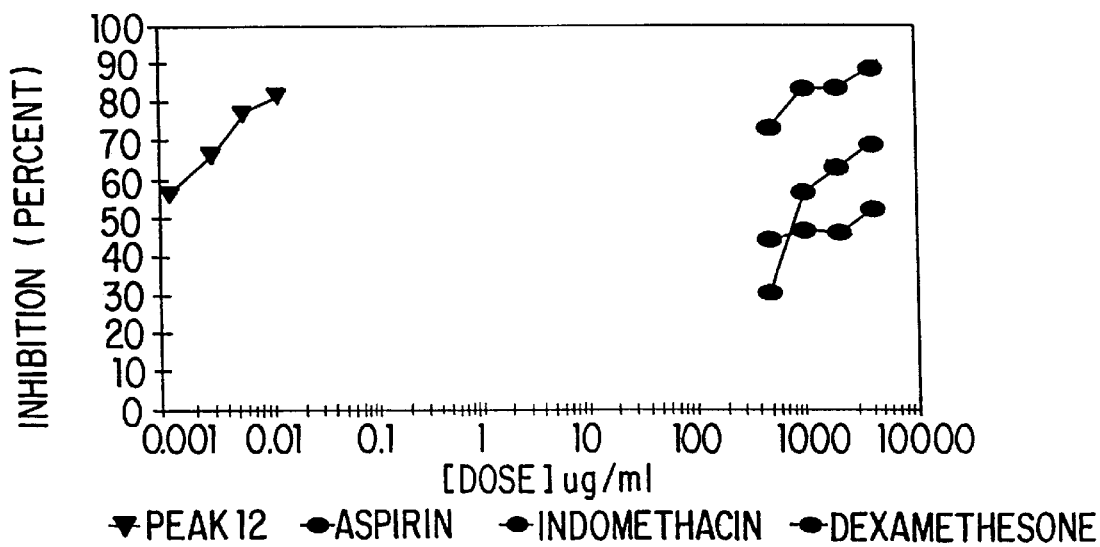
FIG. 47. Analysis of rechromatographed fractions containing Peak 12 in the neutrophil migration inhibition assay in comparison with aspirin, indomethacin and dexamethasone.

Peak 12 was isolated in preparative quantities by collecting fractions from repeated separations of organic extracts of <1K filtrate on reversed-phase HPLC. Fractions containing Peak 12 were pooled, lyophilized and rechromatographed on reversed-phase HPLC in a mobile phase containing only methanol and water (FIG. 45). Fractions containing Peak 12 were collected and dried. When tested in the neutrophil migration assay, Peak 12 showed 60% to 80% inhibitory activity at doses of 3 to 30 nanograms (FIG. 46). When compared together in the neutrophil assay with aspirin, indomethacin and dexamethasone (FIG. 47), Peak 12 exhibited 100,000 times the activity of the three anti-inflammatory drugs all of which were active in the high microgram to milligram range.

These results indicate that a highly purified form of MAIF can be produced by preparative reversed-phase HPLC of a direct organic extraction of a <1K filtrate obtained from hyperimmune whey. MAIF produced by this method exhibits high activity when compared to MAIF from control milk or to postulated or known anti-inflammatory drugs. MAIF produced by this method is more purified and more highly active than preparations obtained by previous methods. The use of this novel procedure will provide sufficient quantities of highly purified material necessary for the compositional and molecular structural studies of MAIF.

All references cited herein are fully incorporated by reference into this disclosure.

Having now generally described this invention, it will become readily apparent to those skilled in the art that many changes and modifications can be made thereto without affecting the spirit or scope thereof. Such changes and modifications are also considered aspects of the invention.

What is claimed is:

1. A method for purifying an anti-inflammatory factor from skimmed milk comprising:
   (i) ultrafiltering said skimmed milk through a filter with a molecular weight cut-off of 1,000 daltons;
   (ii) collecting the <1,000 dalton permeate from step (i);
   (iii) extracting the permeate from step (ii) by organic partition extraction and obtaining the organic extract from said extraction;
   (iv) separating the organic extract from step (iii) by reversed-phase HPLC chromatography; and
   (v) collecting the eluate.

2. The method of claim 1 wherein said skimmed milk is hyperimmune skimmed milk.

3. The method of claim 2 wherein said hyperimmune skimmed milk is whey.

4. The method of claim 1, wherein said organic partition extraction comprises:
   (i) extracting with hexane and $NH_4OH$;
   (ii) reextracting the aqueous phase from step (i) with ethyl acetate; and
   (iii) collecting said ethyl acetate extract.

5. The method of claim 4, wherein said reversed-phase HPLC chromatography column is a Zorbax SB-$C_{18}$ column.

6. An anti-inflammatory factor in highly purified form produced by a process comprising:
   (i) ultrafiltering skimmed milk through a filter with a molecular weight cut-off of 1,000 daltons;
   (ii) collecting the <1,000 dalton permeate from step (i);
   (iii) extracting the permeate from step (ii) by organic partition extraction and obtaining the organic extract from said extraction;
   (iv) separating the organic extract from step (iii) by reversed-phase HPLC chromatography; and
   (v) collecting the eluate.

7. The anti-inflammatory factor of claim 6 wherein said skimmed milk is hyperimmune skimmed milk.

8. The anti-inflammatory factor of claim 7 wherein said hyperimmune skimmed milk is whey.

9. The anti-inflammatory factor of claim 1 wherein said organic partition extraction further comprises:
   (i) extracting with hexane and $NH_4OH$;
   (ii) reextracting the aqueous phase from step (i) with ethyl acetate; and
   (iii) collecting said ethyl acetate extract.

10. An anti-inflammatory factor in substantially or highly purified form produced by the method of claim 1.

11. A method for inhibiting neutrophil migration comprising administering to an animal the milk anti-inflammatory factor obtained by the method of claim 1 at a dose sufficient to inhibit said neutrophil migration.

12. A method for inhibiting the inflammatory response comprising administering to an animal the milk anti-inflammatory factor obtained by the method of claim 1 at a dose sufficient to inhibit said inflammatory response.

13. A method for inhibiting neutrophils from adhering to endothelial cells in a mammal, wherein said method comprises administering to said mammal the milk anti-inflammatory factor obtained by the method of claim 1 at a dose sufficient to inhibit said adherence.

14. A method for detaching neutrophils which have adhered to endothelial cells in a mammal, wherein said method comprises administering to said mammal the milk anti-inflammatory factor obtained by the method of claim 1 at a dose sufficient to cause said detachment.

15. The method of claim 14, wherein said neutrophils have adhered to said endothelial cells in response to platelet activating factor.

16. A method for inhibiting the interaction between CD18 cell-surface antigens present in a mammal and molecules which are capable of binding to said antigens, wherein said method comprises administering to said mammal the milk anti-inflammatory factor obtained by the method of claim 1 at a dose sufficient to inhibit said interaction.

17. A method for inhibiting the emigration of leukocytes from the venous system of a mammal, wherein said method comprises administering to said mammal the milk anti-inflammatory factor obtained by the method of claim 1 at a dose sufficient to inhibit said emigration.

18. The method of claim 17, wherein said leukocytes are neutrophils.

19. A method for suppressing the mitogenic response of lymphocytes in a host mammal to foreign antigens, wherein said method comprises administering to said mammal the milk anti-inflammatory factor obtained by the method of claim 1 at a dose sufficient to suppress said mitogenic response.

20. The method of claim 19, wherein said antigens are on the cell surface.

21. The method of claim 20, wherein said cells are leukocytes.

22. The method of claim 21, wherein said cells are lymphocytes.

* * * * *